United States Patent
Suzuki et al.

(10) Patent No.: US 11,591,606 B2
(45) Date of Patent: Feb. 28, 2023

(54) TOBACCO PLANT AND PRODUCTION METHOD THEREOF

(71) Applicant: JAPAN TOBACCO INC., Tokyo (JP)

(72) Inventors: Shoichi Suzuki, Tokyo (JP); Kaori Hamano, Tokyo (JP); Masao Arai, Tokyo (JP); Ayako Nomura, Tokyo (JP); Mai Tsukahara, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 439 days.

(21) Appl. No.: 16/569,045

(22) Filed: Sep. 12, 2019

(65) Prior Publication Data
US 2020/0002711 A1 Jan. 2, 2020

Related U.S. Application Data

(63) Continuation of application No. PCT/JP2017/032871, filed on Sep. 12, 2017.

(30) Foreign Application Priority Data

Mar. 16, 2017 (JP) .............................. JP2017-051976

(51) Int. Cl.
*C12N 15/82* (2006.01)
*A01H 6/82* (2018.01)

(52) U.S. Cl.
CPC ......... *C12N 15/8218* (2013.01); *A01H 6/823* (2018.05); *C12N 15/8229* (2013.01); *C12N 15/8295* (2013.01); *C12N 2310/14* (2013.01)

(58) Field of Classification Search
None
See application file for complete search history.

(56) References Cited

FOREIGN PATENT DOCUMENTS

WO WO 2016/057515 A2 4/2016

OTHER PUBLICATIONS

"Predicted: scarecrow-like protein 22 (*Nicotiana tabacum*)", Acc. XP_016491014, 2016, Uniprot.
"Predicted: scarecrow-like protein 22 (*Nicotiana tabacum*)", Acc. XP_016487313, 2016, Uniprot.
"Predicted: scarecrow-like protein 22 isoform X1 (*Nicotiana sylvestris*)", Acc. XP_009803487, 2014, Uniprot.
"Predicted: scarecrow-like protein 22 isoform X1 (*Nicotiana tabacum*)", Acc. XP_016481267, 2016, Uniprot.
"Predicted: scarecrow-like protein 6 (*Nicotiana tabacum*)", Acc. XP_016487314, 2016, Uniprot.
"Predicted: scarecrow-like protein 6 isoform X1 (*Nicotiana tabacum*)", Acc. XP_016437509, 2016, Uniprot.
Engstrom et al., "*Arabidopsis* homologs of the *Petunia Hairy Meristem* Gene Are Required for Maintenance of Shoot and Root Indeterminacy", Plant Physiology, 2011, vol. 155, pp. 735-750.
International Search Report (PCT/ISA/210) issued in PCT/JP2017/032871, dated Dec. 19, 2017.
Japanese Journal of Phytopathology, Aug. 2011, vol. 77, No. 3, Total 2 pages.
Li et al., "Multiplex and homologous recombination-mediated genome editing in *Arabidopsis* and Nicotiana benthamiana using guide RNA and Cas9", Nature Biotechnology, 2013, vol. 31, No. 8, pp. 688-691.
Marshallsay et al., "Amplification of plant U3 and U6 snRNA gene sequences using primers specific for an upstream promoter element and conserved intragenic regions", Nucleic Acids Research, 1990, vol. 18, No. 12, pp. 3459-3466.
Schulze et al., "*Lost Meristems* genes regulate cell differentiation of central zone descendants in *Arabidopsis* shoot meristems", The Plant Journal, 2010, vol. 64, pp. 668-678. Total 24 pages.
David-Schwartz et al., "CaHAM is autoregulated and regulates CaSTM expression and is required for shoot apical meristem organization in pepper". Plant Science, 2013, vol. 203-204, pp. 8-16.
Stuurman et al., "Shoot meristem maintenance is controlled by a GRAS-gene mediated signal from differentiating cells", Genes & Development 2002, vol. 16, pp. 2213-2218.
Waibel et al., "U6 snRNA genes of *Arabidopsis* are transcribed by RNA polymerase III but contain the same two upstream promoter elements as RNA polymerase II-transcribed U-snRNA genes", Nucleic Acids Research, 1990, vol. 18, No. 12, pp. 3451-3458.
Written Opinion (PCT/ISA/237) issued in PCT/JP2017/032871, dated Dec. 19, 2017.
Gao et al., "NtBRC1 suppresses axillary branching in tobacco after decapitation," Genetics and Molecular Research, vol. 15, No. 4, Dec. 19, 2016, pp. 1-10.
Indian Office Action for Indian Application No. 201947041414, dated Mar. 15, 2022, with English translation.
Sun et al., "Inhibition of tobacco axillary bud differentiation by silencing Cup-Shaped Cotyledon 3," African Journal of Biotechnology, vol. 11, No. 16, Feb. 23, 2012, pp. 3919-3927.

*Primary Examiner* — Elizabeth F McElwain
(74) *Attorney, Agent, or Firm* — Birch, Stewart, Kolasch & Birch, LLP

(57) ABSTRACT

Provided is a tobacco plant which is suitable for cultivation for harvesting leaf tobaccos. The present invention encompasses (i) a tobacco plant into which a mutation for suppressing the development of primary axillary buds is introduced, (ii) a method of obtaining the tobacco plant, (iii) a harvest from the tobacco plant, and (iv) a processed product of the harvest.

18 Claims, 7 Drawing Sheets

Specification includes a Sequence Listing.

SEQUENCE LISTING

```
<160> NUMBER OF SEQ ID NOS: 89

<210> SEQ ID NO 1
<211> LENGTH: 626
<212> TYPE: PRT
<213> ORGANISM: Nicotiana tabacum

<400> SEQUENCE: 1

Met Leu Val Thr Thr Ser His Ser Pro Ser Ala Ser Ala Ser Ser Ser
1               5                   10                  15

Ser Cys Ser Tyr Gly Gly Asn Met Gly Glu Lys Ser Asp Leu Gly Phe
            20                  25                  30

Gly Asp Leu Asp Asn Leu Leu Pro Glu Leu Ala Gly Ser Asp Gln Thr
        35                  40                  45

Leu Phe Arg Cys Ile Ser Gly Asp Met Glu Asp Pro Ser Ile Ser Leu
    50                  55                  60

Lys Gln Leu Leu Gln Gly Gly Asn Glu Asn Ala Asp Leu Ser Cys Gly
65                  70                  75                  80

Val Ser Val Gln Ser Ser Gly Phe Glu Val Ser Ala Ala Gly Ser Leu
```

```
                     85                  90                  95
Ala His Thr Asp Asn Val Ser Phe Ser Asn Ser Asn Leu Leu Leu Asn
            100                 105                 110

Ala Asn Ile Glu Lys Ile Gly Ser Val Ile Asn Ser Asp Asn Lys Gln
            115                 120                 125

Asn Val Asn Phe Glu His Leu Asn Val Asn Leu Leu Ala Arg Asn Leu
            130                 135                 140

Pro Pro Ala Leu Ser Phe Gln Glu Gln Gln Ser Glu Gln Asn Ser Ala
145                 150                 155                 160

Tyr Val Asn Met Leu Gly Ser Leu Ser Tyr Asp Val Thr Gln Glu Gln
            165                 170                 175

Pro Pro Pro Lys Arg His Asn Ser Gly Thr Leu Gly Ser Ser Leu Ser
            180                 185                 190

Ala Leu Leu Pro Glu Val Pro Phe Phe Asp Ser Gly Glu Leu Leu
            195                 200                 205

Leu Arg Lys Gln Pro Leu Gly Gln Thr Arg Gln Gln Val Asn Phe Leu
            210                 215                 220

Pro Phe His Gln Phe Gln Gln Lys Pro Leu Ile Val Pro Lys Leu Glu
225                 230                 235                 240

Ala Ala Val Gly Gly Ala Asn Gly Asn Leu Met Val Pro Cys His Gln
            245                 250                 255

Gln Gln Glu Gln Gln Phe Ile Tyr Asp Gln Ile Phe Gln Ala Ser Glu
            260                 265                 270

Leu Leu Leu Ala Gly Gln Phe Ser Asn Ala Gln Met Ile Leu Ala Arg
            275                 280                 285

Leu Asn Gln Gln Leu Ser Pro Leu Gly Lys Pro Phe Lys Arg Ser Ala
            290                 295                 300

Phe Tyr Phe Lys Glu Ala Leu Leu Leu Pro Phe Leu Leu Pro Cys Thr
305                 310                 315                 320

Ser Thr Ser Phe Pro Pro Arg Ile Pro Thr Pro Phe Asp Cys Val Leu
            325                 330                 335

Lys Met Asp Ala Tyr Lys Ala Phe Ser Glu Ile Ser Pro Leu Ile Gln
            340                 345                 350

Phe Met Asn Phe Thr Ser Asn Gln Pro Ile Leu Glu Ala Leu Gly Asp
            355                 360                 365

Ala Lys Glu Ile His Ile Ile Asp Phe Asp Ile Gly Cys Gly Ala Gln
            370                 375                 380

Trp Ser Ser Phe Met Gln Glu Leu Arg Ser Ser Asn Arg Lys Ala Thr
385                 390                 395                 400

Ser Leu Lys Ile Thr Ala Phe Val Ser Pro Ser Thr His His Ser Val
            405                 410                 415

Glu Ile Gly Ile Met His Glu Ser Leu Thr Leu Phe Ala Asn Asp Val
            420                 425                 430

Gly Ile Arg Phe Glu Leu Glu Val Ile Asn Leu Asp Ser Phe Asp Pro
            435                 440                 445

Lys Thr Tyr Pro Leu Ser Ser Leu Arg Ser Ser Glu Cys Glu Ala Ile
            450                 455                 460

Ala Ile Asn Phe Pro Ile Trp Ser Ile Ser Ser Cys Leu Phe Ala Phe
465                 470                 475                 480

Pro Ser Leu Leu His Cys Met Lys Gln Leu Ser Pro Lys Val Val Val
            485                 490                 495

Ser Leu Glu Arg Gly Cys Glu Arg Thr Glu Leu Pro Leu Lys His His
            500                 505                 510
```

Leu Leu His Ala Leu Gln Tyr Tyr Glu Ile Leu Leu Ala Ser Ile Asp
            515                 520                 525

Ala Ala Asn Leu Thr Pro Glu Ile Gly Lys Lys Ile Glu Arg Ser Leu
            530                 535                 540

Leu Gln Pro Ser Ile Glu Asn Thr Val Leu Gly Arg Leu Arg Ser Pro
545                 550                 555                 560

Asp Arg Met Pro Pro Trp Arg Asn Leu Phe Ala Ser Ala Gly Phe Ser
                565                 570                 575

Pro Ile Glu Phe Ser Asn Met Ala Glu Ile Gln Ala Glu Cys Val Val
            580                 585                 590

Lys Arg Thr Gln Val Gly Gly Phe His Val Glu Lys Arg Gln Met Ser
            595                 600                 605

Leu Val Leu Cys Trp Lys Gln Gln Glu Leu Leu Ser Ile Leu Ala Trp
            610                 615                 620

Arg Cys
625

<210> SEQ ID NO 2
<211> LENGTH: 624
<212> TYPE: PRT
<213> ORGANISM: Nicotiana tabacum

<400> SEQUENCE: 2

Met Leu Val Thr Thr Ser His Ser Pro Ser Ala Ser Ala Ser Ser Cys
1               5                   10                  15

Ser Tyr Gly Gly Asn Met Ala Glu Lys Ser Asp Leu Gly Phe Gly Asp
            20                  25                  30

Leu Asp Asn Leu Leu Pro Glu Leu Ala Gly Ser Asp Gln Thr Leu Phe
            35                  40                  45

Arg Cys Ile Ser Gly Asp Met Glu Asp Pro Ser Val Ser Leu Lys Gln
        50                  55                  60

Leu Leu Gln Gly Gly Asn Ala Asn Ala Asp Leu Gly Cys Gly Val Ser
65                  70                  75                  80

Val Gln Ser Ser Gly Phe Glu Val Ser Ala Ala Gly Ser Leu Ala His
            85                  90                  95

Thr Asp Asn Val Ser Phe Ser Asn Ser Asn Leu Leu Leu Asn Ala Asn
            100                 105                 110

Ile Glu Lys Ile Gly Ser Val Ile Asn Ser Asp Asn Lys Gln Asn Val
        115                 120                 125

Asn Phe Glu His Leu Asn Val Asn Leu Leu Ala Arg Asn Leu Pro Pro
    130                 135                 140

Ala Leu Ser Phe Gln Glu Gln Pro Ser Glu Gln Asn Ser Ala Tyr Val
145                 150                 155                 160

Asn Met Leu Gly Ser Leu Ser Tyr Asp Ile Ser Gln Glu Gln Pro Pro
            165                 170                 175

Pro Lys Arg His Asn Ser Gly Thr Leu Gly Ser Ser Leu Ser Ala Leu
            180                 185                 190

Leu Pro Glu Val Pro Phe Phe Asp Ser Ser Gly Asp Leu Leu Leu Arg
        195                 200                 205

Lys Gln Pro Leu Gly Gln Met Arg Gln Gln Val Asn Phe Leu Pro Phe
    210                 215                 220

His Gln Phe Gln Gln Lys Pro Leu Ile Val Pro Lys Leu Glu Ala Ala
225                 230                 235                 240

Gly Gly Gly Gly Asn Gly Asn Leu Ile Val Pro Arg His Gln Gln Gln

```
            245                 250                 255
Glu Gln Gln Phe Ile Tyr Asp Gln Phe Phe Gln Ala Ser Glu Leu Leu
            260                 265                 270

Leu Ala Gly Gln Phe Ser Asn Ala Gln Met Ile Leu Ala Arg Leu Asn
        275                 280                 285

Gln Gln Leu Ser Pro Ile Gly Lys Pro Phe Lys Arg Ser Ala Phe Tyr
    290                 295                 300

Phe Lys Glu Ala Leu Gln Leu Pro Phe Leu Pro Cys Thr Ser Thr
305                 310                 315                 320

Ser Phe Pro Pro Arg Ile Pro Thr Pro Phe Asp Cys Val Leu Lys Met
                325                 330                 335

Asp Ala Tyr Lys Ala Phe Ser Glu Ile Ser Pro Leu Ile Gln Phe Met
            340                 345                 350

Asn Phe Thr Ser Asn Gln Pro Ile Leu Glu Ala Leu Gly Asp Ala Lys
        355                 360                 365

Gln Ile His Ile Ile Asp Phe Asp Ile Gly Cys Gly Ala Gln Trp Ser
    370                 375                 380

Ser Phe Met Gln Glu Leu Arg Ser Ser Asn Arg Lys Ala Thr Ser Leu
385                 390                 395                 400

Lys Ile Thr Ala Phe Val Ser Pro Ser Thr His Ser Val Glu Ile
                405                 410                 415

Gly Ile Met His Glu Ser Leu Thr Leu Phe Ala Asn Asp Val Gly Ile
            420                 425                 430

Arg Phe Glu Leu Glu Val Ile Asn Leu Asp Ser Phe Asp Pro Lys Thr
        435                 440                 445

Tyr Pro Leu Ser Ser Leu Arg Ser Ser Glu Cys Glu Ala Ile Ala Ile
    450                 455                 460

Asn Phe Pro Ile Trp Ser Ile Ser Ser Cys Leu Phe Ala Phe Pro Ser
465                 470                 475                 480

Leu Leu His Cys Met Lys Gln Leu Ser Pro Lys Val Val Ser Leu
                485                 490                 495

Glu Arg Gly Cys Glu Arg Thr Glu Leu Pro Leu Lys His His Leu Leu
            500                 505                 510

His Ala Leu Gln Tyr Tyr Glu Ile Leu Leu Ala Ser Ile Asp Ala Ala
        515                 520                 525

Asn Leu Thr Pro Glu Ile Gly Lys Lys Ile Glu Arg Ser Leu Leu Gln
    530                 535                 540

Pro Ser Ile Glu Asn Met Val Leu Gly Arg Leu Arg Ser Pro Asp Arg
545                 550                 555                 560

Met Pro Pro Trp Arg Asn Leu Phe Ala Ser Ala Gly Phe Ser Pro Ile
                565                 570                 575

Glu Phe Ser Asn Met Ala Glu Ile Gln Ala Glu Cys Val Val Lys Arg
            580                 585                 590

Thr Gln Val Gly Gly Phe His Val Glu Lys Arg Gln Thr Ser Leu Val
        595                 600                 605

Leu Cys Trp Lys Gln Gln Glu Leu Leu Ser Ile Leu Ala Trp Arg Cys
    610                 615                 620

<210> SEQ ID NO 3
<211> LENGTH: 714
<212> TYPE: PRT
<213> ORGANISM: Nicotiana tabacum

<400> SEQUENCE: 3
```

```
Met Ile Val Ile Pro Gln Ser Asn Asn Leu Ala Gly Ala Lys Gly Val
1               5                   10                  15

Leu Gly Val Ser Gly Tyr Val Pro Ser Ile Ser Ser Pro Glu Ala
            20                  25                  30

Ala Ile Cys Asn Lys Gly Leu Asn Phe Thr Arg Asn Glu Ser Val Ser
            35                  40                  45

Val Leu Asp Ala Arg Ser Pro Ser Pro Ser Ala Ser Ser Ser Ser Cys
50                      55                  60

Ser Tyr Gly Gly Gln Tyr Ala Gly Asn Asn Val Pro Gly Ala Gly
65                  70                  75                  80

Ala Gly Lys Ile Asp Gly Arg Lys Glu Glu Leu Val Thr Glu Leu Gln
                85                  90                  95

Pro Phe Ser Phe Glu Leu Glu Pro Glu Lys Phe Asn Leu Gly Phe Gly
            100                 105                 110

Asp Leu Asp Asn Leu Leu Pro Glu Leu Ala Gly Ser Asp Gln Thr Ile
            115                 120                 125

Phe Arg Trp Ile Ser Gly Asp Met Glu Asp Pro Ser Val Ser Leu Lys
        130                 135                 140

Gln Leu Leu Gln Gly Gly Asn Ala Asn Ala Asp Leu Gly Cys Gly Val
145                 150                 155                 160

Ser Val Ala Gly Ser Phe Ala Cys Thr Asp Asn Ile Ser Phe Ser Ser
                165                 170                 175

Ser Asp Ile Ser Leu Asp Ala Asn Ile Glu Lys Ile Gly Ser Val Val
            180                 185                 190

Ile Asp Ser Asn Asn Arg Pro Asn Asn Asn Phe Glu Asn Pro Asn Val
        195                 200                 205

Asn Leu Leu Ala Lys Ser Leu Pro Pro Thr Leu Ser Phe His Glu Gln
        210                 215                 220

Gln Ser Glu Glu Lys Pro Gln Ile Ser Cys Pro Gln Ile Met Thr Asn
225                 230                 235                 240

Gln His Gln Phe Gln Asn Ser Ala Tyr Val Asn Leu Phe Gly Ser Ser
                245                 250                 255

Ser Tyr Asn Met Asn Gln Glu Gln Pro Pro Lys Arg His Asn Ser
            260                 265                 270

Gly Ile Leu Gly Ser Ser Leu Gly Phe Leu Leu Pro Lys Val Pro Phe
        275                 280                 285

Phe Asn Pro Ser Gly Asp Leu Leu Arg Lys Gln Pro Leu Gly His
    290                 295                 300

Met Gln Gln Gln Val Asn Leu Leu Pro His Gln Phe Gln Pro Thr
305                 310                 315                 320

Ser Leu Phe Val Pro Lys Leu Glu Ala Ala Gly Gly Asp Gly Asn Gly
                325                 330                 335

Asn Leu Met Val Pro Arg His Gln Gln Gln Glu Gln Gln Phe Ile Tyr
            340                 345                 350

Asp Gln Ile Phe Gln Ala Ser Glu Leu Leu Leu Ala Gly His Phe Ser
        355                 360                 365

Asn Ala Gln Met Ile Leu Ala Arg Leu Asn Gln Gln Leu Ser Pro Ile
    370                 375                 380

Gly Lys Pro Phe Lys Arg Ala Ala Phe Tyr Phe Lys Glu Ala Leu Gln
385                 390                 395                 400

Leu Pro Phe Leu Leu Pro Cys Thr Ser Thr Ser Phe Pro Pro Arg Ile
                405                 410                 415

Pro Thr Pro Phe Asp Cys Val Leu Lys Met Asp Ala Tyr Lys Ala Phe
```

```
            420                 425                 430
Ser Glu Val Ser Pro Leu Ile Gln Phe Met Asn Phe Thr Ser Asn Gln
            435                 440                 445

Ala Ile Leu Glu Ala Leu Gly Asp Ala Lys Gln Ile His Ile Ile Asp
            450                 455                 460

Phe Asp Ile Gly Cys Gly Ala Gln Trp Ser Ser Phe Met Gln Glu Leu
465                 470                 475                 480

Pro Ser Ser Asn Arg Lys Ala Thr Ser Leu Lys Ile Thr Ala Phe Val
            485                 490                 495

Ser Pro Ser Thr His His Ser Val Glu Ile Gly Ile Met His Glu Ser
            500                 505                 510

Leu Thr Leu Phe Ala Asn Asp Val Gly Ile Arg Phe Glu Leu Glu Val
            515                 520                 525

Ile Asn Leu Asp Ser Phe Asp Pro Lys Thr Tyr Pro Leu Ser Ser Leu
            530                 535                 540

Arg Ser Ser Glu Cys Glu Ala Ile Ala Ile Asn Phe Pro Ile Trp Ser
545                 550                 555                 560

Ile Ser Ser Cys Leu Phe Ala Phe Pro Ser Leu Leu His Cys Met Lys
            565                 570                 575

Gln Leu Ser Pro Lys Val Val Ser Leu Glu Arg Gly Cys Glu Arg
            580                 585                 590

Thr Glu Leu Pro Leu Lys His His Leu Leu His Ala Leu Gln Tyr Tyr
            595                 600                 605

Glu Ile Leu Leu Ala Ser Ile Asp Ala Ala Asn Leu Thr Pro Asp Val
610                 615                 620

Gly Lys Lys Ile Glu Arg Ser Leu Leu Gln Ser Ser Ile Glu Asn Met
625                 630                 635                 640

Val Leu Gly Arg Leu Arg Ser Pro Asn Arg Ile Pro Pro Trp Arg Asn
            645                 650                 655

Leu Phe Ala Ser Ala Gly Phe Ser Pro Val Ala Phe Ser Asn Leu Thr
            660                 665                 670

Glu Ile Gln Ala Glu Cys Leu Val Lys Arg Thr Gln Val Gly Gly Phe
            675                 680                 685

His Val Glu Lys Arg Gln Thr Ser Leu Val Leu Cys Trp Lys Gln Gln
            690                 695                 700

Glu Leu Leu Ser Ala Leu Ser Trp Arg Cys
705                 710

<210> SEQ ID NO 4
<211> LENGTH: 714
<212> TYPE: PRT
<213> ORGANISM: Nicotiana tabacum

<400> SEQUENCE: 4

Met Ile Val Ile Pro Gln Ser Asn Asn Leu Ala Val Ala Lys Gly Val
1               5                   10                  15

Leu Gly Val Ser Ser Tyr Val Pro Ser Ile Ser Ser Ser Thr Glu Ala
            20                  25                  30

Pro Ile Cys Asn Lys Gly Leu Thr Phe Thr Arg Asn Glu Ser Val Ser
            35                  40                  45

Val Leu Asp Thr Arg Ser Pro Ser Pro Ala Ser Ser Ser Cys
            50                  55                  60

Ser Tyr Gly Gly Gln His Ala Gly Asn Asn Gly Val Pro Gly Ala Gly
65                  70                  75                  80
```

```
Ala Gly Lys Ile Asp Gly Arg Lys Glu Glu Leu Val Thr Glu Leu Gln
             85                  90                  95
Pro Phe Ser Phe Gly Leu Glu Pro Glu Lys Phe Asn Leu Gly Phe Gly
            100                 105                 110
Asp Leu Asp Asn Leu Leu Pro Glu Leu Ala Gly Ser Asp Gln Thr Ile
            115                 120                 125
Phe Arg Trp Ile Ser Gly Asp Met Glu Asp Pro Ser Val Ser Leu Lys
            130                 135                 140
Gln Leu Leu Gln Gly Asn Ala Asn Ala Asp Leu Gly Gly Gly Val
145                 150                 155                 160
Ser Val Ala Gly Ser Phe Ala Cys Thr Asp Asn Ile Ser Phe Ser Ser
                165                 170                 175
Ser Asp Ile Ser Leu Asp Ala Asn Ile Glu Lys Ile Gly Tyr Ala Val
            180                 185                 190
Ile Asp Ser Asn Asn Arg Pro Asn Asn Asn Phe Glu Asn Leu Asn Ala
            195                 200                 205
Asn Leu Leu Ala Lys Ser Leu Pro Pro Ala Leu Ser Phe Gln Glu Gln
            210                 215                 220
Gln Ser Glu Glu Lys Pro Gln Ile Ser Cys Pro Gln Ile Val Ala Asn
225                 230                 235                 240
Gln Thr Gln Phe Gln Asn Ser Ala Tyr Val Asn Leu Phe Gly Ser Ser
                245                 250                 255
Ser Tyr Asn Met Asn Gln Glu Gln Pro Pro Lys Arg His Asn Ser
            260                 265                 270
Gly Ile Leu Gly Ser Ser Leu Gly Phe Leu Leu Pro Lys Val Pro Phe
            275                 280                 285
Phe Ser Pro Ser Gly Asp Leu Leu Arg Lys Gln Pro Leu Gly Gln
            290                 295                 300
Met Gln Gln Gln Val Asn Leu Leu Pro Pro His Gln Phe Gln Pro Thr
305                 310                 315                 320
Pro Leu Phe Val Pro Lys Leu Glu Ala Ala Gly Gly Gly Gly Asn Gly
                325                 330                 335
Asn Leu Val Val Pro Arg His Gln Gln Gln Glu Gln Gln Phe Ile Tyr
            340                 345                 350
Asp Gln Ile Phe Gln Ala Ser Glu Leu Leu Leu Ala Gly His Phe Ser
            355                 360                 365
Asn Ala Gln Met Ile Leu Ala Arg Leu Asn Gln Gln Leu Ser Pro Ile
            370                 375                 380
Gly Lys Pro Phe Lys Arg Ala Ala Phe Tyr Phe Lys Glu Ala Leu Gln
385                 390                 395                 400
Leu Pro Phe Leu Leu Pro Cys Thr Ser Thr Ser Phe Pro Pro Arg Ile
                405                 410                 415
Pro Thr Pro Phe Asp Cys Val Leu Lys Met Asp Ala Tyr Lys Ala Phe
            420                 425                 430
Ser Glu Val Ser Pro Leu Ile Gln Phe Met Asn Phe Thr Ser Asn Gln
            435                 440                 445
Ala Ile Leu Glu Ala Leu Gly Ala Ala Lys Gln Ile His Ile Ile Asp
            450                 455                 460
Phe Asp Ile Gly Cys Gly Ala Gln Trp Ser Leu Met Gln Glu Leu
465                 470                 475                 480
Pro Ser Ser Asn Arg Lys Ala Thr Ser Leu Lys Ile Thr Ala Phe Val
                485                 490                 495
Ser Pro Ser Thr His His Ser Val Glu Ile Gly Ile Met His Glu Ser
```

```
                500                 505                 510
Leu Thr Leu Phe Ala Asn Asp Val Gly Ile Arg Phe Glu Leu Glu Val
            515                 520                 525

Ile Asn Leu Asp Ser Phe Asp Pro Lys Thr Tyr Pro Leu Ser Ser Leu
        530                 535                 540

Arg Ser Ser Glu Cys Glu Ala Ile Ala Ile Asn Phe Pro Ile Trp Ser
545                 550                 555                 560

Ile Ser Ser Cys Leu Phe Ala Phe Pro Ser Leu Leu His Cys Met Lys
            565                 570                 575

Gln Leu Ser Pro Lys Val Val Ser Leu Glu Arg Gly Cys Glu Arg
        580                 585                 590

Thr Glu Leu Pro Leu Lys His His Leu Leu His Ala Leu Gln Tyr Tyr
            595                 600                 605

Glu Ile Leu Leu Ala Ser Ile Asp Ala Ala Asn Leu Thr Pro Asp Val
        610                 615                 620

Gly Lys Lys Ile Glu Arg Ser Leu Phe Gln Ser Ser Ile Glu Asn Met
625                 630                 635                 640

Val Leu Gly Arg Leu Arg Ser Pro Asp Arg Ile Pro Pro Trp Arg Asn
            645                 650                 655

Leu Phe Ala Ser Ala Gly Phe Ser Pro Val Ala Phe Ser Asn Leu Thr
            660                 665                 670

Glu Ile Gln Ala Glu Cys Leu Val Lys Arg Thr Gln Val Gly Gly Phe
        675                 680                 685

His Val Glu Lys Arg Gln Ser Ser Leu Val Leu Cys Trp Lys Gln Arg
        690                 695                 700

Glu Leu Leu Ser Ala Leu Ser Trp Arg Cys
705                 710

<210> SEQ ID NO 5
<211> LENGTH: 755
<212> TYPE: PRT
<213> ORGANISM: Nicotiana tabacum

<400> SEQUENCE: 5

Met Lys Gly Met Pro Leu Pro Phe Asp Phe Glu Gly Lys Gly Val Leu
1               5                   10                  15

Asp Leu Asp Val Val Leu Asn Lys Asn Ser Ile Leu Asn Ser Trp Asn
            20                  25                  30

Tyr Asn Ser Lys Glu Ser Cys Tyr Leu Val Asn Ser Pro Ser Ala Val
        35                  40                  45

Leu Asp Ile Ile Arg Ser Pro Arg Pro Val Thr Ser Ser Ser Thr Leu
    50                  55                  60

Ser Ser Ser Leu Gly Gly Gly Gly Gly Gly Gly Thr Ala Ser
65                  70                  75                  80

Thr Asp Thr Ala Gly Ala Val Ser Ala Asn Pro Ser Ser Lys Trp Gln
                85                  90                  95

Gln Gln Gln Gln Gln Asp Asn Thr Thr Ala Thr Ser Ser Asn Val
            100                 105                 110

Gly Gly Ala Ala Ala Glu Ser Glu Phe Gln Gln Val Ala Ala Ala Ser
        115                 120                 125

Ala Ala Ala Thr Glu Gly Lys Lys Cys Ala Met Glu Glu Trp Glu Gly
    130                 135                 140

Gly Leu Ser Glu Ser Val Met Ala Ser Pro Cys Gln Glu Gln Ser Ile
145                 150                 155                 160
```

-continued

```
Leu Gly Trp Ile Met Gly Asp Val Asp Pro Ser Met Ser Asn Leu
            165                 170                 175
Asn Lys Val Leu Gln Val Ser Gly Pro Met Asp Tyr Glu Phe Asn Ala
        180                 185                 190
Gly Phe Gly Val Val Asp Gln Gly Phe Gly Val Asp Gln Ile Gly Thr
            195                 200                 205
Ser Ser Phe Met Pro Ala Ile Asn Asn Ser Ser Val Ser Ser Phe Pro
    210                 215                 220
Pro Thr Ser Thr Arg Met Asn Asn Asp Lys Ile Gly Leu Phe Ser Asn
225                 230                 235                 240
Ile Pro Thr Asn Leu Ser Gln Asn Pro Ile Phe Pro Ser Phe Ser Asn
                245                 250                 255
Asn Leu Gly Pro Val Ser Phe Ser Gln Thr Gln Gln Pro Phe Glu
            260                 265                 270
Ser Thr Asp Leu Lys Pro Gln Ser Phe His Ser His Phe Leu Ile Asn
        275                 280                 285
Gln His Gln Thr Gln Ile Pro Gln Asn Pro Ser Phe Leu Leu Pro Leu
    290                 295                 300
Pro Phe Ala Gln Gln Glu Gln Asn Leu Val Leu Pro Pro Lys Ala Lys
305                 310                 315                 320
Arg His Asn Pro Gly Thr Leu Glu Gln Gln Gly Ser Gln Ile Ser Gln
                325                 330                 335
Glu Leu Phe Ile Asp Ala Gly Gln Gln Gln Pro Thr Pro Ser His Gln
            340                 345                 350
Leu Gln Leu Leu Pro His Phe Arg Pro Gly Val Pro Ile Gly Thr Lys
        355                 360                 365
Pro Lys Met Val Gly Glu Glu Met Gly Gln Phe His Gln Leu Gln Leu
370                 375                 380
Gln Gln Gln Gln Gln Ala Ile Ile Asp Gln Leu Phe Lys Ala Ala
385                 390                 395                 400
Glu Leu Val Gln Thr Gly Asn Pro Val Leu Ala Gln Gly Ile Leu Ala
            405                 410                 415
Arg Leu Asn His Gln Leu Ser Pro Ile Gly Lys Pro Phe Tyr Arg Ala
        420                 425                 430
Ala Phe Tyr Cys Lys Glu Ala Leu Gln Leu Leu His Thr Asn Thr
    435                 440                 445
Asn Asn Leu Asn Asn Pro Ser Ile Pro Ser Ser Pro Phe Asn Leu
        450                 455                 460
Ile Phe Lys Ile Gly Ala Tyr Lys Ser Phe Ser Glu Ile Ser Pro Val
465                 470                 475                 480
Ala Gln Phe Ala Asn Phe Thr Cys Asn Gln Ala Leu Leu Glu Val Leu
            485                 490                 495
Asp Gly Phe Glu Arg Ile His Ile Val Asp Phe Asp Ile Gly Tyr Gly
        500                 505                 510
Arg Gln Trp Ala Ser Leu Met Gln Glu Leu Ala Leu Arg Ser Gly Gly
    515                 520                 525
Ala Pro Thr Leu Lys Ile Thr Ala Leu Ala Ser Pro Ser Thr His Asp
530                 535                 540
Gln Leu Glu Leu Gly Leu Thr Arg Glu Ser Leu Ile His Phe Ala Asn
545                 550                 555                 560
Glu Ile Asn Met Glu Phe Glu Phe Glu Ile Leu Ser Ile Asp Ser Leu
            565                 570                 575
Asn Ser Thr Ser Trp Ser Leu Pro Pro Leu Val Ser Glu Asn Glu Ala
```

```
                        580                 585                 590
Ile Ala Val Asn Leu Pro Ile Ser Ser Leu Ala Ser Tyr Gln Leu Ser
                595                 600                 605

Leu Pro Leu Val Leu Arg Phe Val Lys Gln Leu Ser Pro Arg Ile Val
            610                 615                 620

Val Ser Val Asp Lys Gly Cys Asp Arg Thr Asp Leu Pro Phe Pro Asn
625                 630                 635                 640

His Val Ile Gln Ile Leu Gln Ser Tyr Ser Asn Leu Leu Glu Ser Leu
                645                 650                 655

Asp Ala Val Asn Val Asn Phe Asp Ala Leu Gln Lys Ile Glu Arg Phe
            660                 665                 670

Leu Leu Gln Pro Arg Ile Glu Arg Ile Val Met Ser Arg Phe Arg Ser
        675                 680                 685

Pro Glu Lys Thr Gln His Trp Arg Ala Leu Phe Leu Ser Ser Gly Leu
            690                 695                 700

Ser Pro Leu Pro Phe Ser Asn Phe Thr Glu Ser Gln Ala Glu Cys Val
705                 710                 715                 720

Val Lys Arg Thr Pro Val Arg Gly Phe His Val Glu Lys Arg Gln Ser
                725                 730                 735

Ser Leu Val Leu Cys Trp Gln Arg Lys Glu Leu Ile Ser Ala Ser Ala
            740                 745                 750

Trp Arg Cys
        755

<210> SEQ ID NO 6
<211> LENGTH: 754
<212> TYPE: PRT
<213> ORGANISM: Nicotiana tabacum

<400> SEQUENCE: 6

Met Lys Gly Met Pro Leu Pro Phe Asp Phe Glu Gly Lys Gly Val Leu
1               5                   10                  15

Asp Leu Asp Val Val Leu Asn Lys Asn Ser Ile Phe Asn Ser Trp Asn
            20                  25                  30

Tyr Asn Ser Lys Glu Ser Cys Tyr Leu Val Asn Ser Pro Ser Ala Val
        35                  40                  45

Leu Asp Ile Ile Arg Ser Pro Arg Pro Val Thr Ser Ser Ser Thr Leu
    50                  55                  60

Ser Ser Ser Phe Gly Gly Gly Gly Gly Gly Thr Ala Ser Thr
65                  70                  75                  80

Asp Thr Ala Gly Ala Val Ser Ala Asn Pro Ser Ser Lys Trp Gln Gln
                85                  90                  95

Gln Gln Gln Gln Asp Asn Thr Thr Ala Thr Ser Ser Asn Val Gly Gly
            100                 105                 110

Ala Ala Ala Glu Ser Glu Leu Leu Gln Val Ala Ala Thr Glu Gly
        115                 120                 125

Lys Lys Cys Gly Met Glu Glu Trp Gly Gly Leu Ser Glu Ser Val
    130                 135                 140

Met Ala Ser Pro Cys Gln Glu Gln Ser Ile Leu Gly Trp Ile Met Gly
145                 150                 155                 160

Asp Val Asp Asp Thr Ser Met Ser Asn Leu Asn Lys Val Leu Gln Val
                165                 170                 175

Ser Gly Pro Met Asp Tyr Glu Phe Asn Ala Gly Phe Gly Val Val Asp
            180                 185                 190
```

```
Gln Gly Phe Gly Val Asp Gln Ile Gly Thr Ser Ser Phe Met Pro Ala
        195                 200                 205
Ile Asn Ser Ser Ser Val Ser Ser Phe Pro Thr Thr Thr Arg Met
210                 215                 220
Asn Ser Asp Lys Ile Gly Leu Leu Ser Asn Ile Pro Thr His Leu Pro
225                 230                 235                 240
Gln Asn Pro Ile Phe Pro Ser Phe Ser Asn Asn Leu Gly Pro Val Ser
                245                 250                 255
Phe Ser Gln Thr Gln Gln Gln Pro Phe Glu Ser Thr Asp Leu Lys
            260                 265                 270
Pro Gln Ser Phe His Ser Gln Phe Leu Ile Asp Gln His Gln Thr Gln
        275                 280                 285
Ile Pro Gln Asn Pro Ser Phe Leu Leu Pro Leu Pro Phe Ala Gln Gln
290                 295                 300
Glu Gln Asn Leu Val Leu Pro Pro Lys Ala Lys Arg His Asn Pro Gly
305                 310                 315                 320
Thr Leu Glu Gln Pro Gly Ser Gln Ile Ser Gln Gly Leu Phe Ile Asp
                325                 330                 335
Ala Gly Glu Gln Gln Pro Thr Pro Ser His Gln Leu Gln Leu Leu Pro
            340                 345                 350
His Phe Arg Pro Gly Gly Pro Ile Gly Thr Lys Pro Lys Met Val Gly
        355                 360                 365
Glu Glu Met Gly Gln Phe His Gln Leu Gln Leu Gln Gln Gln Gln Gln
370                 375                 380
Gln Gln Gln Gln Gln Ala Ile Ile Asp Gln Leu Phe Lys Ala Ala Glu
385                 390                 395                 400
Leu Val Gln Thr Gly Asn Pro Val Leu Ala Gln Gly Ile Leu Ala Arg
                405                 410                 415
Leu Asn His Gln Leu Ser Pro Ile Gly Lys Pro Phe Tyr Arg Ala Ala
            420                 425                 430
Phe Tyr Cys Lys Glu Ala Leu Gln Leu Leu His Thr Asn Thr Asn
        435                 440                 445
Asn Leu Asn Asn Pro Ser Ile Pro Ser Ser Ser Pro Phe Ser Leu Ile
450                 455                 460
Phe Lys Ile Gly Ala Tyr Lys Ser Phe Ser Glu Ile Ser Pro Val Ala
465                 470                 475                 480
Gln Phe Ala Asn Phe Thr Cys Asn Gln Ala Leu Leu Glu Val Leu Asp
                485                 490                 495
Gly Phe Glu Arg Ile His Ile Val Asp Phe Asp Ile Gly Tyr Gly Arg
            500                 505                 510
Gln Trp Ala Ser Leu Met Gln Glu Leu Ala Leu Arg Ser Gly Gly Ala
        515                 520                 525
Pro Thr Leu Lys Ile Thr Ala Leu Ala Ser Pro Ser Thr His Asp Gln
530                 535                 540
Leu Glu Leu Gly Leu Thr Arg Glu Ser Leu Ile His Phe Ala Asn Glu
545                 550                 555                 560
Ile Asn Met Glu Phe Glu Phe Glu Ile Leu Ser Ile Asp Ser Leu Asn
                565                 570                 575
Ser Thr Ser Trp Ser Leu Pro Leu Val Ser Glu Asn Glu Ala Ile
            580                 585                 590
Ala Val Asn Leu Pro Val Ser Ser Leu Ser Ser Tyr Gln Leu Ser Leu
        595                 600                 605
Pro Leu Val Leu Gly Phe Val Lys Gln Leu Ser Pro Arg Ile Val Val
```

```
Ser Val Asp Lys Gly Cys Asp Arg Thr Asp Leu Pro Phe Pro Asn His
625                 630                 635                 640

Val Ile Gln Val Leu Gln Ser Tyr Ser Asn Leu Leu Glu Ser Leu Asp
                645                 650                 655

Ala Val Asn Val Asn Phe Asp Ala Leu Gln Lys Ile Glu Arg Phe Leu
                660                 665                 670

Leu Gln Pro Arg Ile Glu Arg Thr Val Met Gly Arg Phe Arg Ser Pro
            675                 680                 685

Glu Lys Ala Gln His Trp Arg Ala Leu Phe Leu Ser Ser Gly Leu Ser
690                 695                 700

Pro Leu Pro Phe Ser Asn Phe Ala Glu Ser Gln Ala Glu Cys Val Val
705                 710                 715                 720

Lys Arg Thr Pro Val Arg Gly Phe His Val Glu Lys Arg Gln Ser Ser
                725                 730                 735

Leu Val Leu Cys Trp Gln Arg Lys Glu Leu Ile Ser Ala Ser Ala Trp
            740                 745                 750

Arg Cys
```

<210> SEQ ID NO 7
<211> LENGTH: 2219
<212> TYPE: DNA
<213> ORGANISM: Nicotiana tabacum

<400> SEQUENCE: 7

```
acctcaatgt attcctaaat cctaacacct aaaggggttg ttggtgtttc tggttttgtg    60
cctaatttat tcttcaccag aagcaccaat ttgcaattaa tattcaaact ttacaagaaa   120
ttgaacttgt ttctatgttg gttacgacaa gtcacagtcc ttcagcttca gcttcatctt   180
cctcatgctc ttatggtgga aatatgggag aaaaatctga tcttggattt ggggatttgg   240
ataatttgtt gcctgaactt gccggctccg accagaccct tttccggtgt atctccggcg   300
atatggagga cccatcaatc agcttaaaac aattactaca aggaggaaat gaaaatgctg   360
atttgagttg tggagtttct gttcaaagct ctggttttga ggtctcagct gcaggttctt   420
tagctcatac agataatgtc tcttttttcta attcaaatct ccttctaaat gctaacattg   480
agaaaattgg atctgtcata aactcagaca caagcaaaaa tgttaacttt gaacacctca   540
atgtcaatct tttggcaaga aatttacctc ctgctttgag ttttcaagaa caacaatcag   600
aacagaattc tgcttatgtt aatatgttag gctcattatc ttatgatgta actcaagaac   660
agccccgcc caagcgccac aattccggta cgcttggttc aagcttaagc gcactattgc   720
ctgaggttcc atttttgac tccagtggtg agttattgct gaggaaacaa ccattgggac   780
aaacgcggca gcaagtcaat tttctgcctt ttcaccagtt tcagcaaaaa ccattaattg   840
tacctaagct tgaggcagct gttggtggtg ctaatggtaa tttgatggtt ccttgtcatc   900
aacagcagga acaacagttt atttatgacc agatttttca ggcctctgaa ttattactgg   960
ccggacaatt ctcaaacgcg caaatgatat ggcgcggct caatcaacag ctctctcccc  1020
ttggcaaacc cttcaagagg tctgcttttt acttcaaaga ggctctgcta ttgcctttcc  1080
ttttgccttg tacatccaca tcttttccac caagaattcc cacgccattt gattgtgtgc  1140
ttaagatgga tgcttataag gccttttctg aaatatctcc acttattcag ttcatgaatt  1200
tcacctccaa tcaacctatt cttgaagctc ttggggatgc caaggaaatt cacataatag  1260
attttgacat tggctgtggt gctcaatggt cctcatttat gcaagaactc cggagcagca  1320
```

-continued

```
atagaaaggc aacttctcta aagattactg cctttgtatc tccttcaacc caccactccg      1380
ttgagattgg catcatgcac gagagtttaa cgctgtttgc taatgatgtg ggaatcagat      1440
ttgagctgga agttattaac ttggattcct ttgaccctaa gcttatccc ttatcctcct       1500 tgaggtcatc tgagtgtgag gctattgcta ttaatttccc catctggtct atttcaagtt     1560
gtctatttgc atttccttca cttcttcact gtatgaagca gctttcacca aaagttgttg     1620
tatcattgga acgtggatgt gaacgtactg aactcccctt aaagcatcac ctcctccacg     1680
ccctccaata ttatgagata ctcttagcca gtattgatgc tgctaattta actccagaaa    1740
ttgggaaaaa aattgagagg tctcttctcc agcctagcat tgagaacacg gtcttggggc    1800
gcctccgatc ccctgatcga atgccccgt ggagaaacct atttgcttct gcaggatttt     1860
cacctattga atttagtaat atggctgaaa ttcaggctga atgtgttgtt aagaaactc      1920 aggtaggagg atttcacgtt gagaagcgcc agatgtcgct tgtgctatgc tggaaacagc    1980
aggagctctt gtcaattttg gcttggaggt gctgaggagc tttatctaat gaaagccaga    2040
agactctttc catttaacag caacatttcc tagaggtttt gactcttcaa tttgatagtc    2100
tgttcaaaat ttaatctaca ttgctatcac ctccactatt gcctgtaaat tcttttggt     2160 acatctaatt ctccatatgt agtcttgact gtaggcaagc attcctacgt gtaaacaga     2219

<210> SEQ ID NO 8
<211> LENGTH: 2284
<212> TYPE: DNA
<213> ORGANISM: Nicotiana tabacum

<400> SEQUENCE: 8
ctatgttcag atgattgtaa tacctcaaag ttttcctaaa ttctaacgcc taacaggggt       60
cgttggtgtt tctggttttg tgcataattt cttcttcacc agaagcacca atttgcaata      120
aagattcaaa ctttacaaga aattgaactt ttttctatgt tggttacgac aagtcacagt      180
ccttcagctt cagcttcctc atgctcttat ggtggaaata tggcagaaaa atctgatctt      240
ggatttgggg atttggataa tttgttgcct gaacttgccg gctccgacca gaccccttttc     300 cggtgtatct ccggcgatat ggaggaccca tcagtcagct tgaaacagtt actccaagga      360
ggaaatgcaa atgctgattt gggttgtgga gtttctgttc aaagctctgg ttttgaggtc      420
tcagctgcag gttctttagc tcatacagat aatgtctctt tttctaattc aaatctcctt      480
ctaaatgcta acattgagaa aattggatct gtcataaact cagacaacaa gcaaaatgtt     540
aattttgaac acctgaatgt caatcttttg gcaagaaatt tacctcctgc tttgagcttt    600
caagaacaac catcagaaca gaattctgct tatgttaaca tgttaggctc attatcatat     660
gatataagtc aagaacagcc cccgcccaaa cgccacaatt cgggtacgct tggttcaagc    720
ttaagtgctc tattgcctga agttccattt tttgactcca gtggtgactt attgctgagg    780
aaacaaccat tgggacaaat gcggcagcaa gtcaattttc tgccttttca ccagtttcag    840
caaaagccat taattgtacc taagcttgag gcagctggtg gtggtggtaa tggtaatttg     900
atagtgcctc gtcatcaaca gcaggaacaa caatttattt atgaccagtt ttttcaggcc    960
tctgaattat tactggccgg acaattctca aacgcgcaaa tgatattggc gcggctcaat   1020
caacagctct ctcccattgg caaacccttc aagaggtctg cttttttactt caaagaggct  1080 ctgcagttac ctttccttt gcttgtaca tccacatctt ttccaccaag aattcccacc      1140
ccatttgatt gtgtgcttaa gatggatgct tataaggcct tttctgaaat atctccactt    1200
```

```
atccagttca tgaatttcac ctccaatcaa cctattcttg aagctcttgg ggatgccaag    1260
caaattcaca taatagattt tgacattggc tgtggtgctc aatggtcctc atttatgcaa    1320
gaactccgga gcagcaatag aaaggcaact tctctaaaga ttactgcctt tgtatctcct    1380
tcaacccacc actccgttga gattggcatc atgcacgaaa gtttaacgct gtttgctaat    1440
gatgtgggaa tcagatttga gctggaagtt attaacttgg attcctttga ccctaagact    1500
tatcccttat cctccttgag gtcatctgag tgtgaggcta ttgctattaa tttccccatc    1560
tggtctattt caagttgtct atttgcattt ccttcacttc ttcactgtat gaagcagctt    1620
tcaccgaaag ttgttgtatc attggaacgt ggatgtgaac gtactgaact ccccttaaag    1680
catcacctcc tccatgccct ccaatattat gagatactct tagccagtat tgatgctgct    1740
aatttaactc cagagattgg gaaaaaaatt gagaggtctc ttctccagcc tagcattgag    1800
aacatggtct tggggcgcct ccgatcccct gatcgaatgc ccccgtggag aaacctattt    1860
gcttctgcag gattttcacc tattgaattt agtaatatgg ctgaaattca ggctgaatgt    1920
gttgttaaga gaactcaggt aggaggattt cacgtcgaga gcgccagac gtcgcttgtg    1980 ctatgctgga agcagcagga gctcttgtca attttggctt ggaggtgctg aggagcttta    2040
tctaatgaaa gccagaagac tctttccatt taacagctac atttcctaga ggttttgact    2100
cttcaatttg atagtctgtt caaaatttaa tctacattgc tatcacctcc actgttgcct    2160
gtaaattctt tttggtacat ctaattctcc atatgtagtc ttgactgtag caagcattc    2220 ctacgtgtaa acagaatctt aaccactttc cctgtttgaa atctgcgta gtatctttca    2280 gcat                                                                2284

<210> SEQ ID NO 9
<211> LENGTH: 2347
<212> TYPE: DNA
<213> ORGANISM: Nicotiana tabacum

<400> SEQUENCE: 9
ttcagatgat tgtaatacct caaagtaata acctagcagg agcaaaaggg gtacttggtg      60
tttcaggtta tgtaccttca atttcttctt caccagaagc agcaatttgt aataaaggtt     120
taaactttac aagaaacgaa tctgtctcag tgttggatgc aagaagtcct agtccttcag     180
cttcatcttc ctcgtgttct tatggtggac aatatgctgg aaataatgga gttcccggcg     240
ccggagctgg aaaaattgac ggccggaaag aggagttggt tactgagctg cagccatttt     300
catttgagtt ggagccagaa aaatttaatc ttggatttgg ggatttggat aatttgttgc     360
cggaacttgc cggctccgac cagaccattt tccggtggat ctccggcgat atggaggacc     420
catcagttag cttgaaacaa ctactccaag gaggaaatgc aaatgctgat ttgggttgtg     480
gagtttcagt tgcaggttct tttgcttgta ctgataatat ttccttttct agttcagata     540
tttctttaga tgccaacatt gagaaaattg gttctgttgt cattgactca ataatagac     600 caaataataa ctttgaaaat ccgaatgtca atctttggc caagagttta cctcctactt     660
tgagctttca cgaacaacaa tcagaagaga agcctcaaat ttcttgtcca caaataatga     720
caaaccaaca ccagttccag aattccgctt atgttaactt gtttggctca tcatcataca     780
acatgaatca agaacagccg ccacccaagc gccacaattc gggtatcctg ggttcaagct     840 taggcttttct attgcctaaa gttccgttct ttaatcccag tggtgactta ttgctgagga     900
aacaaccatt gggacatatg cagcaacaag tcaatttgct gcctcctcac cagtttcagc     960
caacatcatt atttgtacct aagcttgagg cagctggtgg tgatggtaat ggtaatttga    1020
```

```
tggtgcctcg tcatcaacag caggaacaac agttcattta tgaccagatt tttcaggcct    1080
ctgaattatt actggccgga catttctcaa acgcgcaaat gatattggcg cggctcaatc    1140
aacagctctc tcccattggc aaaccctcca agagggctgc ttttacttc aaagaggctc     1200 tgcagttacc tttcctttg ccttgtacat ccacatcttt tccaccaaga attcccaccc     1260
catttgattg tgtgcttaag atggatgctt ataaggcttt ttctgaagta tctccactta    1320
ttcagttcat gaatttcacc tccaatcaag ctattcttga agctcttggg gatgccaagc    1380
aaattcacat aatagatttt gacattggct gtggtgctca atggtcctca tttatgcaag    1440
aactcccgag cagcaataga aaggcaactt ctctaaagat tactgccttt gtatctcctt    1500
caacccacca ctccgttgag attggcatca tgcacgaaag tttaacgctg tttgctaatg    1560
atgtgggaat cagatttgag ctggaagtta ttaacttgga ttcctttgac cctaagactt    1620
atcccttatc ctccttgagg tcatctgagt gtgaggctat tgctattaat ttccccatct    1680
ggtctatttc aagttgtcta tttgcatttc cttcacttct tcactgtatg aagcagcttt    1740
caccaaaagt tgttgtatca ttggaacgtg gatgtgaacg tactgaactc cccttaaagc    1800
atcacctcct ccacgccctc caatattatg agatactttt agccagtatc gatgctgcta    1860
atttaacacc agacgttggg aaaaaaattg agaggtctct cctccagtct agcattgaga    1920
acatggtctt agggcgcctc cgatccccta accgaattcc cccatggaga aacctatttg    1980
cttctgcagg attttcacct gttgcgttta gtaatctaac tgaaatccag gcagaatgcc    2040
ttgttaagag aactcaggta ggaggatttc atgtcgagaa cgccagacg tcacttgtgc     2100 tatgctggaa gcagcaggaa ctcttgtcag ctttgtcttg gaggtgctga ggagctttat    2160
cttatgatga ctctttcttt taacaacaac atttactaga ggttttgact cttcaatttg    2220
atgtctgtta aaaaatctgc ttacatttgc tatgtcattt tctccttatg tgtagtcttt    2280
gactgtaggc aggccttccg cgttaaacaa atcttaacta ttatccctgt ttaaatatca    2340
gtgtgtt                                                              2347
```

<210> SEQ ID NO 10
<211> LENGTH: 2313
<212> TYPE: DNA
<213> ORGANISM: Nicotiana tabacum

<400> SEQUENCE: 10

```
tttgtagtgg gtttagctga tttttttct atgttcagat gattgtaata cctcaaagta     60
acaacctagc agtagcaaaa ggagtacttg gtgtttcaag ttatgtacct tcaatttctt    120
cttcaacaga agcaccaatt tgcaataaag gtttaacctt tacaagaaat gaatctgtct    180
cagtgttgga tacaagaagt cctagtcctt cagcttcatc ttcctcatgc tcttatggtg    240
gccaacatgc tggaaataat ggagttcccg cgccggagc tggaaaaatt gacggccgga     300
aagaggagtt ggtgactgag ctgcagccat tttcatttgg gttggagcca gaaaaattta    360
atcttggatt tggggatttg gataatttgt tgccggaact tgccggctcc gaccagacca    420
tttttcggtg gatctccggc gatatggagg acccatcagt cagcttgaaa caattactcc    480
aaggaggaaa tgcaaatgct gatttgggtg gtggagtttc agtggcaggt tcttttgctt    540
gtactgataa tatttccttt tctagttcag atatttcttt agatgccaac attgagaaaa    600
ttggttatgc tgtcatagac tcaaacaaca gaccaaataa taactttgaa atctgaatg     660 ccaatctttt ggccaagagt ttaccccctg ctttgagctt tcaagaacaa caatcagaag    720
```

```
agaagcctca aatttcttgt ccacaaatag tggcaaacca aacccagttc cagaattccg    780
cttatgttaa cttgtttggc tcatcatcat acaacatgaa tcaagaacag ccgccaccca    840
agcgccacaa ttcgggtatc ctgggttcaa gcttaggctt tctattgcct aaagttccgt    900
tctttagtcc cagtggtgac ttattgctga ggaaacaacc attgggacaa atgcagcaac    960
aagtcaattt gctgcctcct caccagtttc agccaacgcc attatttgta cctaagcttg   1020
aggcagctgg tggtggtggt aatggtaatt tggtggtgcc tcgtcatcaa cagcaggaac   1080
aacagttcat ttatgaccag attttttcagg cctctgaatt attactggcc ggacatttct   1140
caaacgcgca aatgatattg gcgcggctca atcaacagct ctctcccatt ggcaaaccct   1200
tcaagagggc tgcttttttac ttcaaagagg ctctgcagtt acctttcctt ttgccttgta   1260
catccacatc ttttccacca agaattccca ccccatttga ttgtgtgctt aagatggatg   1320
cttataaggc tttttctgaa gtatctccac ttattcagtt catgaatttc acctccaatc   1380
aagctattct tgaagctctt ggggctgcca agcaaattca cataatagat tttgacattg   1440
gctgtggtgc tcaatggtcc tcattaatgc aagaactccc gagcagcaat agaaaggcaa   1500
cttccctaaa gattactgcc tttgtatctc cttcaaccca ccactccgtt gagattggca   1560
tcatgcacga aagtttaacg ctgtttgcta atgatgtggg aatcagattt gagctggaag   1620
ttattaactt ggattccttt gaccctaaga cttatccctt atcctccttg aggtcatctg   1680
agtgtgaggc tattgctatt aatttttccca tatggtctat ttcaagttgt ctatttgcat   1740
ttccttcact gcttcactgc atgaagcaac tttcaccaaa agttgttgta tcattggaac   1800
gtggatgcga acgtactgaa ctccccttaa agcatcacct cctccacgcc ctccaatatt   1860
atgagatact tttagccagt attgatgctg ctaatttaac accagatgtt gggaaaaaaa   1920
ttgagaggtc tctcttccag tctagcattg agaacatggt cttagggcgc ctccgatccc   1980
ctgaccgaat tcccccatgg agaaacctat ttgcttctgc aggattttca cctgttgcgt   2040
ttagtaatct aactgaaatc caggcagaat gccttgttaa gagaactcag gtaggaggat   2100
ttcatgtcga gaagcgccag tcgtctcttg tgctatgctg gaagcagcgg gaactcttgt   2160
cagctttgtc ttggaggtgc tgaggagctt tatcttatga agccagacaa ctcttctttt   2220
taacagcaac atttactaga ggttttgact cttcaatttg atgtctgtta aaaaatctgc   2280
ttacatttgc tatgtcattt tctccgtatg tgt   2313
```

<210> SEQ ID NO 11
<211> LENGTH: 2531
<212> TYPE: DNA
<213> ORGANISM: Nicotiana tabacum

<400> SEQUENCE: 11

```
agaaagaagt cattttgtgg actgcttgac cttagatgga catcttcagt ttcaagcaaa     60 tattttttc tttgcacatt ttctaggtga tatcttttga tttgaggcca aaacttttgt    120
gggtatacat tagatgaagg ggatgcccct acccctttgat tttgagggga aggggggtgtt    180 agacttagac gttgtgttaa ataaaaatag catcttgaat tcttggaact acaatagcaa    240
agaaagttgt tatcttgtaa atagtccaag tgctgtactg gatatcataa ggagtccaag    300
gcctgttact tcttcttcaa ccctgtcttc atctttgggt ggtggtggtg gtggtggagg    360
tggcactgct tccacagata cggcaggtgc agtttctgca aacccatctt ctaaatggca    420
gcagcagcag caacaacaag acaacaccac tgccaccagt tccaatgtag gaggagctgc    480
tgctgaatct gagtttcaac aagttgctgc tgcttctgct gctgctacag aagggaagaa    540
```

```
atgtgctatg gaggagtggg aaggtgggtt atcagagtct gtaatggctt ctccttgtca    600
agaacagtct atacttgggt ggataatggg tgatgtagat gacccctcca tgtctaactt    660
gaacaaggtg ttgcaggtta gtggccctat ggactatgaa ttcaatgcag gatttggggt    720
tgtggatcaa ggttttggtg ttgaccaaat tggtactagt agtttcatgc ctgcaattaa    780
caactcttcc gtttcaagtt ttcctcctac ttctacaagg atgaacaatg acaagattgg    840
cttgttttct aacataccaa caaatctctc tcaaaatcca atctttcctt cattctctaa    900
caatcttggc ccagtttcct tcagccagac acaacagcag ccatttgaga gcacagattt    960
aaagcctcag agtttccatt cacatttctt gattaaccag caccaaacac agattcctca   1020
gaacccatca tttcttttgc cattgccatt tgcacagcag gagcaaaatc ttgtcttgcc   1080
accaaaggca aaaaggcaca accccgggac ccttgaacaa cagggctctc agatctccca   1140
agaactgttt atagatgcag acaacagcag gccaacacca tcccatcagc tccagctgct   1200
tccccatttt aggccaggag taccaatagg aacaaagcca aagatggtgg gggaagaaat   1260
ggggcagttt catcaactac aactacagca gcaacaacaa caagcaatta ttgaccagct   1320
attcaaagct gcagagctgg tccagacagg gaatccagta ctcgcgcaag ggatattggc   1380
gcggctcaat caccagctct ctccaattgg taagcctttc tatagggctg ctttttattg   1440
caaggaagct ttacaattgc tacttcatac caacaccaac aacttgaaca accccctcta t   1500 accatcttct tcacctttta atctcatctt caagattggt gcctataagt ccttctctga   1560
gatctcacca gttgcacagt ttgctaattt cacttgtaac caagccctgc ttgaggtctt   1620
ggatgggttt gaaagaattc atattgttga ttttgatatc ggctatggca ggcaatgggc   1680
ttctcttatg caagagcttg ccttgagaag tggtggcgca cctaccctga aaataactgc   1740
attggcctca ccctccacac atgaccaact agagcttgga ctcactagag aaagtttgat   1800 ccatttttgct aacgaaatca acatggaatt tgagtttgag attttaagca ttgattcttt   1860
gaattcaacg tcgtggtcac tgcctcctct agtctcagag aatgaggcaa ttgctgtcaa   1920
tcttcctatt agctcgcttg cgagctatca gctgtcgctc ccattggttc ttcgtttcgt   1980
gaagcagctg tcacctagga ttgtggtttc tgtggacaaa ggttgtgacc ggactgatct   2040
accatttcca aaccatgtaa ttcaaatcct tcagtcgtac tcaaaccttc ttgagtcgtt   2100
agatgccgta aatgtgaact ttgatgccct tcaaaagatt gaaagattct tgctccaacc   2160
aagaattgag agaattgtaa tgagtcgatt tcgttcccct gaaaagacgc agcattggag   2220
ggcactgttt ttgtcatctg gactctcccc gttacctttc agcaattttta cagaatcaca   2280 ggcagagtgt gtggtgaaga gaactcctgt tcggggtttc catgtagaga agaggcagtc   2340
ttcgcttgtt ctctgctggc agcgaaagga gctcatctca gcttcagctt ggaggtgctg   2400
aggaaaagca attaaatttg cagttgccaa ccaaccaagg tgctgcactg ttttagtatc   2460 tgaacccttta tgtttttgtt gcccgcaatt ttcatttgct aattttttctt gtggcatagg   2520 cagattgttt c                                                        2531
```

<210> SEQ ID NO 12
<211> LENGTH: 2680
<212> TYPE: DNA
<213> ORGANISM: Nicotiana tabacum

<400> SEQUENCE: 12

```
ataaggccaa caacaagaac agaagaaaag aaaatagcta tttagcaaca ttcttattat     60
```

```
catcaaaaaa cattttacca ctctccacaa tcttggctta gctaatttgt cttattctcc    120
aagaagaaga agaagaagaa gaagaagaag aagtacaaaa gaagcatcaa agaagaaaga    180
agtcattttg tggactgtat gattgtacat gaatgagttt ttctcttgtg gggtgtcctt    240
agatggacat cttcagttcc aatcaaaaac aatttctttg cacattttct aggtgatatc    300
ttttgatttg aggccaaaac ttttgtgggt atactttaga tgaaggggat gcccttaccc    360
tttgattttg agggaaggg ggtgttagac ttggacgttg tgttaaataa aaatagtatc     420
ttcaattctt ggaactacaa tagcaaagaa agttgttatc ttgtaaatag tccaagtgct    480
gtactggata ttataaggag tccaaggcct gttacttcct cttcaaccct gtcttcgtct    540
tttggtggtg gtggtggtgg tggtggcact gcttccacag atacggcagg cgcagtttct    600
gcaaacccat cttctaaatg gcagcagcag caacaacaag acaacaccac tgccaccagt    660
tccaatgtag gaggagctgc tgctgaatct gagcttctac aagttgctgc tgctacagaa    720
gggaagaaat gtggtatgga ggagtgggaa ggtgggttat cagagtctgt aatggcttct    780
ccttgtcaag aacagtctat acttgggtgg ataatgggcg atgtagatga cacctccatg    840
tctaacttga acaaggtgtt gcaggttagt ggccctatgg actatgaatt caatgcagga    900
tttggggttg tggatcaagg ttttggtgtt gatcaaattg gtactagtag tttcatgcct    960
gcaattaata gctcttctgt ttcaagtttt cctcctacta ctaccagaat gaacagtgac    1020
aagattggct tgctttctaa cataccaaca catctccctc aaaatccaat ctttccttca    1080
ttctctaaca atcttggccc agtttccttc agtcagacac agcagcagca gccatttgag    1140
agcacagatt tgaagcctca gagtttccac tcacagttct tgattgacca gcaccaaaca    1200
cagattcctc agaacccatc atttcttttg ccattgccat ttgcacagca ggagcaaaat    1260
cttgtcttgc caccaaaggc gaaaaggcac aaccccggga cccttgaaca gccgggctct    1320
cagatctccc aaggactgtt tatagatgca ggagaacagc aaccaacacc atcccatcag    1380
ctccagctgc ttccccattt taggccagga ggaccaatag gaacaaagcc aaagatggtg    1440
ggggaagaaa tggggcagtt tcatcaacta caactacagc agcagcagca gcaacagcaa    1500
caacaagcaa ttattgacca gctattcaaa gctgcagagc tggtccagac agggaatcca    1560
gtactcgcgc aagggatatt ggcgcggctc aatcaccagc tctctccaat tggtaagcct    1620
ttctataggg ctgcttttta ttgcaaggag gctttacaat tgctacttca taccaacacc    1680
aacaacttga acaaccccctc tataccatct tcttcacctt ttagtctcat cttcaagatt    1740
ggtgcctata agtccttctc tgagatctca ccagttgcac agtttgctaa tttcacttgt    1800
aaccaagccc tgcttgaggt cttggatggg tttgaaagaa ttcatattgt tgattttgat    1860
atcggctatg gcaggcaatg ggcttctctt atgcaagagc ttgccttgag aagtggtggc    1920
gcacctaccc tgaaaataac tgcattggcc tcaccctcca cacatgacca actagagctt    1980
ggactcacta gagaaagttt gatccatttt gctaacgaaa ttaacatgga attcgagttt    2040 gagatttta gcattgattc tttgaattca acgtcgtggt cactgcctcc tctagtctca    2100
gagaatgagg caattgctgt caatcttcct gttagctcgc tttcgagcta tcagctgtcg    2160
ctcccattgg ttcttggttt cgtgaagcag ttgtcgccta ggattgttgt ttctgtggac    2220
aaaggttgtg atcggactga cctaccattt ccaaaccatg taattcaagt ccttcagtcg    2280
tactcaaacc ttcttgagtc gttagatgcc gtaaatgtga attttgatgc actccaaaag    2340
attgaaaggt tcttgctcca accaagaatt gagagaactg taatgggacg ttttcgttcc    2400
cctgaaaagg cgcagcattg gagggcactg ttttttgtcat ccggactctc cccattacct    2460
```

```
ttcagcaatt ttgcagaatc acaggcagag tgtgtggtga agagaactcc tgttcggggt    2520
tttcacgtgg agaagaggca gtcttcgctt gttctctgct ggcaacgaaa ggagctcata    2580
tctgcttcag cttggaggtg ctgaggaaaa gaaattaaat ttgcagttgc caaccaacca    2640
taaaaatgaa ggtgctgcaa agtcactttt tttaagtatc                         2680

<210> SEQ ID NO 13
<211> LENGTH: 2219
<212> TYPE: DNA
<213> ORGANISM: Nicotiana tabacum

<400> SEQUENCE: 13
acctcaatgt attcctaaat cctaacacct aaaggggttg ttggtgtttc tggttttgtg      60 cctaattttat tcttcaccag aagcaccaat ttgcaattaa tattcaaact ttacaagaaa    120
ttgaacttgt ttctatgttg gttacgacaa gtcacagtcc ttcagcttca gcttcatctt    180
cctcatgctc ttatggtgga aatatgggag aaaaatctga tcttggattt ggggattgg     240 ataatttgtt gcctgaactt gccggctccg accagaccct tttccggtgt atctccggcg    300
atatggagga cccatcaatc agcttaaaac aattactaca aggaggaaat gaaaatgctg    360
atttgagttg tggagtttct gttcaaagct ctggttttga ggtctcagct gcaggttctt    420
tagctcatac agataatgtc tcttttttcta attcaaatct ccttctaaat gctaacattg    480
agaaaattgg atctgtcata aactcagaca acaagcaaaa tgttaacttt gaacacctca    540
atgtcaatct tttggcaaga aatttacctc ctgctttgag ttttcaagaa caacaatcag    600
aacagaattc tgcttatgtt aatatgttag gctcattatc ttatgatgta actcaagaac    660
agcccccgcc caagcgccac aattccggta cgcttggttc aagcttaagc gcactattgc    720
ctgaggttcc attttttgac tccagtggtg agttattgct gaggaaacaa ccattgggac    780
aaacgcggca gcaagtcaat tttctgcctt ttcaccagtt tcagcaaaaa ccattaattg    840
tacctaagct tgaggcagct gttggtggtg ctaatggtaa tttgatggtt ccttgtcatc    900
aacagcagga acaacagttt atttatgacc agattttttca ggcctctgaa ttattactgg    960
ccggacaatt ctcaaacgcg caaatgatat tggcgcggct caatcaacag ctctctcccc   1020
ttggcaaacc cttcaagagg tctgcttttt acttcaaaga ggctctgcta ttgccttttcc   1080 ttttgccttg tacatccaca tcttttccac caagaattcc cacgccattt gattgtgtgc   1140
ttaagatgga tgcttataag gccttttctg aaatatctcc acttattcag ttcatgaatt   1200
tcacctccaa tcaacctatt cttgaagctc ttggggatgc caaggaaatt cacataatag   1260
attttgacat tggctgtggt gctcaatggt cctcatttat gcaagaactc cggagcagca   1320
atagaaaggc aacttctcta agattactg cctttgtatc tccttcaacc caccactccg    1380
ttgagattgg catcatgcac gagagtttaa cgctgtttgc taatgatgtg ggaatcagat   1440
ttgagctgga agttattaac ttggattcct ttgaccctaa gacttatccc ttatcctcct   1500
tgaggtcatc tgagtgtgag gctattgcta ttaatttccc catctggtct atttcaagtt   1560
gtctatttgc atttccttca cttcttcact gtatgaagca gctttcacca aaagttgttg   1620
tatcattgga acgtggatgt gaacgtactg aactccccctt aaagcatcac ctcctccacg   1680
ccctccaata ttatgagata ctcttagcca gtattgatgc tgctaattta actccagaaa   1740
ttgggaaaaa aattgagagg tctcttctcc agcctagcat tgagaacacg gtcttggggc   1800
gcctccgatc ccctgatcga atgcccccgt ggagaaacct atttgcttct gcaggatttt   1860
```

```
cacctattga atttagtaat atggctgaaa ttcaggctga atgtgttgtt aagagaactc    1920
aggtaggagg atttcacgtt gagaagcgcc agatgtcgct tgtgctatgc tggaaacagc    1980
aggagctctt gtcaattttg gcttggaggt gctgaggagc tttatctaat gaaagccaga    2040
agactctttc catttaacag caacatttcc tagaggtttt gactcttcaa tttgatagtc    2100
tgttcaaaat ttaatctaca ttgctatcac ctccactatt gcctgtaaat tcttttttggt   2160 acatctaatt ctccatatgt agtcttgact gtaggcaagc attcctacgt gtaaacaga     2219
```

<210> SEQ ID NO 14
<211> LENGTH: 2284
<212> TYPE: DNA
<213> ORGANISM: Nicotiana tabacum

<400> SEQUENCE: 14

```
ctatgttcag atgattgtaa tacctcaaag ttttcctaaa ttctaacgcc taacaggggt      60
cgttggtgtt tctggttttg tgcataattt cttcttcacc agaagcacca atttgcaata     120
aagattcaaa cttacaagaa aattgaactt ttttctatgt tggttacgac aagtcacagt     180
ccttcagctt cagcttcctc atgctcttat ggtggaaata tggcagaaaa atctgatctt     240
ggatttgggg atttggataa tttgttgcct gaacttgccg gctccgacca gaccttttc      300 cggtgtatct ccggcgatat ggaggaccca tcagtcagct tgaaacagtt actccaagga     360
ggaaatgcaa atgctgattt gggttgtgga gtttctgttc aaagctctgg ttttgaggtc     420
tcagctgcag gttctttagc tcatacagat aatgtctctt tttctaattc aaatctcctt     480
ctaaatgcta acattgagaa aattggatct gtcataaact cagacaacaa gcaaaatgtt     540 aatttttgaac acctgaatgt caatctttg gcaagaaatt tacctcctgc tttgagcttt     600
caagaacaac catcagaaca gaattctgct tatgttaaca tgttaggctc attatcatat     660
gatataagtc aagaacagcc cccgcccaaa cgccacaatt cgggtacgct tggttcaagc     720
ttaagtgctc tattgcctga agttccattt tttgactcca gtggtgactt attgctgagg     780
aaacaaccat tgggacaaat gcggcagcaa gtcaattttc tgccttttca ccagtttcag     840
caaaagccat taattgtacc taagcttgag gcagctggtg gtggtggtaa tggtaatttg     900
atagtgcctc gtcatcaaca gcaggaacaa caatttattt atgaccagtt ttttcaggcc     960
tctgaattat tactggccgg acaattctca acgcgcaaa tgatattggc gcggctcaat    1020
caacagctct ctcccattgg caaacccttc aagaggtctg cttttttactt caaagaggct    1080 ctgcagttac ctttccttttt gccttgtaca tccacatctt ttccaccaag aattcccacc    1140
ccatttgatt gtgtgcttaa gatggatgct tataaggcct tttctgaaat atctccactt    1200
atccagttca tgaatttcac ctccaatcaa cctattcttg aagctcttgg ggatgccaag    1260
caaattcaca taatagattt tgacattggc tgtggtgctc aatggtcctc atttatgcaa    1320
gaactccgga gcagcaatag aaaggcaact tctctaaaga ttactgcctt tgtatctcct    1380
tcaacccacc actccgttga gattggcatc atgcacgaaa gtttaacgct gtttgctaat    1440
gatgtgggaa tcagatttga gctggaagtt attaacttgg attccttttga ccctaagact    1500 tatcccttat cctccttgag gtcatctgag tgtgaggcta ttgctattaa tttcccccatc    1560 tggtctattt caagttgtct atttgcattt ccttcacttc ttcactgtat gaagcagctt    1620
tcaccgaaag ttgttgtatc attggaacgt ggatgtgaac gtactgaact ccccttaaag    1680
catcacctcc tccatgccct ccaatattat gagatactct tagccagtat tgatgctgct    1740
aatttaactc cagagattgg gaaaaaaatt gagaggtctc ttctccagcc tagcattgag    1800
```

```
aacatggtct tggggcgcct ccgatcccct gatcgaatgc ccccgtggag aaacctattt    1860
gcttctgcag gattttcacc tattgaattt agtaatatgg ctgaaattca ggctgaatgt    1920
gttgttaaga gaactcaggt aggaggattt cacgtcgaga agcgccagac gtcgcttgtg    1980
ctatgctgga agcagcagga gctcttgtca attttggctt ggaggtgctg aggagcttta    2040
tctaatgaaa gccagaagac tctttccatt taacagctac atttcctaga ggttttgact    2100
cttcaatttg atagtctgtt caaaatttaa tctacattgc tatcacctcc actgttgcct    2160
gtaaattctt tttggtacat ctaattctcc atatgtagtc ttgactgtag gcaagcattc    2220
ctacgtgtaa acagaatctt aaccactttc cctgtttgaa atctgcgta gtatctttca    2280 gcat                                                                 2284

<210> SEQ ID NO 15
<211> LENGTH: 2347
<212> TYPE: DNA
<213> ORGANISM: Nicotiana tabacum

<400> SEQUENCE: 15
ttcagatgat tgtaatacct caaagtaata acctagcagg agcaaaaggg gtacttggtg      60
tttcaggtta tgtaccttca atttcttctt caccagaagc agcaatttgt aataaaggtt     120
taaactttac aagaaacgaa tctgtctcag tgttggatgc aagaagtcct agtccttcag     180
cttcatcttc ctcgtgttct tatggtggac aatatgctgg aaataatgga gttcccggcg     240
ccggagctgg aaaaattgac ggccggaaag aggagttggt tactgagctg cagccatttt     300
catttgagtt ggagccagaa aaatttaatc ttggatttgg ggatttggat aatttgttgc     360
cggaacttgc cggctccgac cagaccattt tccggtggat ctccggcgat atggaggacc     420
catcagttag cttgaaacaa ctactccaag gaggaaatgc aaatgctgat tgggttgtg      480 gagtttcagt tgcaggttct tttgcttgta ctgataatat ttccttttct agttcagata     540
tttctttaga tgccaacatt gagaaaattg gttctgttgt cattgactca aataatagac     600
caaataataa ctttgaaaat ccgaatgtca atcttttggc caagagttta cctcctactt     660
tgagctttca cgaacaacaa tcagaagaga agcctcaaat ttcttgtcca caaataatga     720
caaaccaaca ccagttccag aattccgctt atgttaactt gtttggctca tcatcataca     780
acatgaatca agaacagccg ccacccaagc gccacaattc gggtatcctg ggttcaagct     840
taggctttct attgcctaaa gttccgttct ttaatcccag tggtgactta ttgctgagga     900
aacaaccatt gggacatatg cagcaacaag tcaatttgct gcctcctcac cagtttcagc     960
caacatcatt atttgtacct aagcttgagg cagctggtgg tgatggtaat ggtaatttga    1020
tggtgcctcg tcatcaacag caggaacaac agttcattta tgaccagatt tttcaggcct    1080
ctgaattatt actggccgga catttctcaa acgcgcaaat gatattggcg cggctcaatc    1140
aacagctctc tcccattggc aaaccccttca agagggctgc ttttttacttc aaagaggctc    1200 tgcagttacc tttccttttg ccttgtacat ccacatcttt tccaccaaga attcccaccc    1260
catttgattg tgtgcttaag atggatgctt ataggctttt tctgaagta tctccactta    1320 ttcagttcat gaatttcacc tccaatcaag ctattcttga agctcttggg gatgccaagc    1380
aaattcacat aatagatttt gacattggct gtggtgctca atggtcctca tttatgcaag    1440
aactcccgag cagcaataga aaggcaactt ctctaaagat tactgccttt gtatctcctt    1500
caacccacca ctccgttgag attggcatca tgcacgaaag tttaacgctg tttgctaatg    1560
```

```
atgtgggaat cagatttgag ctggaagtta ttaacttgga ttcctttgac cctaagactt    1620
atcccttatc ctccttgagg tcatctgagt gtgaggctat tgctattaat ttccccatct    1680
ggtctatttc aagttgtcta tttgcatttc cttcacttct tcactgtatg aagcagcttt    1740
caccaaaagt tgttgtatca ttggaacgtg atgtgaacg tactgaactc cccttaaagc     1800
atcacctcct ccacgccctc caatattatg agatacttt agccagtatc gatgctgcta     1860
atttaacacc agacgttggg aaaaaaattg agaggtctct cctccagtct agcattgaga    1920
acatggtctt agggcgcctc cgatcccta accgaattcc cccatggaga aacctatttg     1980
cttctgcagg attttcacct gttgcgttta gtaatctaac tgaaatccag cagaatgcc    2040 ttgttaagag aactcaggta ggaggatttc atgtcgagaa gcgccagacg tcacttgtgc    2100
tatgctggaa gcagcaggaa ctcttgtcag ctttgtcttg gaggtgctga ggagctttat    2160
cttatgatga ctctttcttt taacaacaac atttactaga ggttttgact cttcaatttg    2220
atgtctgtta aaaaatctgc ttacatttgc tatgtcattt tctccttatg tgtagtcttt    2280
gactgtaggc aggccttccg cgttaaacaa atcttaacta ttatccctgt ttaaatatca    2340
gtgtgtt                                                              2347

<210> SEQ ID NO 16
<211> LENGTH: 2313
<212> TYPE: DNA
<213> ORGANISM: Nicotiana tabacum

<400> SEQUENCE: 16
tttgtagtgg gtttagctga tttttttct atgttcagat gattgtaata cctcaaagta      60
acaacctagc agtagcaaaa ggagtacttg gtgtttcaag ttatgtacct tcaatttctt    120
cttcaacaga agcaccaatt tgcaataaag gtttaacctt acaagaaat gaatctgtct     180 cagtgttgga tacaagaagt cctagtcctt cagcttcatc ttcctcatgc tcttatggtg    240
gccaacatgt tggaaataat ggagttcccg gcgccggagc tggaaaaatt gacgccgga    300 aagaggagtt ggtgactgag ctgcagccat tttcatttgg gttggagcca gaaaaattta    360
atcttggatt tggggatttg gataaattgt tgccggaact tgccggctcc gaccagacca    420 ttttcggtg gatctccggc gatatggagg acccatcagt cagcttgaaa caattactcc    480
aaggaggaaa tgcaaatgct gatttgggtg gtggagtttc agtggcaggt tcttttgctt    540
gtactgataa tatttccttt tctagttcag atatttcttt agatgccaac attgagaaaa    600
ttggttatgc tgtcatagac tcaaacaaca gaccaaataa taactttgaa atctgaatg    660 ccaatcttt ggccaagagt ttaccccctg ctttgagctt tcaagaacaa caatcagaag    720
agaagcctca aatttcttgt ccacaaatag tggcaaacca aacccagttc cagaattccg    780
cttatgttaa cttgtttggc tcatcatcat acaacatgaa tcaagaacag ccgccaccca    840
agcgccacaa ttcgggtatc ctgggttcaa gcttaggctt ctattgcct aaagttccgt    900 tctttagtcc cagtggtgac ttattgctga ggaaacaacc attgggacaa atgcagcaac    960
aagtcaattt gctgcctcct caccagtttc agccaacgcc attatttgta cctaagcttg   1020
aggcagctgg tggtggtggt aatggtaatt tggtggtgcc tcgtcatcaa cagcaggaac   1080
aacagttcat ttatgaccag attttcagg cctctgaatt attactggcc ggacatttct    1140
caaacgcgca aatgatattg gcgcggctca atcaacagct ctctcccatt ggcaaaccct   1200
tcaagagggc tgcttttta cttcaagagg ctctgcagtt acctttcctt ttgccttgta    1260
catccacatc tttttccacca agaattccca ccccatttga ttgtgtgctt aagatggatg    1320
```

-continued

```
cttataaggc tttttctgaa gtatctccac ttattcagtt catgaatttc acctccaatc    1380
aagctattct tgaagctctt ggggctgcca agcaaattca cataatagat tttgacattg    1440
gctgtggtgc tcaatggtcc tcattaatgc aagaactccc gagcagcaat agaaaggcaa    1500
cttccctaaa gattactgcc tttgtatctc cttcaaccca ccactccgtt gagattggca    1560
tcatgcacga aagtttaacg ctgtttgcta atgatgtggg aatcagattt gagctggaag    1620
ttattaactt ggattccttt gaccctaaga cttatccctt atcctccttg aggtcatctg    1680
agtgtgaggc tattgctatt aattttccca tatggtctat ttcaagttgt ctatttgcat    1740
ttccttcact gcttcactgc atgaagcaac tttcaccaaa agttgttgta tcattggaac    1800
gtggatgcga acgtactgaa ctccccttaa agcatcacct cctccacgcc ctccaatatt    1860
atgagatact tttagccagt attgatgctg ctaatttaac accagatgtt gggaaaaaaa    1920
ttgagaggtc tctcttccag tctagcattg agaacatggt cttagggcgc ctccgatccc    1980
ctgaccgaat tcccccatgg agaaacctat ttgcttctgc aggattttca cctgttgcgt    2040
ttagtaatct aactgaaatc caggcagaat gccttgttaa gagaactcag gtaggaggat    2100
ttcatgtcga gaagcgccag tcgtctcttg tgctatgctg gaagcagcgg gaactcttgt    2160
cagctttgtc ttggaggtgc tgaggagctt tatcttatga agccagacaa ctctttcttt    2220
taacagcaac atttactaga ggttttgact cttcaatttg atgtctgtta aaaaatctgc    2280
ttacatttgc tatgtcattt tctccgtatg tgt                                 2313

<210> SEQ ID NO 17
<211> LENGTH: 2550
<212> TYPE: DNA
<213> ORGANISM: Nicotiana tabacum

<400> SEQUENCE: 17
agaaagaagt cattttgtgg actgcttgac cttagatgga catcttcagt ttcaagcaaa      60
tatttttttc tttgcacatt ttctaggtga tatcttttga tttgaggcca aaacttttgt     120
gggtatacat tagatgaagg ggatgcccct acccttttgat tttgagggga aggggggtgtt    180 agacttagac gttgtgttaa ataaaaatag catcttgaat tcttggaact acaatagcaa     240
agaaagttgt tatcttgtaa atagtccaag tgctgtactg gatatcataa ggagtccaag     300
gcctgttact tcttcttcaa ccctgtcttc atctttgggt ggtggtggtg gtggtggagg     360
tggcactgct tccacagata cggcaggtgc agtttctgca aacccatctt ctaaatggca     420
gcagcagcag caacaacaag acaacaccac tgccaccagt tccaatgtag gaggagctgc     480
tgctgaatct gagtttcaac aagttgctgc tgcttctgct gctgctacag aagggaagaa     540
atgtgctatg gaggagtggg aaggtgggtt atcagagtct gtaatggctt ctccttgtca     600
agaacagtct atacttgggt ggataatggg tgatgtagat gacccctcca tgtctaactt     660
gaacaaggtg ttgcaggtta gtggccctat ggactatgaa ttcaatgcag gatttggggt     720
tgtggatcaa ggttttggtg ttgaccaaat tggtactagt agtttcatgc ctgcaattaa     780
caactcttcc gtttcaagtt ttcctcctac ttctacaagg atgaacaatg acaagattgg     840
cttgttttct aacataccaa caaatctctc tcaaaatcca atctttcctt cattctctaa     900
caatcttggc ccagtttcct tcagccagac acaacagcag ccatttgaga gcacagattt     960
aaagcctcag agtttccatt cacatttctt gattaaccag caccaaacac agattcctca    1020
gaacccatca tttcttttgc cattgccatt tgcacagcag gagcaaaatc ttgtcttgcc    1080
```

| | |
|---|---|
| accaaaggca aaaaggcaca acccgggac ccttgaacaa cagggctctc agatctccca | 1140 |
| agaactgttt atagatgcag gacaacagca gccaacacca tcccatcagc tccagctgct | 1200 |
| tccccatttt aggccaggag taccaatagg aacaaagcca agatggtgg gggaagaaat | 1260 |
| ggggcagttt catcaactac aactacagca gcaacaacaa caagcaatta ttgaccagct | 1320 |
| attcaaagct gcagagctgg tccagacagg gaatccagta ctcgcgcaag ggatattggc | 1380 |
| gcggctcaat caccagctct ctccaattgg taagcctttc tatagggctg cttttttattg | 1440 |
| caaggaagct ttacaattgc tacttcatac caacaccaac aacttgaaca cccctctat | 1500 |
| accatcttct tcaccttta atctcatctt caagattggt gcctataagt ccttctctga | 1560 |
| gatctcacca gttgcacagt ttgctaattt cacttgtaac caagccctgc ttgaggtctt | 1620 |
| ggatgggttt gaaagaattc atattgttga ttttgatatc ggctatggca ggcaatgggc | 1680 |
| ttctcttatg caagagcttg ccttgagaag tggtggcgca cctaccctga aataactgc | 1740 |
| attggcctca ccctccacac atgaccaact agagcttgga ctcactagag aaagtttgat | 1800 |
| ccattttgct aacgaaatca acatggaatt tgagtttgag attttaagca ttgattcttt | 1860 |
| gaattcaacg tcgtggtcac tgcctcctct agtctcagag aatgaggcaa ttgctgtcaa | 1920 |
| tcttcctatt agctcgcttg cgagctatca gctgtcgctc ccattggttc ttcgtttcgt | 1980 |
| gaagcagctg tcacctagga ttgtggttc tgtggacaaa ggttgtgacc ggactgatct | 2040 |
| accatttcca aaccatgtaa ttcaaatcct tcagtcgtac tcaaaccttc ttgagtcgtt | 2100 |
| agatgccgta aatgtgaact ttgatgccct tcaaaagatt gaaagattct tgctccaacc | 2160 |
| aagaattgag agaattgtaa tgagtcgatt tcgttcccct gaaaagacgc agcattggag | 2220 |
| ggcactgttt ttgtcatctg gactctcccc gttacctttc agcaattta cagaatcaca | 2280 |
| ggcagagtgt gtggtgaaga gaactcctgt tcgggggttc catgtagaga agaggcagtc | 2340 |
| ttcgcttgtt ctctgctggc agcgaaagga gctcatctca gcttcagctt ggaggtgctg | 2400 |
| aggaaaagca attaaatttg cagttgccaa ccaaccaagg tgctgcactg ttttagtatc | 2460 |
| tgaaccttta tgttttgtt gcccgcaatt ttcatttgct aattttttctt gtggcatagg | 2520 |
| cagattgttt cggtgaacaa tccaacattc | 2550 |

<210> SEQ ID NO 18
<211> LENGTH: 2584
<212> TYPE: DNA
<213> ORGANISM: Nicotiana tabacum

<400> SEQUENCE: 18

| | |
|---|---|
| agaaagaagt cattttgtgg actgtatgat tgtacatgaa tgagttttc tcttgtgggg | 60 |
| tgtccttaga tggacatctt cagttccaat caaaaacaat ttctttgcac attttctagg | 120 |
| tgatatcttt tgatttgagg ccaaaacttt tgtgggtata ctttagatga aggggatgcc | 180 |
| cttacccttt gattttgagg ggaaggggt gttagacttg gacgttgtgt taaataaaaa | 240 |
| tagtatcttc aattcttgga actacaatag caaagaaagt tgttatcttg taaatagtcc | 300 |
| aagtgctgta ctggatatta taaggagtcc aaggcctgtt acttcctctt caaccctgtc | 360 |
| ttcgtctttt ggtggtggtg gtggtggtgg tggcactgct tccacagata cggcaggcgc | 420 |
| agtttctgca aacccatctt ctaaatggca gcagcagcaa caacaagaca caccactgc | 480 |
| caccagttcc aatgtaggag gagctgctgc tgaatctgag cttctacaag ttgctgctgc | 540 |
| tacagaaggg aagaaatgtg gtatggagga gtgggaaggt gggttatcag agtctgtaat | 600 |
| ggcttctcct tgtcaagaac agtctatact tgggtggata atgggcgatg tagatgacac | 660 |

```
ctccatgtct aacttgaaca aggtgttgca ggttagtggc cctatggact atgaattcaa    720
tgcaggattt ggggttgtgg atcaaggttt tggtgttgat caaattggta ctagtagttt    780
catgcctgca attaatagct cttctgtttc aagttttcct cctactacta ccagaatgaa    840
cagtgacaag attggcttgc tttctaacat accaacacat ctccctcaaa atccaatctt    900
tccttcattc tctaacaatc ttggcccagt ttccttcagt cagacacagc agcagcagcc    960
atttgagagc acagatttga agcctcagag tttccactca cagttcttga ttgaccagca   1020
ccaaacacag attcctcaga acccatcatt tcttttgcca ttgccatttg cacagcagga   1080
gcaaaatctt gtcttgccac aaaggcgaaa aaggcacaac cccgggaccc ttgaacagcc   1140
gggctctcag atctcccaag gactgtttat agatgcagga aacagcaac caacaccatc    1200 ccatcagctc cagctgcttc cccatttag gccaggagga ccaataggaa caaagccaaa    1260
gatggtgggg gaagaaatgg ggcagtttca tcaactacaa ctacagcagc agcagcagca   1320
acagcaacaa caagcaatta ttgaccagct attcaaagct gcagagctgg tccagacagg   1380
gaatccagta ctcgcgcaag ggatattggc gcggctcaat caccagctct ctccaattgg   1440 taagccttc tatagggctg cttttattg caaggaggct ttacaattgc tacttcatac     1500
caacaccaac aacttgaaca acccctctat accatcttct tcacctttta gtctcatctt    1560
caagattggt gcctataagt ccttctctga gatctcacca gttgcacagt ttgctaattt    1620
cacttgtaac caagccctgc ttgaggtctt ggatgggttt gaaagaattc atattgttga    1680
ttttgatatc ggctatggca ggcaatgggc ttctcttatg caagagcttg ccttgagaag    1740
tggtggcgca cctaccctga aataactgc attggcctca ccctccacac atgaccaact     1800
agagcttgga ctcactagag aaagtttgat ccatttgct aacgaaatta acatggaatt     1860
cgagtttgag attttaagca ttgattcttt gaattcaacg tcgtggtcac tgcctcctct    1920
agtctcagag aatgaggcaa ttgctgtcaa tcttcctgtt agctcgcttt cgagctatca    1980
gctgtcgctc ccattggttc ttggtttcgt gaagcagttg tcgcctagga ttgttgtttc    2040
tgtggacaaa ggttgtgatc ggactgacct accatttcca aaccatgtaa ttcaagtcct    2100
tcagtcgtac tcaaaccttc ttgagtcgtt agatgccgta aatgtgaatt ttgatgcact    2160
ccaaaagatt gaaaggttct tgctccaacc aagaattgag agaactgtaa tgggacgttt    2220
tcgttcccct gaaaaggcgc agcattggag ggcactgttt tgtcatccg gactctcccc     2280 attacctttc agcaattttg cagaatcaca ggcagagtgt gtggtgaaga gaactcctgt    2340
tcggggtttt cacgtggaga agaggcagtc ttcgcttgtt ctctgctggc aacgaaagga    2400
gctcatatct gcttcagctt ggaggtgctg aggaaaagaa attaaatttg cagttgccaa    2460
ccaaccataa aaatgaaggt gctgcaaagt cactttttt aagtatctga acctttcaat     2520
tttcacttgc taattttct tgtggcatag gcagattgtt tcggtgttat aagaacaatc     2580
aaac                                                                2584
```

<210> SEQ ID NO 19
<211> LENGTH: 26
<212> TYPE: DNA
<213> ORGANISM: Artificial Sequence
<220> FEATURE:
<223> OTHER INFORMATION: synthetic primer

<400> SEQUENCE: 19

```
acccatccaa gacctcaagc agggct                                          26
```

<210> SEQ ID NO 20
<211> LENGTH: 21
<212> TYPE: DNA
<213> ORGANISM: Artificial Sequence
<220> FEATURE:
<223> OTHER INFORMATION: synthetic primer

<400> SEQUENCE: 20
tgattgagcc gcgccaatat c                                        21

<210> SEQ ID NO 21
<211> LENGTH: 29
<212> TYPE: DNA
<213> ORGANISM: Artificial Sequence
<220> FEATURE:
<223> OTHER INFORMATION: synthetic primer

<400> SEQUENCE: 21
ggccttataa gcatccatct taagcacac                                29

<210> SEQ ID NO 22
<211> LENGTH: 24
<212> TYPE: DNA
<213> ORGANISM: Artificial Sequence
<220> FEATURE:
<223> OTHER INFORMATION: synthetic primer

<400> SEQUENCE: 22
agaaagaagt cattttgtgg actg                                     24

<210> SEQ ID NO 23
<211> LENGTH: 20
<212> TYPE: DNA
<213> ORGANISM: Artificial Sequence
<220> FEATURE:
<223> OTHER INFORMATION: synthetic primer

<400> SEQUENCE: 23
gaatgttgga ttgttcaccg                                          20

<210> SEQ ID NO 24
<211> LENGTH: 24
<212> TYPE: DNA
<213> ORGANISM: Artificial Sequence
<220> FEATURE:
<223> OTHER INFORMATION: synthetic primer

<400> SEQUENCE: 24
gtttgattgt tcttataaca ccga                                     24

<210> SEQ ID NO 25
<211> LENGTH: 27
<212> TYPE: DNA
<213> ORGANISM: Artificial Sequence
<220> FEATURE:
<223> OTHER INFORMATION: synthetic primer

<400> SEQUENCE: 25
ctatgttcag atgattgtaa tacctca                                  27

<210> SEQ ID NO 26
<211> LENGTH: 22
<212> TYPE: DNA
<213> ORGANISM: Artificial Sequence
<220> FEATURE:
<223> OTHER INFORMATION: synthetic primer

<400> SEQUENCE: 26
acacataagg agaaaatgac gc                                      22

<210> SEQ ID NO 27
<211> LENGTH: 26
<212> TYPE: DNA
<213> ORGANISM: Artificial Sequence
<220> FEATURE:
<223> OTHER INFORMATION: synthetic primer

<400> SEQUENCE: 27
ttcagatgat tgtaatacct caaagt                                  26

<210> SEQ ID NO 28
<211> LENGTH: 24
<212> TYPE: DNA
<213> ORGANISM: Artificial Sequence
<220> FEATURE:
<223> OTHER INFORMATION: synthetic primer

<400> SEQUENCE: 28
aacacactga tatttaaaca ggga                                    24

<210> SEQ ID NO 29
<211> LENGTH: 23
<212> TYPE: DNA
<213> ORGANISM: Artificial Sequence
<220> FEATURE:
<223> OTHER INFORMATION: synthetic primer

<400> SEQUENCE: 29
tttgtagtgg gtttagctga ttt                                     23

<210> SEQ ID NO 30
<211> LENGTH: 24
<212> TYPE: DNA
<213> ORGANISM: Artificial Sequence
<220> FEATURE:
<223> OTHER INFORMATION: synthetic primer

<400> SEQUENCE: 30
acacatacgg agaaaatgac atag                                    24

<210> SEQ ID NO 31
<211> LENGTH: 22
<212> TYPE: DNA
<213> ORGANISM: Artificial Sequence
<220> FEATURE:
<223> OTHER INFORMATION: synthetic primer

<400> SEQUENCE: 31
acaggcaata gtggaggtga ta                                      22

<210> SEQ ID NO 32
<211> LENGTH: 26
<212> TYPE: DNA
<213> ORGANISM: Artificial Sequence
<220> FEATURE:
<223> OTHER INFORMATION: synthetic primer

<400> SEQUENCE: 32
acctcaatgt attcctaaat cctaac                                  26

<210> SEQ ID NO 33

<211> LENGTH: 23
<212> TYPE: DNA
<213> ORGANISM: Artificial Sequence
<220> FEATURE:
<223> OTHER INFORMATION: synthetic primer

<400> SEQUENCE: 33
tctgtttaca cgtaggaatg ctt                                          23

<210> SEQ ID NO 34
<211> LENGTH: 26
<212> TYPE: DNA
<213> ORGANISM: Artificial Sequence
<220> FEATURE:
<223> OTHER INFORMATION: synthetic primer

<400> SEQUENCE: 34
ctatgttcag atgattgtaa tacctc                                       26

<210> SEQ ID NO 35
<211> LENGTH: 24
<212> TYPE: DNA
<213> ORGANISM: Artificial Sequence
<220> FEATURE:
<223> OTHER INFORMATION: synthetic primer

<400> SEQUENCE: 35
atgctgaaag atactacgca gatt                                         24

<210> SEQ ID NO 36
<211> LENGTH: 23
<212> TYPE: DNA
<213> ORGANISM: Artificial Sequence
<220> FEATURE:
<223> OTHER INFORMATION: synthetic primer

<400> SEQUENCE: 36
cacctccaat caagctattc ttg                                          23

<210> SEQ ID NO 37
<211> LENGTH: 24
<212> TYPE: DNA
<213> ORGANISM: Artificial Sequence
<220> FEATURE:
<223> OTHER INFORMATION: synthetic primer

<400> SEQUENCE: 37
gtatctcata atattggagg gcgt                                         24

<210> SEQ ID NO 38
<211> LENGTH: 22
<212> TYPE: DNA
<213> ORGANISM: Artificial Sequence
<220> FEATURE:
<223> OTHER INFORMATION: synthetic primer

<400> SEQUENCE: 38
caccagctat tcaaagctgc ag                                           22

<210> SEQ ID NO 39
<211> LENGTH: 25
<212> TYPE: DNA
<213> ORGANISM: Artificial Sequence
<220> FEATURE:
<223> OTHER INFORMATION: synthetic primer

<400> SEQUENCE: 39

```
aactttctct agtgagtcca agctc                                            25

<210> SEQ ID NO 40
<211> LENGTH: 23
<212> TYPE: DNA
<213> ORGANISM: Artificial Sequence
<220> FEATURE:
<223> OTHER INFORMATION: synthetic primer

<400> SEQUENCE: 40 caccccctagc aggagcaaaa ggg                                             23

<210> SEQ ID NO 41
<211> LENGTH: 20
<212> TYPE: DNA
<213> ORGANISM: Artificial Sequence
<220> FEATURE:
<223> OTHER INFORMATION: synthetic primer

<400> SEQUENCE: 41
atggctgcag ctcagtaacc                                                  20

<210> SEQ ID NO 42
<211> LENGTH: 500
<212> TYPE: DNA
<213> ORGANISM: Artificial Sequence
<220> FEATURE:
<223> OTHER INFORMATION: Syntetic

<400> SEQUENCE: 42
cacctccaat caagctattc ttgaagctct tggggatgcc aagcaaattc acataataga      60
ttttgacatt ggctgtggtg ctcaatggtc ctcatttatg caagaactcc cgagcagcaa     120
tagaaaggca acttctctaa agattactgc ctttgtatct ccttcaaccc accactccgt     180
tgagattggc atcatgcacg aaagtttaac gctgtttgct aatgatgtgg gaatcagatt     240
tgagctggaa gttattaact tggattcctt tgacccctaag acttatccct tatcctcctt     300
gaggtcatct gagtgtgagg ctattgctat taatttcccc atctggtcta tttcaagttg     360
tctatttgca tttccttcac ttcttcactg tatgaagcag ctttcaccaa aagttgttgt     420
atcattggaa cgtggatgtg aacgtactga actccccctta aagcatcacc tcctccacgc     480
cctccaatat tatgagatac                                                  500

<210> SEQ ID NO 43
<211> LENGTH: 484
<212> TYPE: DNA
<213> ORGANISM: Artificial Sequence
<220> FEATURE:
<223> OTHER INFORMATION: Synthetic

<400> SEQUENCE: 43
caccagctat tcaaagctgc agagctggtc cagacaggga atccagtact cgcgcaaggg      60
atattggcgc ggctcaatca ccagctctct ccaattggta agcctttcta tagggctgct     120
ttttattgca aggaagcttt acaattgcta cttcatacca acaccaacaa cttgaacaac     180
ccctctatac catcttcttc acctttaat ctcatcttca agattggtgc ctataagtcc     240
ttctctgaga tctcaccagt tgcacagttt gctaatttca cttgtaacca agccctgctt     300
gaggtcttgg atgggtttga aagaattcat attgttgatt ttgatatcgg ctatggcagg     360
caatgggctt ctcttatgca agagcttgcc ttgagaagtg gtggcgcacc taccctgaaa     420
```

```
ataactgcat tggcctcacc ctccacacat gaccaactag agcttggact cactagagaa    480
agtt                                                                484
```

<210> SEQ ID NO 44
<211> LENGTH: 270
<212> TYPE: DNA
<213> ORGANISM: Artificial Sequence
<220> FEATURE:
<223> OTHER INFORMATION: Synthetic

<400> SEQUENCE: 44

```
cacccctagc aggagcaaaa ggggtacttg gtgtttcagg ttatgtacct tcaatttctt     60
cttcaccaga agcagcaatt tgtaataaag gtttaaactt tacaagaaac gaatctgtct    120
cagtgttgga tgcaagaagt cctagtcctt cagcttcatc ttcctcgtgt tcttatggtg    180
gacaatatgc tggaaataat ggagttcccg gcgccggagc tggaaaaatt gacggccgga    240
aagaggagtt ggttactgag ctgcagccat                                    270
```

<210> SEQ ID NO 45
<211> LENGTH: 19
<212> TYPE: DNA
<213> ORGANISM: Artificial Sequence
<220> FEATURE:
<223> OTHER INFORMATION: synthetic primer

<400> SEQUENCE: 45

```
cgagaagcgc cagacgtca                                                 19
```

<210> SEQ ID NO 46
<211> LENGTH: 27
<212> TYPE: DNA
<213> ORGANISM: Artificial Sequence
<220> FEATURE:
<223> OTHER INFORMATION: synthetic primer

<400> SEQUENCE: 46

```
tgttgttgtt aaagaaaga gtcatca                                         27
```

<210> SEQ ID NO 47
<211> LENGTH: 30
<212> TYPE: DNA
<213> ORGANISM: Artificial Sequence
<220> FEATURE:
<223> OTHER INFORMATION: synthetic probe

<400> SEQUENCE: 47

```
agcagcagga actcttgtca gctttgtctt                                     30
```

<210> SEQ ID NO 48
<211> LENGTH: 23
<212> TYPE: DNA
<213> ORGANISM: Artificial Sequence
<220> FEATURE:
<223> OTHER INFORMATION: synthetic primer

<400> SEQUENCE: 48

```
cccatcagtt agcttgaaac aac                                            23
```

<210> SEQ ID NO 49
<211> LENGTH: 26
<212> TYPE: DNA
<213> ORGANISM: Artificial Sequence
<220> FEATURE:
<223> OTHER INFORMATION: synthetic primer

```
<400> SEQUENCE: 49
ttatttgagt caatgacaac agaacc                                          26

<210> SEQ ID NO 50
<211> LENGTH: 30
<212> TYPE: DNA
<213> ORGANISM: Artificial Sequence
<220> FEATURE:
<223> OTHER INFORMATION: synthetic probe

<400> SEQUENCE: 50
aagaacctgc aactgaaact ccacaaccca                                      30

<210> SEQ ID NO 51
<211> LENGTH: 22
<212> TYPE: DNA
<213> ORGANISM: Artificial Sequence
<220> FEATURE:
<223> OTHER INFORMATION: synthetic primer

<400> SEQUENCE: 51
cccatcagtc agcttgaaac aa                                              22

<210> SEQ ID NO 52
<211> LENGTH: 25
<212> TYPE: DNA
<213> ORGANISM: Artificial Sequence
<220> FEATURE:
<223> OTHER INFORMATION: synthetic primer

<400> SEQUENCE: 52
tgtttgagtc tatgacagca taacc                                           25

<210> SEQ ID NO 53
<211> LENGTH: 28
<212> TYPE: DNA
<213> ORGANISM: Artificial Sequence
<220> FEATURE:
<223> OTHER INFORMATION: synthetic probe

<400> SEQUENCE: 53
agaacctgcc actgaaactc caccaccc                                        28

<210> SEQ ID NO 54
<211> LENGTH: 22
<212> TYPE: DNA
<213> ORGANISM: Artificial Sequence
<220> FEATURE:
<223> OTHER INFORMATION: synthetic primer

<400> SEQUENCE: 54
cttaagcgca ctattgcctg ag                                              22

<210> SEQ ID NO 55
<211> LENGTH: 26
<212> TYPE: DNA
<213> ORGANISM: Artificial Sequence
<220> FEATURE:
<223> OTHER INFORMATION: synthetic primer

<400> SEQUENCE: 55
cctcaagctt aggtacaatt aatggt                                          26

<210> SEQ ID NO 56
```

```
<211> LENGTH: 24
<212> TYPE: DNA
<213> ORGANISM: Artificial Sequence
<220> FEATURE:
<223> OTHER INFORMATION: synthetic probe

<400> SEQUENCE: 56
cttgctgccg cgtttgtccc aatg                                           24

<210> SEQ ID NO 57
<211> LENGTH: 23
<212> TYPE: DNA
<213> ORGANISM: Artificial Sequence
<220> FEATURE:
<223> OTHER INFORMATION: synthetic primer

<400> SEQUENCE: 57
gcttaagtgc tctattgcct gaa                                            23

<210> SEQ ID NO 58
<211> LENGTH: 25
<212> TYPE: DNA
<213> ORGANISM: Artificial Sequence
<220> FEATURE:
<223> OTHER INFORMATION: synthetic primer

<400> SEQUENCE: 58
tcaagcttag gtacaattaa tggct                                          25

<210> SEQ ID NO 59
<211> LENGTH: 25
<212> TYPE: DNA
<213> ORGANISM: Artificial Sequence
<220> FEATURE:
<223> OTHER INFORMATION: synthetic probe

<400> SEQUENCE: 59
cttgctgccg catttgtccc aatgg                                          25

<210> SEQ ID NO 60
<211> LENGTH: 27
<212> TYPE: DNA
<213> ORGANISM: Artificial Sequence
<220> FEATURE:
<223> OTHER INFORMATION: synthetic primer

<400> SEQUENCE: 60
ctaccatttc caaccatgt aattcaa                                         27

<210> SEQ ID NO 61
<211> LENGTH: 22
<212> TYPE: DNA
<213> ORGANISM: Artificial Sequence
<220> FEATURE:
<223> OTHER INFORMATION: synthetic primer

<400> SEQUENCE: 61
ctctcaattc ttggttggag ca                                             22

<210> SEQ ID NO 62
<211> LENGTH: 30
<212> TYPE: DNA
<213> ORGANISM: Artificial Sequence
<220> FEATURE:
<223> OTHER INFORMATION: synthetic probe

<400> SEQUENCE: 62
```
ctcaaacctt cttgagtcgt tagatgccgt                                30

<210> SEQ ID NO 63
<211> LENGTH: 427
<212> TYPE: DNA
<213> ORGANISM: Artificial Sequence
<220> FEATURE:
<223> OTHER INFORMATION: Synthetic

<400> SEQUENCE: 63
aattggtacc agaaatctca aaattccggc agaacaattt tgaatctcga tccgtagaaa    60
cgagacggtc attgttttag ttccaccacg attatatttg aaatttacgt gagtgtgagt   120
gagacttgca taagaaaata aaatctttag ttgggaaaaa attcaataat ataaatgggc   180
ttgagaagga agcgagggat aggccttttt ctaaaatagg cccatttaag ctattaacaa   240
tcttcaaaag taccacagcg cttaggtaaa gaaagcagct gagtttatat atggttagag   300
acgaagtagt gattgagctg gaaaaattga cggcgtttta gagctagaaa tagcaagtta   360
aaataaggct agtccgttat caacttgaaa aagtggcacc gagtcggtgc ttttttttgga  420
tccaatt                                                            427

<210> SEQ ID NO 64
<211> LENGTH: 427
<212> TYPE: DNA
<213> ORGANISM: Artificial Sequence
<220> FEATURE:
<223> OTHER INFORMATION: Synthetic

<400> SEQUENCE: 64
aattggtacc agaaatctca aaattccggc agaacaattt tgaatctcga tccgtagaaa    60
cgagacggtc attgttttag ttccaccacg attatatttg aaatttacgt gagtgtgagt   120
gagacttgca taagaaaata aaatctttag ttgggaaaaa attcaataat ataaatgggc   180
ttgagaagga agcgagggat aggccttttt ctaaaatagg cccatttaag ctattaacaa   240
tcttcaaaag taccacagcg cttaggtaaa gaaagcagct gagtttatat atggttagag   300
acgaagtagt gattggtttt gaggtctcag ctgcgtttta gagctagaaa tagcaagtta   360
aaataaggct agtccgttat caacttgaaa aagtggcacc gagtcggtgc ttttttttgga  420
tccaatt                                                            427

<210> SEQ ID NO 65
<211> LENGTH: 427
<212> TYPE: DNA
<213> ORGANISM: Artificial Sequence
<220> FEATURE:
<223> OTHER INFORMATION: Synthetic

<400> SEQUENCE: 65
aattggtacc agaaatctca aaattccggc agaacaattt tgaatctcga tccgtagaaa    60
cgagacggtc attgttttag ttccaccacg attatatttg aaatttacgt gagtgtgagt   120
gagacttgca taagaaaata aaatctttag ttgggaaaaa attcaataat ataaatgggc   180
ttgagaagga agcgagggat aggccttttt ctaaaatagg cccatttaag ctattaacaa   240
tcttcaaaag taccacagcg cttaggtaaa gaaagcagct gagtttatat atggttagag   300
acgaagtagt gattgcctct gaattattac tggcgtttta gagctagaaa tagcaagtta   360
aaataaggct agtccgttat caacttgaaa aagtggcacc gagtcggtgc ttttttttgga  420 tccaatt                                                           427

<210> SEQ ID NO 66
<211> LENGTH: 4452
<212> TYPE: DNA
<213> ORGANISM: Artificial Sequence
<220> FEATURE:
<223> OTHER INFORMATION: Synthetic Cas 9

<400> SEQUENCE: 66

```
catatggatt acaaggatga tgatgataag gattacaagg atgatgatga taagatggct    60
ccaaagaaga agagaaaggt tggaatccac ggagttccag ctgctgataa gaagtactct   120
atcggacttg acatcggaac caactctgtt ggatgggctg ttatcaccga tgagtacaag   180
gttccatcta agaagttcaa ggttcttgga aacaccgata gacactctat caagaagaac   240
cttatcggtg ctcttctttt cgattctgga gagaccgctg aggctaccag attgaagaga   300
accgctagaa gaagatacac cagaagaaag aacagaatct gctaccttca ggaaatcttc   360
tctaacgaga tggctaaggt tgatgattct ttcttccaca gacttgagga gtctttcctt   420
gttgaggagg ataagaagca cgagagacac ccaatcttcg gaaacatcgt tgatgaggtt   480
gcttaccacg agaagtaccc aaccatctac caccttagaa gaagttggt tgattctacc   540
gataaggctg atcttagact tatctacctt gctcttgctc acatgatcaa gttcagagga   600
cacttcctta tcgagggaga ccttaaccca gataactctg atgttgataa gttgttcatc   660
cagcttgttc agacctacaa ccagcttttc gaggagaacc caatcaacgc ttctggagtt   720
gatgctaagg ctatcctttc tgctagactt tctaagtctc gtagacttga gaaccttatc   780
gctcagcttc aggagagaa gaagaacgga cttttcggaa accttatcgc tctttctctt   840
ggacttaccc caaacttcaa gtctaacttc gatcttgctg aggatgctaa gttgcagctt   900
tctaaggata cctacgatga tgatcttgat aaccttcttg ctcagatcgg agatcagtac   960
gctgatcttt ccttgctgc taagaacctt tctgatgcta tccttctttc tgacatcctt  1020
agagttaaca ccgagatcac caaggctcca cttttctgctt ctatgatcaa gagatacgat  1080
gagcaccacc aggatcttac ccttttgaag gctcttgtta cagcagcagct tccagagaag  1140
tacaaggaaa tcttcttcga tcagtctaag aacggatacg ctggatacat cgatggagga  1200
gcttctcagg aggagttcta caagttcatc aagccaatcc ttgagaagat ggatggaacc  1260
gaggagcttc ttgttaagtt gaacagagag gatcttctta gaaagcagag aaccttcgat  1320
aacggatcta tcccacacca gatccacctt ggagagcttc acgctatcct tcgtagacag  1380
gaggatttct acccattctt gaaggataac agagagaaga tcgagaagat ccttaccttc  1440
agaatcccat actacgttgg accacttgct agggaaaact ctcgtttcgc ttggatgacc  1500
agaaagtctg aggagaccat caccccttgg aacttcgagg aggtaagttt ctgcttctac  1560
cttttgatata tatataataa ttatcattaa ttagtagtaa tataatattt caaatatttt  1620
tttcaaaata aaagaatgta gtatatagca attgcttttc tgtagtttat aagtgtgtat  1680
attttaatttt ataactttc taatatatga ccaaatttg ttgatgtgca ggttgttgat  1740
aagggagctt ctgctcagtc tttcatcgag agaatgacca acttcgataa gaaccttcca  1800
aacgagaagg ttcttccaaa gcactctctt ctttacgagt acttcaccgt ttacaacgag  1860
cttaccaagg ttaagtacgt taccgaggga atgagaaagc cagcttttcct ttctggagag  1920
cagaagaagg ctatcgttga tcttcttttc aagaccaaca gaaaggttac cgttaagcag  1980
ttgaaggagg attacttcaa gaagatcgag tgcttcgatt ctgttgaaat ctctggagtt  2040
```

```
gaggatagat tcaacgcttc tcttggaacc taccacgatc ttttgaagat catcaaggat   2100
aaggatttcc ttgataacga ggagaacgag gacatccttg aggacatcgt tcttacccct   2160
acccttttcg aggatagaga gatgatcgag gagagactca agacctacgc tcaccttttc   2220
gatgataagg ttatgaagca gttgaagaga gaaagataca ccggatgggg tagactttct   2280
cgtaagttga tcaacggaat cagagataag cagtctggaa agaccatcct tgatttcttg   2340
aagtctgatg gattcgctaa cagaaacttc atgcagctta ccacgatga ttctcttacc   2400 ttcaaggagg acatccagaa ggctcaggtt tctggacagg gagattctct tcacgagcac   2460
atcgctaacc ttgctggatc tccagctatc aagaagggaa tccttcagac cgttaaggtt   2520
gttgatgagc ttgttaaggt tatgggtaga cacaagccag agaacatcgt tatcgagatg   2580
gctagagaga accagaccac ccagaaggga cagaagaact ctcgtgagag aatgaagaga   2640
atcgaggagg gaatcaagga gcttggatct caaatcttga aggagcaccc agttgagaac   2700
acccagcttc agaacgagaa gttgtacctt tactaccttc agaacggaag agatatgtac   2760
gttgatcagg agcttgacat caacagactt tctgattacg atgttgatca catcgttcca   2820
cagtcttcct tgaaggatga ttctatcgat aacaaggttc ttacccgttc tgataagaac   2880
agaggaaagt ctgataacgt tccatctgag gaggttgtta agaagatgaa gaactactgg   2940
agacagcttc ttaacgctaa gttgatcacc cagagaaagt tcgataacct taccaaggct   3000
gagagaggag gactttctga gcttgataag gctggattca tcaagagaca gcttgttgag   3060
accagacaga tcaccaagca cgttgctcag atccttgatt ctcgtatgaa caccaagtac   3120
gatgagaacg ataagttgat cagagaggtt aaggttatca ccttgaagtc taagttggtt   3180
tctgatttca gaaggatt ccagttctac aaggttagag agatcaacaa ctaccaccac   3240
gctcacgatg cttaccttaa cgctgttgtt ggaaccgctc ttatcaagaa gtacccaaag   3300
ttggagtctg agttcgttta cggagattac aaggtttacg atgttagaaa gatgatcgct   3360
aagtctgagc aggagatcgg aaaggctacc gctaagtact tcttctactc taacatcatg   3420
aacttcttca agaccgagat cacccttgct aacggagaga tcagaaagag accacttatc   3480
gagaccaacg gagagaccgg agagatcgtt tgggataagg gaagagattt cgctaccgtt   3540
agaaaggttc tttctatgcc acaggttaac atcgttaaga aaccgaggt tcagaccgga   3600 ggattctcta aggagtctat ccttccaaag agaaactctg ataagttgat cgctagaaag   3660
aaggattggg acccaaagaa gtacggagga ttcgattctc caaccgttgc ttactctgtt   3720
cttgttgttg ctaaggttga aaggaaag tctaagaagt tgaagtctgt taaggagctt   3780
cttggaatca ccatcatgga gcgttcttct ttcgagaaga acccaatcga tttccttgag   3840
gctaagggat acaaggaggt taagaaggat cttatcatca gttgccaaa gtactctctt   3900 ttcgagcttg agaacggaag aaagagaatg cttgcttctg ctggagagct tcagaaggga   3960
aacgagcttg ctcttccatc taagtacgtt aacttccttt accttgcttc tcactacgag   4020
aagttgaagg gatctccaga ggataacgag cagaagcagc ttttcgttga gcagcacaag   4080
cactaccttg atgagatcat cgagcaaatc tctgagttct ctaagagagt tatccttgct   4140
gatgctaacc ttgataaggt tcttctctct tacaacaagc acagagataa gccaatcaga   4200
gagcaggctg agaacatcat ccacctttc accccttacca accttggtgc tccagctgct   4260
ttcaagtact cgataccac catcgataga aaaagataca cctctaccaa ggaggttctt   4320
gatgctaccc ttatccacca gtctatcacc ggactttacg agaccagaat cgatctttct   4380
```

```
cagcttggag gagataagag accagctgct accaagaagg ctggacaggc taagaagaag    4440
aagtgagtcg ac                                                         4452

<210> SEQ ID NO 67
<211> LENGTH: 19
<212> TYPE: DNA
<213> ORGANISM: Artificial Sequence
<220> FEATURE:
<223> OTHER INFORMATION: synthetic primer

<400> SEQUENCE: 67
cctagcagga gcaaaaggg                                                    19

<210> SEQ ID NO 68
<211> LENGTH: 26
<212> TYPE: DNA
<213> ORGANISM: Artificial Sequence
<220> FEATURE:
<223> OTHER INFORMATION: synthetic primer

<400> SEQUENCE: 68
tctattattt gagtcaatga caacag                                            26

<210> SEQ ID NO 69
<211> LENGTH: 22
<212> TYPE: DNA
<213> ORGANISM: Artificial Sequence
<220> FEATURE:
<223> OTHER INFORMATION: synthetic primer

<400> SEQUENCE: 69
caacctagca gtagcaaaag ga                                                22

<210> SEQ ID NO 70
<211> LENGTH: 26
<212> TYPE: DNA
<213> ORGANISM: Artificial Sequence
<220> FEATURE:
<223> OTHER INFORMATION: synthetic primer

<400> SEQUENCE: 70
tctgttgttt gagtctatga cagcat                                            26

<210> SEQ ID NO 71
<211> LENGTH: 34
<212> TYPE: DNA
<213> ORGANISM: Artificial Sequence
<220> FEATURE:
<223> OTHER INFORMATION: synthetic primer

<400> SEQUENCE: 71
acctcaatgt attcctaaat cctaacacct aaag                                   34

<210> SEQ ID NO 72
<211> LENGTH: 26
<212> TYPE: DNA
<213> ORGANISM: Artificial Sequence
<220> FEATURE:
<223> OTHER INFORMATION: synthetic primer

<400> SEQUENCE: 72
gggctgttct tgagttacat cataag                                            26

<210> SEQ ID NO 73
<211> LENGTH: 32
```

```
<212> TYPE: DNA
<213> ORGANISM: Artificial Sequence
<220> FEATURE:
<223> OTHER INFORMATION: synthetic primer

<400> SEQUENCE: 73
cctcaaagtt ttcctaaatt ctaacgccta ac                                   32

<210> SEQ ID NO 74
<211> LENGTH: 26
<212> TYPE: DNA
<213> ORGANISM: Artificial Sequence
<220> FEATURE:
<223> OTHER INFORMATION: synthetic primer

<400> SEQUENCE: 74
gggctgttct tgacttatat catatg                                          26

<210> SEQ ID NO 75
<211> LENGTH: 25
<212> TYPE: DNA
<213> ORGANISM: Artificial Sequence
<220> FEATURE:
<223> OTHER INFORMATION: synthetic primer

<400> SEQUENCE: 75
gtccacaaat aatgacaaac caaca                                           25

<210> SEQ ID NO 76
<211> LENGTH: 24
<212> TYPE: DNA
<213> ORGANISM: Artificial Sequence
<220> FEATURE:
<223> OTHER INFORMATION: synthetic primer

<400> SEQUENCE: 76
gaaagctgct tcatacgtga agaa                                            24

<210> SEQ ID NO 77
<211> LENGTH: 25
<212> TYPE: DNA
<213> ORGANISM: Artificial Sequence
<220> FEATURE:
<223> OTHER INFORMATION: synthetic primer

<400> SEQUENCE: 77
gtccacaaat agtggcaaac caaac                                           25

<210> SEQ ID NO 78
<211> LENGTH: 20
<212> TYPE: DNA
<213> ORGANISM: Artificial Sequence
<220> FEATURE:
<223> OTHER INFORMATION: synthetic primer

<400> SEQUENCE: 78
ctcctcagca cctccaagac                                                 20

<210> SEQ ID NO 79
<211> LENGTH: 30
<212> TYPE: DNA
<213> ORGANISM: Artificial Sequence
<220> FEATURE:
<223> OTHER INFORMATION: synthetic primer

<400> SEQUENCE: 79
```
tatgttaggc tcattatctt atgatgtaac                                                      30

<210> SEQ ID NO 80
<211> LENGTH: 21
<212> TYPE: DNA
<213> ORGANISM: Artificial Sequence
<220> FEATURE:
<223> OTHER INFORMATION: synthetic primer

<400> SEQUENCE: 80
ggcaaaagga aaggcaatag c                                                               21

<210> SEQ ID NO 81
<211> LENGTH: 30
<212> TYPE: DNA
<213> ORGANISM: Artificial Sequence
<220> FEATURE:
<223> OTHER INFORMATION: synthetic primer

<400> SEQUENCE: 81
catgttaggc tcattatcat atgatataag                                                      30

<210> SEQ ID NO 82
<211> LENGTH: 21
<212> TYPE: DNA
<213> ORGANISM: Artificial Sequence
<220> FEATURE:
<223> OTHER INFORMATION: synthetic primer

<400> SEQUENCE: 82
ggcaaaagga aaggtaactg c                                                               21

<210> SEQ ID NO 83
<211> LENGTH: 8
<212> TYPE: PRT
<213> ORGANISM: Nicotiana tabacum

<400> SEQUENCE: 83

Cys Arg Phe Phe Ser Ser Tyr Arg
1               5

<210> SEQ ID NO 84
<211> LENGTH: 58
<212> TYPE: PRT
<213> ORGANISM: Nicotiana tabacum

<400> SEQUENCE: 84

Met Ala Gly Lys Arg Ser Trp Leu Leu Ser Cys Ser His Phe His Leu
1               5                   10                  15

Ser Trp Ser Gln Lys Asn Leu Ile Leu Asp Leu Gly Ile Trp Ile Ile
            20                  25                  30

Cys Cys Arg Asn Leu Pro Ala Pro Thr Arg Pro Phe Ser Gly Gly Ser
        35                  40                  45

Pro Ala Ile Trp Arg Thr His Gln Leu Ala
    50                  55

<210> SEQ ID NO 85
<211> LENGTH: 18
<212> TYPE: PRT
<213> ORGANISM: Nicotiana tabacum

<400> SEQUENCE: 85

Asn Cys Val Asn Arg Leu Glu Ile Met Ser Ile Val Leu Ile Thr Tyr
1               5                   10                  15

Asn Leu

<210> SEQ ID NO 86
<211> LENGTH: 9
<212> TYPE: PRT
<213> ORGANISM: Nicotiana tabacum

<400> SEQUENCE: 86

Arg Pro Asp Ile Ser Gln Thr Arg Lys
1               5

<210> SEQ ID NO 87
<211> LENGTH: 57
<212> TYPE: PRT
<213> ORGANISM: Nicotiana tabacum

<400> SEQUENCE: 87

Gly Arg Thr Ile Leu Lys Arg Ala Asn Asp Ile Gly Ala Ala Gln Ser
1               5                   10                  15

Thr Ala Leu Ser Pro Trp Gln Thr Leu Gln Glu Val Cys Phe Leu Leu
            20                  25                  30

Gln Arg Gly Ser Ala Ile Ala Phe Pro Phe Ala Leu Tyr Ile His Ile
        35                  40                  45

Phe Ser Thr Lys Asn Ser His Ala Ile
    50                  55

<210> SEQ ID NO 88
<211> LENGTH: 9
<212> TYPE: PRT
<213> ORGANISM: Nicotiana tabacum

<400> SEQUENCE: 88

Arg Pro Asp Asn Ser Gln Thr Arg Lys
1               5

<210> SEQ ID NO 89
<211> LENGTH: 57
<212> TYPE: PRT
<213> ORGANISM: Nicotiana tabacum

<400> SEQUENCE: 89

Gly Arg Thr Phe Leu Lys Arg Ala Asn Asp Ile Gly Ala Ala Gln Ser
1               5                   10                  15

Thr Ala Leu Ser His Trp Gln Thr Leu Gln Glu Gly Cys Phe Leu Leu
            20                  25                  30

Gln Arg Gly Ser Ala Val Thr Phe Pro Phe Ala Leu Tyr Ile His Ile
        35                  40                  45

Phe Ser Thr Lys Asn Ser His Pro Ile
    50                  55

TOBACCO PLANT AND PRODUCTION METHOD THEREOF

CROSS-REFERENCE TO RELATED APPLICATIONS

This application is a Continuation of PCT International Application No. PCT/JP2017/032871 filed in Japan on Sep. 12, 2017, which claims the benefit of Patent Applications No. 2017-051976 filed in Japan on Mar. 16, 2017, the entire contents of which are hereby incorporated by reference.

TECHNICAL FIELD

The present invention relates to (i) a tobacco plant which is suitable for cultivation for harvesting leaf tobaccos, (ii) a method of obtaining the tobacco plant, (iii) a harvest from the tobacco plant, and (iv) a processed product of the harvest.

BACKGROUND ART

In the process of the growth of seed plants, embryos in seeds develop so as to form cotyledons and apical meristems (shoot apical meristems). Cell division of the apical meristem (shoot apical meristem) causes leaf primordia to be sequentially formed, and causes axillary meristems to be formed on an adaxial side of the leaf primordia. The axillary meristems then serve as apical meristems (shoot apical meristems) and result in axillary buds. During vegetative growth of a plant, usually, the development of axillary buds is temporarily in a dormant state (suppressed). In a case where apical meristems (shoot apical meristems) of a primary shoot is transitioned from a vegetative growth state to a reproductive growth state, or in a case where the apical meristems (shoot apical meristems) die, the development of the axillary buds is no longer in a dormant state and is promoted. With respect to the development of axillary buds, there are a plurality of research reports on solanaceous plants (e.g., tomatoes and tobaccos) and on other plants (e.g., rice and *Arabidopsis thaliana*).

A tobacco plant, which is cultivated for harvesting leaves, is subjected to topping (cutting off a stem of an apical portion with a flower) during cultivation, for the purpose of enhancing the quality and quantity of leaves to be harvested (e.g., for the purpose of accumulating composition of the leaves and maturing and expanding leaves). Topping causes axillary buds of the tobacco plant to start vigorously developing from, bases of leaves (leaf axil). The development of axillary buds naturally consumes nutrients, and therefore causes a relative decrease in nutrient which are supplied to leaves to be harvested. Therefore, the development and outgrowth of axillary buds leads to a decrease in quality and yield of leaves to be harvested. Therefore, in cultivating a tobacco plant for harvesting leaf tobaccos, axillary buds are subjected to, for example, control such as removal or developmental suppression.

Examples of a method of removing an axillary bud encompass a method in which an axillary bud is picked by hand or by machine. Picking an axillary bud by hand involves (i) a large amount of work (and accordingly an increase in labor costs) and (ii) a problem of low efficiency. Picking an axillary bud by machine is less accurate than picking by hand, and therefore brings a problem of damaging a plant. Examples of a method of suppressing the development of an axillary bud encompass a method in which an agrochemical is used. The use of agrochemicals involves problems such as repeated application for maintaining an effect, an impact on the growth of a plant, an impact on leaves to be harvested due to agrochemicals residue, and an increase in inspection cost for agrochemicals residue.

The following are disclosures of Non-Patent Literatures 1 through 4 concerning the development of axillary buds of plants other than tobacco plants.

It has been reported that in a mutant in which a mutation is introduced into HAIRLY MERISTRM (HAM) gene of *petunia*, trichomes are ectopically formed in shoot apical meristems (Non-Patent Literature 1). It has also been reported that LOST MERISTEMS (LOM), which is an orthologue of the HAM gene in *Arabidopsis thaliana*, is a causative gene of suppression of axillary bud formation in a mutant (Non-Patent Literature 2). In *Arabidopsis thaliana*, at least four genes are predicted as HAM homologues. When HAM1 and other HAM homologues (2 or 3 homologues) are mutated simultaneously, an increase in the number of mutations caused axillary bud formation to be suppressed more greatly than in the case of mutation of HAM1 only (Non-Patent Literatures 2 and 3). As a homologue of HAM gene of pepper, one kind has been reported. The mutation of such a gene caused the formation of axillary buds to be completely suppressed (Non-Patent Literature 4).

CITATION LIST

Non-Patent Literature

Non-Patent Literature 1

Stuurman J, Jaggi F, Kuhlemeier C. (2002) Shoot meristem maintenance is controlled by a GRAS-gene mediated signal from differentiating cells. Genes & Development 16: 2213-2218.

Non-Patent Literature 2

Schulze S, Schafer B N, Parizotto E A, Voinnet O, Theres K. (2010) LOST MERISTEMS genes regulate cell differentiation of central zone descendants in *Arabidopsis* shoot meristems The Plant Journal 64(4): 668-678.

Non-Patent Literature 3

Engstrom E M, Andersen C M, Gumulak-Smith J, Hu J, Orlova E, Sozzani R, Bowman J L. (2011) *Arabidopsis* homologs of the *petunia* hairy meristem gene are required for maintenance of shoot and root indeterminacy. Plant Physiology 155(2): 735-750.

Non-Patent Literature 4

David-Schwartz R, Borovsky Y, Zemach H, Paran I. (2013) CaHAM is autoregulated and regulates CaSTM expression and is required for shoot apical meristem organization in pepper. Plant Science 203-204: 8-16.

SUMMARY OF INVENTION

Technical Problem

However, what can be known from the above literature is merely that axillary buds can be reduced in plants other than tobacco plants. Therefore, it is still unclear how to obtain a tobacco plant in which the problems resulting from the development of axillary buds are resolved or reduced and which is to be cultivated for harvesting leaf tobaccos.

An object of the present invention is to provide (i) a tobacco plant which is suitable for cultivation for harvesting leaf tobaccos, (ii) a method of obtaining the tobacco plant, (iii) a harvest from the tobacco plant, and (iv) a processed product of the harvest.

Solution to Problem

In view of the problems above, the inventors of the present invention identified a gene which is expected to be involved in the development of axillary buds in tobacco plants, and then searched for an advantageous effect which can be obtained by suppressing the function of the gene in a tobacco plant. This led to the completion of the present invention.

Specifically, in order to attain the object, a tobacco plant in accordance with one aspect of the present invention is a tobacco plant in which a mutation causing functional suppression of at least two genes of the following genes (1) through (3) is introduced into a genome:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

A tobacco plant production method in accordance with one aspect of the present invention is a method of producing a tobacco plant, including the step of:

(A) introducing, into a genome of a tobacco plant, a mutation causing functional suppression of at least two genes of the following genes (1) through (3):

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

A determining method in accordance with one aspect of the present invention is a method of determining a tobacco plant in which development of primary axillary buds is suppressed, the method including the steps of:

(A) obtaining a sample by collecting a part of a tobacco plant;

(B) detecting, from a genome included in the sample, a mutation causing functional suppression of at least two genes of the following genes (1) through (3) on the genomic DNA:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l); and (C) determining that a tobacco plant, in which the mutation has been detected, is a tobacco plant in which the development of the primary axillary buds is suppressed, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

Advantageous Effects of Invention

The present invention can advantageously provide (i) a tobacco plant which is suitable for cultivation for harvesting leaf tobaccos, (ii) a method of obtaining the tobacco plant, (iii) a harvest from the tobacco plant, and (iv) a processed product of the harvest.

DESCRIPTION OF EMBODIMENTS

[1. Tobacco Plant]

Figure 1:
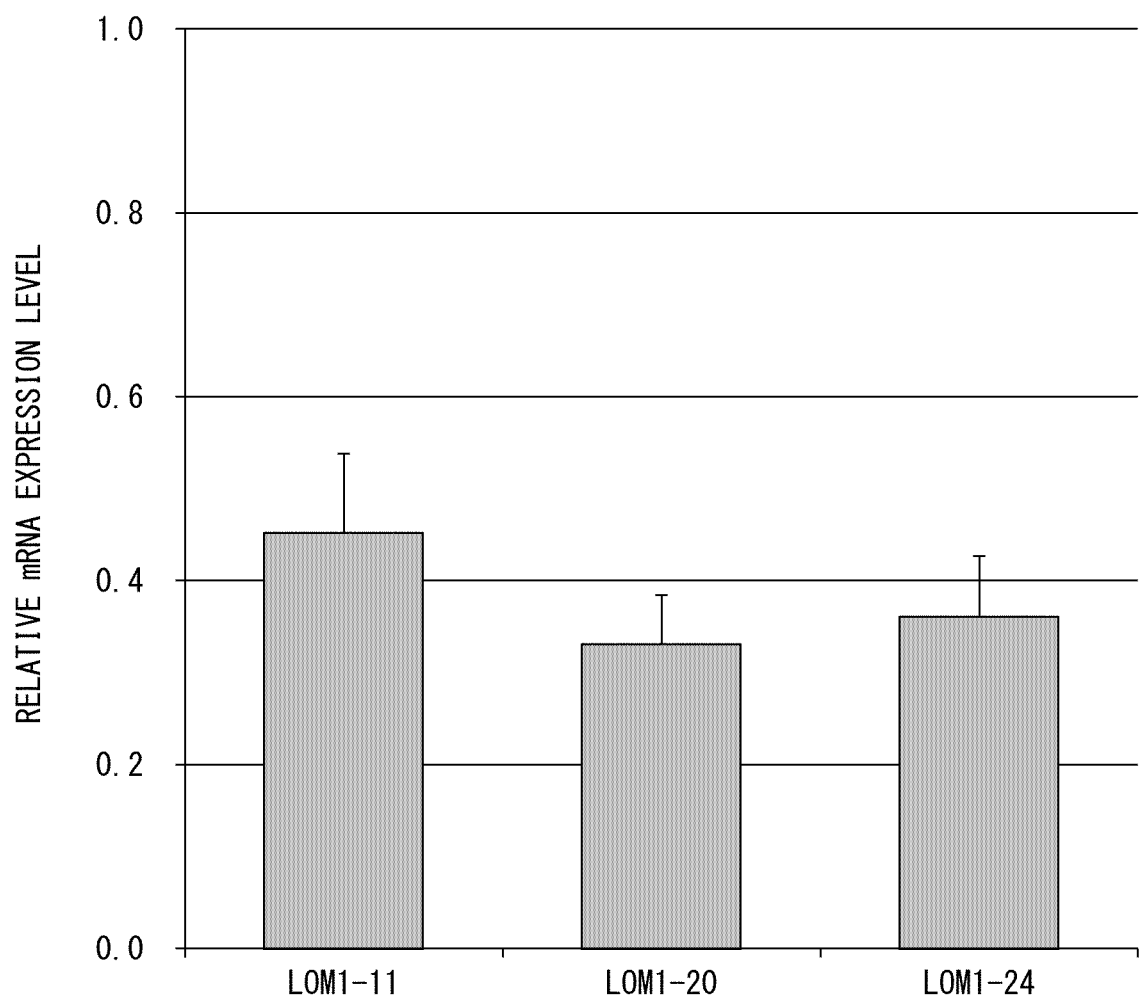
FIG. 1 is a view showing the results of determining mRNA expression levels of NtLOM1 in a tobacco plant (T1 individual).

An embodiment of the present invention provides a tobacco plant in which a mutation is introduced into genome, which mutation causes suppression of functions of at least two genes of specific three genes. It should be noted that the above functional suppression is to suppress the development of primary axillary buds.

Concrete examples of the specific three genes encompass (1) through (3) below.

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l).

The polynucleotides included in the genes (1) through (3) are as follows. The polynucleotide (a) is a polynucleotide encoding a polypeptide having a sequence identity of 90% or higher with an amino acid sequence represented by SEQ ID NO: 1. The polynucleotide (b) is a polynucleotide complementary to a polynucleotide which hybridizes with the polynucleotide (a) under stringent conditions. The polynucleotide (c) is a polynucleotide encoding a polypeptide having a sequence identity of 90% or higher with an amino acid sequence represented by SEQ ID NO: 2. The polynucleotide (d) is a polynucleotide complementary to a polynucleotide which hybridizes with the polynucleotide (c) under stringent conditions. The polynucleotide (e) is a polynucleotide encoding a polypeptide having a sequence identity of 90% or higher with an amino acid sequence represented by SEQ ID NO: 3. The polynucleotide (f) is a polynucleotide complementary to a polynucleotide which hybridizes with the polynucleotide (e) under stringent conditions. The polynucleotide (g) is a polynucleotide encoding a polypeptide having a sequence identity of 90% or higher with an amino acid sequence represented by SEQ ID NO: 4. The polynucleotide (h) is a polynucleotide complementary to a polynucleotide which hybridizes with the polynucleotide (g) under stringent conditions. The polynucleotide (i) is a polynucleotide encoding a polypeptide having a sequence identity of 90% or higher with an amino acid sequence represented by SEQ ID NO: 5. The polynucleotide (j) is a polynucleotide complementary to a polynucleotide which hybridizes with the polynucleotide (i) under stringent conditions. The polynucleotide (k) is a polynucleotide encoding a polypeptide having a sequence identity of 90% or higher with an amino acid sequence represented by SEQ ID NO: 6. The polynucleotide (l) is a polynucleotide complementary to a polynucleotide which hybridizes with the polynucleotide (k) under stringent conditions.

In comparison with wild-type plants, the tobacco plant either exhibits (i) primary axillary buds which are decreased in number or weight (e.g., not more than ½ of wild-type plants) or (ii) no primary axillary bud (see Examples described later). Specifically, a process of removing axillary buds from the tobacco plant is necessary merely a single time or is unnecessary. This allows the amount of labor, which is involved in control of axillary buds in cultivation of a tobacco plant for harvesting leaf tobaccos, to be less than a fraction of the amount of labor involved in such a conventional control of axillary buds.

As used herein, "tobacco plant" and "tobacco" encompass (i) an entire individual (such as a mature plant, a seedling, and a seed), (ii) tissue (such as a leaf, a stem, a flower, a root, a reproductive organ, an embryo, and a part of any of these), and (iii) a dried product of any of these.

As used herein, "axillary bud" refers to both (i) a bud which is generated from an axillary meristem formed at a leaf axil of a leaf primordia and (ii) a shoot obtained as a result of the development of the bud. After topping, axillary buds develop in an order of primary axillary buds, secondary axillary buds, and then tertiary axillary buds, at a base of the same leaf. First, after topping, the primary axillary buds develop. After the primary axillary buds are removed, the secondary axillary buds develop. The "development" of an axillary bud means that the axillary bud, which remained as differentiated tissues from the axillary meristem, starts vigorous development due to, for example, removal of a shoot apex (topping), so that the axillary bud grows and extends.

The "number or weight" of axillary buds means the number or a total weight (fresh weight) of primary axillary buds which have developed in one individual or have been collected. The "number or weight", mainly of primary axillary buds, is herein measured.

As used herein, "sequence identity (of an amino acid sequence)" means a percentage ratio at which a concerned (amino acid) sequence matches a reference (amino acid) sequence. Note that a part of the sequence, which part does not match, is a part at which an amino acid residue is substituted, added, deleted, or inserted.

Note that the term "polypeptide having a sequence identity of 90% or higher with an amino acid sequence represented by [ . . . ]", which specifies the polypeptide with use of an amino acid sequence listed in a sequence listing, means a wild-type polypeptide. The wild-type polypeptide means a polypeptide which is typically present in a *Nicotiana* plant described later. As used herein, the terms "polypeptide" and "protein" have substantially the same meaning, and can therefore be used interchangeably.

Therefore, a polypeptide, which is decreased in abundance in the tobacco plant, need only be a polypeptide having a sequence identity of 90% or higher with each of the amino acid sequences listed in the sequence listing. A higher sequence identity is more preferable (e.g., 91%, 92%, 93%, 94%, 95%, 96%, 97%, 98%, or 99% or higher).

The "decrease in abundance" of a polypeptide means the presence of the polypeptide in an amount of 70% or lower, 60% or lower, 50% or lower, 40% or lower, 30% or lower, 20% or lower, 10% or lower, 5% or lower, or 1% or lower, relative to the abundance of a wild-type polypeptide as a reference. The abundance of the polypeptide relative to that of the wild-type polypeptide as a reference can be selected as appropriate from the above values which result in a decrease in the number or weight of primary axillary buds.

It is preferable that the above-described decrease in abundance of a polypeptide in the tobacco plant is, with stability, genetically inherited by cultured cell, callus, protoplast, seed, and offspring, any of which is obtained from the tobacco plant. Therefore, the tobacco plant can be an individual developed from cultured cell, callus, protoplast, seed, or offspring, any of which is produced through artificial operation. In addition, these materials, from which the individual develops, are also encompassed in the scope of the present invention.

The scope of the tobacco plant can further encompass bred progeny obtained by crossing. Breeding with use of mutants has been done in many plant species. Representative examples of such plant species encompass rice, wheat, barley, and soybean. For example, a mutant isolated from a mutant population treated with use of a mutagen has multiple mutations other than at a region of a target gene. In general, therefore, backcrossing is to be performed to remove excess mutations. In this crossing, a desired character (suppressed development of primary axillary buds) of the mutant can be introduced into an existing cultivar by crossing the mutant with the cultivar having excellent character. A bred progeny thus obtained can be a variety obtained by adding high values to an existing cultivar.

Note that the desired character of the mutant is derived from mutations introduced into a plurality of positions (e.g., a plurality of genes) on a genome. For efficient backcrossing, it is therefore necessary to select, in advance, individuals having the mutations. In the selection of the individuals, it is advantageous to be able to easily detect (i) whether or not the mutations are present in the individuals and (ii) whether the mutations are homozygous or heterozygous. The mutations can be detected by a method (described later) for detecting mutations in genes. Apart from the perspective above, it is preferable that lines having a high cultivar-return-rate (i.e., the proportion of a cultivar-derived genomic region to the entire genomic region) is obtained with the fewer times of crossing. Even fewer times of crossing can be achieved by, for example, Marker Assisted Selection (MAS) which uses a background marker indicative of a polymorphism between the mutant and the existing cultivar. The background marker indicative of a polymorphism can be, for example, SNP or Simple Sequence Repeat (SSR) each of which is known in tobacco. Other than the existing marker, examples of a new marker encompass the following differences (a) and (b) which are identified by determining respective genome sequences of the mutant and the existing cultivar for use in crossing and then making a comparison between the genome sequences: (a) a difference in nucleotide sequence and (b) a difference in the number of repeat sequences on a genome.

Gene and genome will be described below by taking *Nicotiana tabacum* (*N. tabacum*) as a reference. *Nicotiana tabacum* (*N. tabacum*), which serves as a reference in the description below, is an amphidiploid and has both an S genome and a T genome derived from *Nicotiana sylvestris* and *Nicotiana tomentosiformis*, respectively, each of which is an ancestor species thereof. In *N. tabacum*, in most cases, genes indicated by an identical name are present in each of an S genome and a T genome. The three genes described above each include two alleles in an S genome and two alleles in a T genome (i.e., the total of 4 alleles on the genome of *N. tabacum*).

Note that in a coding region of a tobacco plant, a nucleotide sequence of part (not the whole) of genes encoding polypeptides, which possesses the substantially same function between species, may have (i) 1% to several % difference between cultivars and (ii) approximately 10% or lower difference between a cultivar and wild species.

A polypeptide having an amino acid sequence represented by SEQ ID NO: 1 is encoded by, for example, a polynucleotide having a nucleotide sequence represented by SEQ ID NO: 7. A polypeptide having an amino acid sequence represented by SEQ ID NO: 2 is encoded by, for example, a polynucleotide having a nucleotide sequence represented by SEQ ID NO: 8. These polynucleotides are each cDNA of NtLOM3 demonstrated in Examples described later. SEQ ID NO: 7 represents a cDNA sequence of NtLOM3 of an S genome. SEQ ID NO: 8 represents a cDNA sequence of NtLOM3 of a T genome. SEQ ID NOs: 13 and 14 represent nucleotide sequences of an S genome and a T genome, respectively, of NtLOM3 gene.

A polypeptide having an amino acid sequence represented by SEQ ID NO: 3 is encoded by, for example, a polynucleotide having a nucleotide sequence represented by SEQ ID NO: 9. A polypeptide having an amino acid sequence represented by SEQ ID NO: 4 is encoded by, for example, a polynucleotide having a nucleotide sequence represented by SEQ ID NO: 10. These polynucleotides are each cDNA of NtLOM2 demonstrated in Examples described later. SEQ ID NO: 9 represents a cDNA sequence of NtLOM2 of an S genome. SEQ ID NO: 10 represents a cDNA sequence of NtLOM2 of a T genome. SEQ ID NOs: 15 and 16 represent nucleotide sequences of an S genome and a T genome, respectively, of NtLOM2 gene.

A polypeptide having an amino acid sequence represented by SEQ ID NO: 5 is encoded by, for example, a polynucleotide having a nucleotide sequence represented by SEQ ID NO: 11. A polypeptide having an amino acid sequence represented by SEQ ID NO: 6 is encoded by, for example, a polynucleotide having a nucleotide sequence represented by SEQ ID NO: 12. These polynucleotides are each cDNA of NtLOM1 demonstrated in Examples described later. SEQ ID NO: 11 represents a cDNA sequence of NtLOM1 of an S genome. SEQ ID NO: 12 represents a cDNA sequence of NtLOM1 of a T genome. SEQ ID NOs: 17 and 18 represent nucleotide sequences of an S genome and a T genome, respectively, of NtLOM1 gene.

There are methods for isolating orthologous genes. Examples of such methods well-known to those skilled in the art encompass a hybridization technique (Southern, E. M., Journal of Molecular Biology, Vol. 98, 503, 1975) and a polymerase chain reaction (PCR) technique (Saiki, R. K., et al. Science, vol. 230, 1350-1354, 1985, Saiki, R. K. et al. Science, vol. 239, 487-491, 1988). Therefore, those skilled in the art can easily isolate an orthologous gene of the gene (1) from various plants while, for example, (i) a polynucleotide having a nucleotide sequence shown in SEQ ID NO: 7 or a part of the polynucleotide is serving as a probe or (ii) oligonucleotide hybridizing with the polynucleotide under stringent conditions is serving as a primer. Likewise, those skilled in the art can easily isolate an orthologous gene of the gene (1) from various plants with use of (i) a polynucleotide having a nucleotide sequence shown in SEQ ID NO: 8 or (ii) a part of the polynucleotide. Skilled persons who read these descriptions can easily (i) isolate an orthologous gene of the gene (2) based on the nucleotide sequence of SEQ ID NO: 9 or SEQ ID NO: 10 (or on a part of the nucleotide sequence and (ii) isolate an orthologous gene from the gene (3) based on the nucleotide sequence of SEQ ID NO: 11 or SEQ ID NO: 12 (or on a part of the nucleotide sequence).

Note that the stringent conditions means, in general, conditions under which (i) a double-stranded polynucleotide specific to a nucleotide sequence is formed and (ii) the formation of a non-specific double-stranded polynucleotide is markedly suppressed. In other words, the stringent conditions can be expressed as conditions under which hybridization is carried out at a temperature in a range from (i) a melting temperature (Tm) of a hybrid of nucleic acids which are highly homologous to each other (e.g., a double-stranded polynucleotide perfectly-matched to a probe) to (ii) 15° C. lower than the melting temperature (Tm), preferably 10° C. lower than the melting temperature (Tm), more preferably 5° C. lower than the melting temperature (Tm). Examples of the stringent conditions encompass conditions under which hybridization is carried out with use of a common buffer solution for hybridization, at a temperature of 68° C., and for a period of 20 hours. In one example, hybridization can be carried out in a buffer solution (consisting of 0.25M Na2HPO4, pH 7.2, 7% SDS, 1 mM EDTA, and 1×Denhardt's solution) for 16 hours to 24 hours at a temperature in a range from 60° C. to 68° C., preferably at 65° C., further preferably at 68° C., and then washing can be carried out twice in a buffer solution (consisting of 20 mM Na2HPO4, pH 7.2, 1% SDS, and 1 mM EDTA) for 15 minutes at a temperature in a range from 60° C. to 68° C., preferably at 65° C., further preferably at 68° C. In another example, prehybridization is carried out overnight at 42° C. in a hybridization solution (including 25% formamide or 50% formamide (for a stringent condition), 4×SSC (sodium chloride/sodium citrate), 50 mM Hepes pH 7.0, 10×Denhardt's solution, and 20 μg/ml denatured salmon sperm DNA), and then hybridization is carried out by adding a labeled probe thereto and keeping a resulting solution at 42° C. overnight. In washing following the hybridization, conditions for a washing solution and a temperature are approximately "1×SSC, 0.1% SDS, 37° C.", approximately "0.5×SSC, 0.1% SDS, 42° C." for a more stringent condition, approximately "0.2×SSC, 0.1% SDS, 65° C." for a further severer condition. It can be thus expected that as the conditions for the washing following the hybridization become more stringent, DNA having higher homology to a sequence of a probe is isolated. However, the above-indicated combinations of conditions on SSC, SDS, and temperature are merely examples. Those skilled in the art can achieve a stringency similar to the above by appropriately combining the above-described or other elements (e.g., a probe concentration, a probe length, and a time period for a hybridization reaction) that determine the stringency of hybridization. For example, those skilled in the art can easily obtain such genes by referring to Molecular Cloning (Sambrook, J. et al., Molecular Cloning: a Laboratory Manual 2nd ed., Cold Spring Harbor Laboratory Press, 10 Skyline Drive Plainview, N.Y. (1989)).

The term "at least one of (former) . . . gene and (latter) . . . gene" as used herein to specify a gene refers to any one of the following genes and a combination thereof:
a (former) gene (gene on S genome);
a (latter) gene (gene on T genome); and
a combination of the (former) gene (gene on S genome) and the (latter) gene (gene on T genome).

In a specific embodiment in which mutations are introduced into two genes of the genes (1) through (3) above, the tobacco plant has the above-described mutations in one or more alleles, per gene, selected from (i) at least one (one or two) of two alleles in S genome and (ii) at least one (one or two) of two alleles in T genome. Specifically, the tobacco plant in accordance with the specific embodiment has the mutations in two genes selected from NtLOM1 through NtLOM3 which are on the genome.

As described above, a tobacco plant in many cases has one set of genes (i.e., two genes) in each of a T genome and an S genome. Therefore, in order for the functions of the genes to completely disappear as a result of the introduction of the mutation into genes, it is necessary to introduce the mutations into all of the (four) genes in the T genome and the S genome. Note, however, that in a tobacco plant in which the function of one gene has completely disappeared due to the mutation, the development of primary axillary buds is not suppressed (see Comparative Examples described later).

Note that the tobacco plant in accordance with an embodiment of the present invention preferably has mutations in at least two genes, and more preferably has mutations in two genes. In a more preferable tobacco plant, the number of alleles into which mutations are to be introduced is 8. In a preferable tobacco plant, it is unnecessary for the mutation to be introduced into all of the 8 alleles. This is because the suppression of the development of primary axillary buds can be observed in, for example, a tobacco plant in which the mutations are introduced into 6 or more (i.e., 6 or 7) alleles out of 8 alleles.

As described later in Examples, two genes of the tobacco plant, into which the mutations are introduced, are particularly preferably a combination of NtLOM2 and NtLOM3. In an embodiment of the combination of these genes, the tobacco plant has mutations in 6 alleles and no mutations in 2 alleles, out of 2 genes. In the embodiment, the tobacco plant has mutations in: 4 alleles of NtLOM2 and 2 alleles of NtLOM3; 3 alleles of NtLOM2 and 3 alleles of NtLOM3; or 2 alleles of NtLOM2 and 4 alleles of NtLOM3.

As used herein, "functional suppression of a gene" means a state in which the gene on a genome is not fulfilling its original function. Therefore, "functional suppression of a gene" is a term encompassing (i) "gene disruption", (ii) "gene mutation", and (iii) "suppressed expression of gene" by another gene (including an exogenous gene).

"Gene disruption" means that (i) a gene, which is originally present on a genome, is not present on the genome or (ii) a transcribed product is not produced from a gene on a genome. "Gene mutation" means, for example, (i) a mutation of a gene (i.e., decrease or impairment of the function) such that an original functional polypeptide is not produced, (ii) a mutation of the gene such that although a functional polypeptide is produced, the amount of the functional polypeptide produced is decreased, or (iii) a mutation of the gene such that although a functional polypeptide is produced, the stability of the functional polypeptide is decreased. "Suppressed expression of gene" means, for example, a state in which although no change has occurred to the nucleotide of the gene, the transcriptional or translational function of the gene (from transcription into mRNA to subsequent translation into polypeptide) is modified through another factor so that (i) the amount of protein produced is decreased or (ii) no polypeptide is produced. "Suppressed expression of gene" may occur as a result of, for example, degradation of mRNA which is transcribed from the gene.

As used herein, "mutation" has the meaning ordinarily understood in the technical field to which the present application belongs, and means, for example, any change in a nucleotide on a wild-type genome or any change in an amino acid residue in a wild-type polypeptide (examples of the change encompass substitution, deletion, insertion, addition, duplication, inversion, or translocation). "Gene mutation" means, for example, (i) a mutation of a gene such that an original functional polypeptide is not produced, (ii) a mutation of the gene such that although a polypeptide is produced, the amount of the polypeptide produced is decreased, (iii) a mutation of the gene such that although a polypeptide is produced, the stability of the polypeptide is decreased, or (iv) a mutation of the gene such that the gene (a coding region or a full length including an untranslated region) is lost, or that transcription from the gene is suppressed (e.g., a transcription-regulating region or a transcription-initiating region is deleted).

In a case where the functions are impaired by substitution, the substitution can be present in at least one of the following: a promoter sequence (such as a sequence upstream (5' end) and a sequence downstream (3' end) with the coding region as a reference), a 5' untranslated region and a 3' untranslated region, a conserved sequence (5'GT-AG3') present at both ends of an intron, and a coding region.

For example, in a case where substitution in nucleotide sequences (a promoter sequence, a 5' untranslated region, and a 3' untranslated region of a gene), which are important for regulating gene expression, leads to a decrease in transcriptional activity of the gene expression or to a decrease in stability of a transcribed product. Any of these decreases may lead to a reduction in transcribed product from the gene. This may lead to a reduction in translation product. Substitution in a conserved sequence leads to splicing abnormality of mRNA. This results in abnormal mRNA into which an unnecessary intron is added or inserted. The abnormal mRNA either generates an abnormal translation product or does not terminate translation, due to, for example, frame shifting.

Substitution in a coding region may lead to a translation product which has an incomplete length or to a translation product which does not maintain an original function. The translation product having an incomplete length is derived from conversion, by the substitution, of a codon, which is encoding an amino acid, into a stop codon (i.e., nonsense mutation). In comparison with the original translation product, the translation product having an incomplete length is such that one or more consecutive amino acid residues including an amino acid residue at a C-terminus are deleted. The nonsense mutation occurs to any codon on located upstream of the original stop codon, and is preferably located upstream of the original stop codon with one or more codons therebetween. A translation product having lost the original function can occur due to substitution of an amino acid. The translation product has, therein, a change in tertiary structure, deterioration of a function as a functional domain, or the like. The substitution of the amino acid is preferably a non-conservative substitution with a high possibility of changing the function of the translation product. Examples of the non-conservative substitution encompass (i) substitution of an amino acid by another amino acid having a different electric charge or a different hydrophobicity (e.g., substitution of a basic amino acid by an acidic amino acid or substitution of a polar amino acid by a non-polar amino acid) and (ii) substitution of an amino acid by another amino acid having a side chain of a different bulk (three-dimensional size).

In a case where mutations (deletion, insertion, or the like) other than substitution, occur within a promoter sequence, a 5' untranslated region, and a 3' untranslated region, a decrease may occur in transcriptional activity or stability as in the case of the substitution, so that (i) the amount of transcribed product may decrease and (ii) the amount of polypeptide may decrease. In addition, a mutation other than substitution into a conserved sequence of an intron, as in the case of the substitution, leads to translation of polypeptide having an amino acid sequence different from that of the original amino acid sequence. The mutation, which is other than substitution into a coding region, causes polypeptide, which have amino acid sequences different from original sequences, to be generated by the translation, the difference in amino acid sequences occurring due to (i) deletion or insertion of an amino acid residue (caused by deletion or insertion of consecutive nucleotides which are multiples of 3) or (ii) frame shifting. In a case of a large deletion of the entire gene itself or an insertion of a large fragment into the gene, the expression of the gene may be lost.

An individual, which was generated as a result of the gene mutation or gene disruption, is herein called a mutant (hereinafter simply referred to as "mutant") of a tobacco plant. The mutant can have the mutation in any of an S genome or a T genome, and preferably has the mutation in both the S genome and the T genome. Note that (i) a single mutation or a plurality of mutations can occur in a single gene and (ii) the kind of mutation to impair a function is not limited. The total of four alleles, which include two alleles in an S genome and two alleles in a T genome, can have identical mutations or different mutations.

Examples of suppressed expression of a gene encompass (i) suppression of transcription from the gene to an mRNA, (ii) suppression (e.g., degradation of the mRNA) of translation from the gene into a polypeptide through an mRNA and (iii) suppression of the function of the polypeptide which is generated by the translation. The suppression of the transcription can be achieved by, for example, (i) inhibition of a transcription factor which promotes the transcription from the gene or (ii) inhibition of access of a transcription initiation factor to the gene. The suppression of the translation can be achieved by use of an antisense RNA molecule, an RNAi molecule, or a co-suppression molecule. The functional suppression of the polypeptide can be achieved by a molecule which inhibits the function of a functional polypeptide by binding to the functional polypeptide. Examples of such a molecule encompass decoy nucleic acid, ribozyme, antibody, and inhibitory peptide.

The above-described suppression (of the transcription, translation, and polypeptide function) can be achieved by, for example, (i) directly introducing molecules for achieving the suppression into a plant or (ii) introducing, into a plant, nucleic acid molecules encoding the molecules (i.e., transformation of the plant). As a result of the transformation of the plant, the nucleic acid molecules are incorporated into one or more of any regions of genomes of the plant. Provided that the suppression is achieved, it is unnecessary for the nucleic acid molecules to be incorporated into both S genome and T genome as a result of the transformation of the plant.

In the tobacco plant, the functional suppression is preferably a decrease, as compared with a wild-type plant, in abundance of the polypeptides which are expression products of the at least two genes. Specifically, the abundance is decreased based on mutation which leads to suppressed expression of a gene encoding the wild-type polypeptide. As has been described, it is sufficient if the mutation is present on a genome of the tobacco plant.

A polypeptide, which has a sequence identity of 90% or higher with an amino acid sequence represented by SEQ ID NO: 1, 2, 3, 4, 5, or 6, is a polypeptide which is present in a wild-type plant (or a variant thereof). Therefore, the abundance of the polypeptide in the tobacco plant is decreased in comparison with that of a wild-type plant. This causes the tobacco plant to be inferior to the wild-type plant in terms of the function. Examples of the function encompass a function of a wild-type plant, such as (i) a function to form axillary meristem, (ii) a function to differentiate an axillary bud from axillary meristem, or (iii) a function to maintain or promote the capability of the development of an axillary bud.

In the tobacco plant, the functional suppression is preferably a decrease, as compared with a wild-type plant, in an amount of translation of the polypeptides which are expression products of the at least two genes. The translation of the polypeptide is based on (i) a decrease in mRNA (due to, for example, the abundance of mRNA, such as the instability of the mRNA itself, promoted degradation of the mRNA, or suppression of the transcription of the mRNA) or (ii) a decrease in an amount of translation from mRNA (due to, for example, lack of elements (tRNA and ribosome) constituting translation, inhibition of recruit, or functional impairment).

In the tobacco plant, the functional suppression is preferably a decrease, as compared with a wild-type plant, in an amount of transcription from the at least two genes to mRNA. The decrease in the amount of the transcription occurs due to, for example, suppression of transcription from a gene to mRNA. The suppression of the transcription can be achieved by, for example, inhibition of access of a transcription initiation factor to the gene, which occurs as a result of introducing a mutation into the gene.

In the tobacco plant, the functional suppression is preferably promotion of degradation of mRNAs transcribed from the at least two genes. The degradation of the mRNA may be caused by, for example, (i) the presence of an exogenous factor leading to the degradation of the mRNA, (ii) activation of an endogenous constituent element leading to the degradation of the mRNA, or (iii) the presence of a sequence for promoting the degradation of the mRNA.

In the tobacco plant, the mutation is preferably insertion, into an outside of a region in which the at least two genes are present, of a polynucleotide expressing a factor which promotes the degradation of the mRNAs transcribed from the at least two genes.

The factor is preferably an antisense RNA molecule, an RNAi molecule, or a co-suppression molecule.

The mutations or disruption of the at least two genes preferably occurs as a result of spontaneous mutation, mutagen treatment, gene recombination, genome editing, or gene knockout. The spontaneous mutation of the at least two genes generally occurs due to (i) replication errors and (ii) damage to the gene. The cause of the damage is, for example, exposure to publicly-known, naturally-occurring mutagens or publicly-known mutagens which have been artificially produced and then remaining in a natural environment (for example, radiation, ultraviolet rays, or mutation-inducing substances (such as EMS)). The at least two genes can be subjected to a mutagen treatment by artificially causing the mutagen to take effect on a tobacco plant (as necessary, in combination with suppression of a gene repair function). Recombination of the at least two genes can be performed by homologous recombination of all or part of a target gene with a recombinant sequence according to a publicly-known genetic recombination method. Genome editing of the gene can be performed by a publicly-known technique (for example, zinc-finger nucleases: ZFN, transcription activator-like effector nucleases: TALEN, and CRISPR/Cas9 system). The gene knockout can be performed by, for example, (i) transfer of the gene by use of a publicly-known transposase or (ii) introduction of T-DNA.

The various mutations described above can be easily introduced into a tobacco plant by those skilled in the art who have referred to, for example, publicly-known genome sequences of genes described below. Specifically, based on these pieces of sequence information, it is possible to appropriately determine a region which is present in a genome of any of various tobacco plants encompassed in the scope of the present invention and at which a mutation should be introduced.

NtLOM1: (S genome) Sol Genomics Network (SOL) accession #Ntab-TN90-AYMY-SS11024, and (T genome) Sol Genomics Network (SOL) accession #Ntab-TN90-AYMY-SS12340

NtLOM2: (S genome) Sol Genomics Network (SOL) accession #Ntab-TN90-AYMY-SS9212, and (T genome) Sol Genomics Network (SOL) accession #Ntab-TN90-AYMY-SS8

NtLOM3: (S genome) Sol Genomics Network (SOL) accession #Ntab-TN90-AYMY-SS9212, and (T genome) Sol Genomics Network (SOL) accession #Ntab-TN90-AYMY-SS8

The tobacco plant is not limited to any particular one provided that the tobacco plant is a *Nicotiana* plant which is not limited to any particular one provided that the *Nicotiana* plant is a plant belonging to *Nicotiana*. Examples of the tobacco plant encompass *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *Hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *Ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and a hybrid of *Nicotiana* plants. Among these *Nicotiana* plants, *Nicotiana benthamiana, Nicotiana rustica*, and *Nicotiana tabacum* are more preferable. *Nicotiana rustica* and *Nicotiana tabacum*, which are used as materials to produce leaf tobacco, are particularly preferable.

[2. Method of Producing Tobacco Plant]

In one aspect, the present invention provides a method of producing the tobacco plant. The production method includes the step of introducing, into a genome of a tobacco plant, a mutation which causes functional suppression of at least two genes of the above-described three genes.

This introducing step results in the suppression of the development of primary axillary buds through the functional suppression of the gene, which is caused by the mutation. The suppression of the development of primary axillary buds through the functional suppression of the genes is performed as outlined above. Therefore, as concrete examples of carrying out the introducing step, the following description will discuss suppression of gene expression and introduction of a mutation into a gene, which are performed through transformation of a tobacco plant with use of a vector.

The vector to be used for the transformation of a tobacco plant for the purpose of the suppressed expression of the gene or the introduction of the mutation into the gene is not limited to any particular one, provided that a polynucleotide inserted into the vector can be expressed in a plant cell. Examples of a suitable vector encompass pBI, pPZP, and pSMA vectors each of which allows introduction of a target polynucleotide into a plant cell via *Agrobacterium*. In particular, plasmids of binary vectors (e.g., pBIG, pBIN19, pBI101, pBI121, pBI221, and pPZP202) are preferable.

In a case where the suppressed expression of the gene is achieved by RNAi, an RNAi trigger sequence, which is used by the RNAi to suppress the expression of the target gene, is inserted into the vector. Examples of the RNAi trigger sequence encompass (i) a polynucleotide (sense RNA portion) which is (a) a part of a polynucleotide (which can have a substitution of 0.1% to 1%) encoding a polypeptide having an amino acid sequence represented by SEQ ID NO: 1, 2, 3, 4, 5, or 6 or a part of a polynucleotide (which can have a substitution of 0.1% to 1%) having SEQ ID NO: 7, 8, 9, 10, 11, or 12 and (b) represented by a nucleotide sequence of at least 21 to 30 consecutive bases (e.g., 21 or more bases, 22 or more bases, 23 or more bases, 24 or more bases, 25 or more bases, 26 or more bases, 27 or more bases, 28 or more bases, 29 or more bases, and 30 or more bases) and (ii) a polynucleotide (antisense RNA portion) represented by a nucleotide sequence which is complementary to the polynucleotide (i). More specifically, the nucleotide sequence of the "at least 21 to 30 consecutive bases" described above means a nucleotide sequence of 21 or more consecutive bases, 23 or more consecutive bases, 25 or more consecutive bases, 30 or more consecutive bases, 35 or more consecutive bases, 40 or more consecutive bases, 45 or more consecutive bases, 50 or more consecutive bases, 60 or more consecutive bases, 70 or more consecutive bases, 80 or more consecutive bases, 90 or more consecutive bases, or 100 or more consecutive bases.

As described above, the suppression of the gene expression in the tobacco plant in accordance with an aspect of the present invention is preferably genetically inherited. Therefore, the RNAi trigger sequence is preferably incorporated with a genome of the tobacco plant.

A tobacco plant, in which expression of a plurality of genes is simultaneously suppressed, can be obtained by crossing two tobacco plants in which expression of differing genes is suppressed. In addition, a tobacco plant, in which expression of a plurality of genes is simultaneously suppressed, can be obtained by (i) performing transformation which may cause expression of a plurality of differing genes to be simultaneously suppressed and then (ii) selecting the tobacco plant in which expression of a plurality of genes is simultaneously suppressed.

Note that in a case where a tobacco plant in which a plurality of genes are functionally suppressed is to be obtained by use of crossing, (i) one of tobacco plants to be crossed can be prepared by mutation or disruption (described below) of a gene and (ii) the other one of the tobacco plants to be crossed can be prepared by transformation (which causes suppressed expression of a gene).

The introduction of a mutation into the gene of the tobacco plant can be achieved by a publicly-known genome editing technique. Examples of the genome editing technique encompass CRISPR/Cas9 system, TALEN, and ZFN. According to the CRISPR/Cas9 system, the genome editing is possible if guide RNAs and a Cas9 protein is present in a target cell. According to TALEN and ZFN, the genome editing is possible if a fusion protein (in which DNA-binding domains and nuclease are fused) is present in a target cell. Therefore, the guide RNAs, the Cas9 proteins, and the fusion proteins can be directly introduced into a target cell. Examples of a method of directly introducing any of these into a target cell encompass a PEG method, an electroporation method, and a particle bombardment method.

According to the CRISPR/Cas9 system, (i) a sequence, which is complementary to a nucleotide sequence located immediately upstream of XGG on a genome, forms a base pair with part of a guide RNA and (ii) a double stranded genomic DNA is cut by Cas9 in the nucleotide sequence. Examples of the nucleotide sequence recognized by the guide RNA encompass a part of (i) a polynucleotide (which can have a substitution of 0.1% to 1%) encoding a polypeptide having an amino acid sequence represented by SEQ ID NO: 1, 2, 3, 4, 5, or 6 or (ii) a polynucleotide (which can have a substitution of 0.1% to 1%) having SEQ ID NO: 7, 8, 9, 10, 11, or 12, which part is 10 or more consecutive bases (e.g., 15 or more consecutive bases, preferably 17 or more consecutive bases, more preferably 18 or more consecutive bases, still more preferably 19 or more consecutive bases, and most preferably 20 or more consecutive bases) located immediately upstream of XGG.

According to the TALEN, a pair of DNA-binding domains in artificial nucleases forming a dimer each bind to a corresponding one of nucleotide sequences, which is present at each terminus of a FokI cleavage domain so as to be away from the terminus by a spacer of 5 to 20 bases. The nucleotide sequence is present at one and the other strands of double stranded genomic DNA. Therefore, one of the pair of DNA-binding domains binds to the one strand, and the other of the pair of DNA-binding domains binds to the other strand. The DNA binding domain is composed of a repeating unit (module) which include 33 to 34 amino acid residues. The number of modules corresponds to the number of nucleotides to which the DNA bind domain bind. Provided that 33 to 34 amino acid residues serve as a repeating unit (module), the DNA-binding domain contains modules, the number of which corresponds to the number of nucleotides to bind to. The nucleotide sequence to which the DNA-binding domain binds is 10 or more consecutive bases, preferably 14 or more consecutive bases, and more preferably 18 or more consecutive bases, which are present at each terminus of a FokI cleavage domain so as to be away from the terminus by a spacer of 5 to 20 bases and which are a part of a polynucleotide (which can have a substitution of 0.1% to 1%) encoding a polypeptide having an amino acid sequence represented by SEQ ID NO: 1, 2, 3, 4, 5, or 6, or a polynucleotide (which can have a substitution of 0.1% to 1%) having SEQ ID NO: 7, 8, 9, 10, 11, or 12.

According to ZFN, as in the case of TALEN, a pair of DNA-binding domains in artificial nucleases forming a dimer each bind to a corresponding one of nucleotide sequences, which is present at each terminus of a FokI cleavage domain so as to be away from the terminus by a spacer of 5 to 20 bases. The DNA-binding domain contains a plurality of zinc finger modules. The nucleotide sequence is 9 or more consecutive bases, preferably 12 or more consecutive bases, and more preferably 18 or more consecutive bases, which are present at respective termini of a FokI cleavage domain with a spacer of 5 to 20 bases therebetween and which are a part of a polynucleotide (which can have a substitution of 0.1% to 1%) encoding a polypeptide having an amino acid sequence represented by SEQ ID NO: 1, 2, 3, 4, 5, or 6, or a polynucleotide (which can have a substitution of 0.1% to 1%) having SEQ ID NO: 7, 8, 9, 10, 11, or 12.

RNAi, CRISPR/Cas9 system, TALEN, and ZFN, which have been described above, can each be read so that, according to the description of each detail, the polypeptide having an amino acid sequence represented by SEQ ID NO: 1, 2, 3, 4, 5, or 6 is replaced with an orthologous polypeptide which (i) has a sequence identity of 90% or higher with the polypeptide and (ii) is present in another kind included in *Nicotiana* plant. Likewise, the description of the previous paragraph can be read so that a polynucleotide having SEQ ID NO: 7, 8, 9, 10, 11, or 12 is replaced with a polynucleotide of orthologous gene, which (i) has a sequence identity of 90% or higher with the polynucleotide and (ii) is present in another kind included in *Nicotiana* plant.

As described above, the mutation, which is introduced into the at least two genes of the tobacco plant in accordance with an aspect of the present invention and which causes functional suppression of the at least two genes, is preferably genetically inherited. However, an exogenous polynucleotide introduced in a tobacco plant by genome editing is preferably eliminated from the tobacco plant after it is confirmed that a desired mutation is introduced in the tobacco plant. In a case where the exogenous polynucleotide is retained in the tobacco plant, an undesired mutation may (continue to) be introduced. This may cause a desired character (such as suppression of primary axillary buds) to be lost, or may threaten the survival of the tobacco plant.

The introduction of the mutation into the at least two genes of a tobacco plant or the disruption of the at least two genes of the tobacco plant can be achieved through another biotechnological method (e.g., a method in which transposon or *Agrobacterium* is utilized). Concrete examples of the method encompass a method in which a tobacco plant is introduced with (i) retrotransposon tnt1 of tobacco or transposon of another plant or (ii) T-DNA of Ti plasmid of *Agrobacterium*.

Alternatively, the introduction or the disruption can be achieved through another method (mutagen treatment of a tobacco plant). Examples of a source of the mutation encompass small molecule compounds (such as ethyl methane sulfonate (EMS), N-ethyl-N-nitrosourea (ENU), sodium azide) and radiations (such as gamma rays, heavy ion beams, X-rays, neutron beams, and ultraviolet rays).

A mutation can be introduced into any regenerable tobacco plant. Examples of the tobacco plant encompass seeds, roots, leaves, flowers, reproductive organs, and embryos. A preferable example is seeds.

What can be obtained by the methods above can be a mutant population of a plant which has various mutations (or no mutation). Therefore, an individual exhibiting a desired phenotype can be further selected from the mutant population. As an example of the selection of an individual, the following description will discuss a procedure for selecting a desired individual from a mutant population (panel) which is obtained in a case where tobacco is treated with use of a mutagen.

A tobacco mutant, which is functionally impaired due to mutations in the total of 4 alleles of both T genome and S genome for one gene or due to disruption of the total of 4 alleles for one gene, can be obtained by, for example, a method described below. A tobacco is treated with a mutagen as described above to prepare a population (panel) of tobacco mutants with mutations in the whole tobacco genome, and genomic DNAs are extracted. By utilizing gene-specific primers of each of the S genome and the T genome, target genes (polynucleotide) are amplified from the genomic DNAs of the panel. Subsequently, nucleotide sequences of resulting products are determined, and a line having a mutation is then selected. From an M2 individual group of a selected line, an M2 individual having a homozygous mutation in an S genome and an M2 individual having a homozygous mutation in a T genome are prepared and then crossed to obtain $F_1$ individuals. Subsequently, a selfed progeny ($F_2$) is cultivated from the $F_1$ individuals. From the selfed progeny ($F_2$), individuals having homozygous mutations in both an S genome and a T genome are obtained (such individuals are obtained at a probability of 1/16 since two elements are recessive).

Alternatively, the tobacco mutant having mutations in the two genes can be obtained by (i) further subjecting, to a mutagen treatment, the tobacco mutant, having the mutation in one gene, which has been obtained by the method described above, (ii) selecting, from the above-described mutant population, the tobacco mutant having the mutations in the two genes, or (iii) crossing two kinds of tobacco mutants, which have been obtained by the method above and which have the mutations in respective genes, and then selecting a tobacco plant having the mutations in desired two genes. In a case where the method of introducing the mutation is to be changed, it is sufficient to replace the method described above concerning the mutagen with another method (e.g., the above-described method of introducing a mutation into a tobacco plant with use of genome editing or gene knockout, or the above-described method of carrying out transformation of a tobacco plant with use of a vector).

Specifically, through, for example, stages (1) through (4) below, any of the following tobacco plants can be obtained: (i) a tobacco plant having mutations in two genes (first and second genes), (ii) a tobacco plant in which two genes are disrupted, and (iii) a tobacco plant which has a mutation in a first gene and in which a second gene is disrupted. Note that the stages (3) and (4) can be omitted by, for example, introducing the mutations into the two genes simultaneously in the stage (1), and then selecting, in the stage (2), a tobacco mutant having the mutations in the two genes.

(1) The mutant population is produced by use of any method of introducing a mutation (e.g., spontaneous mutation, mutagen treatment, gene recombination, genome editing, gene knockout, transformation, or a combination of any of these methods).

(2) A first tobacco mutant, which has the mutation in the first gene (or in which the first gene is disrupted), is selected from the tobacco mutant produced in the stage (1).

(3) A second tobacco mutant, which has the mutation in the second gene (or in which the second gene is disrupted), is prepared by repeating the stages (1) and (2).

(4) The first and second tobacco plants are crossed.

The method of producing the tobacco plant in accordance with an aspect of the present invention further includes the step of selecting, from the tobacco plants produced by the above producing step, an individual in which the number or weight of primary axillary buds is decreased to ½ or lower in comparison with a wild-type plant. This selecting step is carried out based on, for example, disruption, mutation, or suppressed expression of the at least two genes described above.

The mutation or disruption of the at least two genes is determined by identifying the presence/absence of a mutation of the gene. A method of identifying the mutation of the gene needs to allow the determination of the presence/absence of the mutation. Examples of the method encompass (1) a method in which a DNA sequence is directly decoded with use of a commercially available sequencer, (2) a method in which a difference in sequence is detected by a difference in distance of electrophoresis with use of the Single Strand Conformation Polymorphism (SSCP) method, (3) a method in which Single Nucleotide Polymorphism (SNP) is detected by the Cycleave PCR method, (4) a method in which the presence/absence of a mutation is identified by cleaving a mismatch site(s) with use of T7 Endonucleasel or the like, (5) a Cleaved Amplified Polymorphic Sequence (CAPS) method in which the presence/absence of a mutation can be determined by the presence/absence of cleavage by a restriction enzyme treatment, (6) a derived CAPS (dCAPS) method in which a set of primers including a mismatch is intentionally used so that the presence/absence of a mutation can be determined by the presence/absence of cleavage by restriction enzymes, (7) a method (e.g., a PCR method in which a TaqMan probe is used, MassARRAY analysis) in which the presence/absence of a mutation is determined by identifying, by use of a probe which specifically hybridizes to a mutant sequence, whether or not a probe is hybridized, and (8) a method in which, in a case where the mutation is deletion or insertion, a difference in length of PCR amplification fragments (double-stranded) of the gene is detected by a difference in mobility of electrophoresis. Alternatively, the mutation or disruption of a gene can be determined by detection (e.g., Western blotting) of (i) a polypeptide which results from modification of the gene or (ii) an expression level of a wild-type polypeptide.

Prior to the above-described step of introducing a mutation, procedures (1 and 2) described below are carried out as necessary so as to determine (i) a gene whose expression is to be suppressed and/or (ii) a gene into which a mutation is to be introduced.

1. Isolation of Tobacco Gene which is Predicted to Regulate Development of Axillary Bud A gene, which possibly regulates axillary buds, can be obtained from genes of tobacco by (i) selecting a gene from other plants based on a prior art document (e.g., Non-Patent Literature in which a relationship between a gene and an axillary bud is confirmed) and (ii) using, as an index, identity of nucleotide sequence and identity of amino acid sequence of the selected genes. For example, a nucleotide sequence and an amino acid sequence of a publicly-known tobacco gene or a gene of a plant species (e.g., tomato) which is closely related to tobacco can be obtained by conducting a search in sequences registered in a publicly-known database with use of Basic Local Alignment Search Tool (blast). In a case where a publicly-known sequence is of a partial length, a full-length cDNA can be obtained from known sequence information by a common method such as (i) screening from a cDNA library or (ii) Rapid amplification of cDNA ends (Race) method.

A gene, which possibly regulates an axillary bud in a novel manner, can be obtained by, for example, selecting a gene which is expressed according to a target tissue or a treatment. The target tissue and the treatment can be selected based on information listed below. It is known that (i) a gene, which is involved in the formation of an axillary meristem, is expressed prior to the formation of the axillary meristem and (ii) a gene, which is involved in maintenance and growth of an axillary meristem, is expressed at the axillary meristem (e.g., LS, Blind gene). It is known that a gene, which is involved in dormancy or development of an axillary bud, is expressed in an increased or decreased amount, depending on the dormancy or non-dormancy of the axillary bud (e.g., BRANCHED1). It is also known that some plant hormones are involved in the regulating of axillary buds. Auxin is involved in apical dominance. Strigolactone is involved in suppression of the development of axillary buds. Cytokinin is involved in outgrowth of axillary buds. Abscisic acid is involved in dormancy.

New selection of a gene which possibly regulates the development of an axillary bud can be performed by a common method in which expression specificity is utilized. The following (1) through (3) are examples of the method. (1) Methods such as (a) a method in which gene expression profiling data is obtained from a nucleotide sequence of cDNA, (b) a method in which a cDNA library of genes that are expressed in a subject tissue is prepared and then a terminal sequence is sequenced, and (c) a Serial Analysis of Gene Expression (SAGE) method in which restriction fragments are connected in series and sequenced. (2) A method in which gene expression profiling data is obtained by differential hybridization. Macro arrays and DNA chips are well known. (3) Genes (Differentially Expressed Genes: DEGs) which differ in expression level between a plurality of samples can be obtained by a differential display method. Examples encompass a method in which the amounts of PCR amplification fragments are compared.

Amplification of Isolated Genes

Amplification of a polynucleotide can be performed by Polymerase Chain Reaction (PCR), but alternatively can be performed by, for example, Ligase Chain Reaction (LCR) or Loop-Mediated Isothermal Amplification (LAMP).

A primer for amplifying a polynucleotide only needs to be a primer which enables specific amplification of a target gene of each genome from tobacco genomes in which genes of an S genome and a T genome are mixed. Provided that the target gene can be specifically amplified, one or more substitutions, deletions, insertions, and additions can be included. In addition, as necessary, the primer can be labeled with, for example, a fluorescent substance or a radiation.

Extraction of genomic DNA to be used as a template of the amplification can be performed by a publicly-known method, and can be performed by using a commercially available extraction kit. Genomic DNA can be a partially purified one obtained through simple extraction or can be a purified one obtained through a purification step.

2. Identification of Gene which is Expected to be Involved in Development of Axillary Bud Effects of a target gene can be confirmed by (i) preparing recombinants and mutants in which expressions and functions of the target gene are suppressed and (ii) cultivating the recombinants and the mutants in a greenhouse, a phytotron, a semi-containment greenhouse, or a field. By comparing the number and weight of developed axillary buds with the controls, it is possible to confirm effects of the outgrowth and development of axillary buds. While the number and weight of the axillary buds can be performed without performing topping, the number and weight of the axillary buds is preferably performed while (i) the axillary buds are in a non-dormancy state due to topping and (ii) the development of the axillary buds are therefore promoted. Examination of the number and weight of the axillary buds can be performed once or more than once in any season. In a case where the examinations are performed a plurality of times, it is preferable to perform examinations at intervals. For example, it is possible to carry out the following method once each week: to count the number of primary axillary buds, collect the primary axillary buds, and examine the weight of the primary axillary buds.

The examination can be performed with the focus only on specific axillary buds (e.g., primary axillary buds), or the examination can be performed such that examination with the focus only on the number of axillary buds and examination with the focus only on the weight are separately performed. In such a case, it is preferable that a suitable number of times of examinations and suitable intervals between the examinations are determined according to each examination.

[3. Other Remarks]

Another aspect of the present invention provides a method of determining a tobacco plant in which the development of primary axillary buds is suppressed. The suppression of the primary axillary buds is caused by introducing a mutation which causes functional suppression of the above-described at least two genes in a tobacco plant. It should be noted that the above functional suppression is to suppress the development of primary axillary buds. That is, the determining method can be used for, for example, a method of producing a tobacco plant. Therefore, for details of the determining method, a reference can be made to the previous descriptions regarding the method of producing the tobacco plant.

In addition, other aspects of the present invention provide (1) a leaf tobacco harvested from (i) the tobacco plant, (ii) a tobacco plant obtained by the production method described above; (iii) a tobacco plant determined by the determining method described above; (iv) a tobacco plant obtained by the breeding method; or (v) the offspring or the bred progeny described above, (2) a cured tobacco obtained from the leaf tobacco, and (3) a tobacco product obtained from the cured tobacco. Therefore, reference can be made to the previous descriptions for the details of the tobacco plant and the tobacco plant production method for obtaining (1) the leaf tobacco, (2) the cured tobacco, and (3) the tobacco product.

[4. Nucleic Acid Molecule]

Another aspect of the present invention provides an isolated nucleic acid molecule which can be used in any aspect described above. Concrete examples of the nucleic acid molecule encompass isolated nucleic acid molecules (1) through (6) below.

(1) a nucleic acid molecule including: a polynucleotide (a) encoding a polypeptide having a sequence identity of 90% or higher with an amino acid sequence represented by SEQ ID NO: 1; or a polynucleotide (b) complementary to a polynucleotide which hybridizes with the polynucleotide (a) under stringent conditions;

(2) a nucleic acid molecule including: a polynucleotide (c) encoding a polypeptide having a sequence identity of 90% or higher with an amino acid sequence represented by SEQ ID NO: 2; or a polynucleotide (d) complementary to a polynucleotide which hybridizes with the polynucleotide (c) under stringent conditions;

(3) a nucleic acid molecule including: a polynucleotide (e) encoding a polypeptide having a sequence identity of 90% or higher with an amino acid sequence represented by SEQ ID NO: 3; or a polynucleotide (f) complementary to a polynucleotide which hybridizes with the polynucleotide (e) under stringent conditions;

(4) a nucleic acid molecule including: a polynucleotide (g) encoding a polypeptide having a sequence identity of 90% or higher with an amino acid sequence represented by SEQ ID NO: 4; or a polynucleotide (h) complementary to a polynucleotide which hybridizes with the polynucleotide (g) under stringent conditions;

(5) a nucleic acid molecule including: a polynucleotide (i) encoding a polypeptide having a sequence identity of 90% or higher with an amino acid sequence represented by SEQ ID NO: 5; or a polynucleotide (j) complementary to a polynucleotide which hybridizes with the polynucleotide (i) under stringent conditions; and (6) a nucleic acid molecule including: a polynucleotide (k) encoding a polypeptide having a sequence identity of 90% or higher with an amino acid sequence represented by SEQ ID NO: 6; or a polynucleotide (l) complementary to a polynucleotide which hybridizes with the polynucleotide (k) under stringent conditions.

Another example of the nucleic acid molecule is a nucleic acid molecule which is isolated from a genome of the *Nicotiana* plant described in the item 1. Examples of the nucleic acid molecule, which are more concrete examples than the nucleic acid molecules (1) through (6), encompass NtLOM1 through NtLOM3 present in each of S genome and T genome discussed in Examples (described later). Therefore, the nucleic acid molecule is a coding region or a full length of each gene present in a genome of the *Nicotiana* plant. For example, the nucleic acid molecule can be isolated by identifying, according to a publicly-known method in the technical field concerned, a sequence of a polynucleotide having a sequence identity of 90% or higher with a polynucleotide represented by any one of SEQ ID NOs: 7, 8, 9, 10, 11, and 12. For example, the nucleic acid molecule can be isolated by identifying, according to a publicly-known method in the technical field concerned, a sequence of a polynucleotide encoding a polypeptide having a sequence identity of 90% or higher with a polypeptide represented by any one of SEQ ID NOs: 1, 2, 3, 4, 5, and 6.

(Recap)

With the above embodiments considered together, the present invention can be summarized as follows.

A tobacco plant in which a mutation causing functional suppression of at least two genes of the following genes (1) through (3) is introduced into a genome:

(1) at least one of: a gene containing, as a coding region, a polynucleotide (a) or a polynucleotide (b); and a gene containing, as a coding region, a polynucleotide (c) or a polynucleotide (d);

(2) at least one of: a gene containing, as a coding region, a polynucleotide (e) or a polynucleotide (f); and a gene containing, as a coding region, a polynucleotide (g) or a polynucleotide (h); and (3) at least one of: a gene containing, as a coding region, a polynucleotide (i) or a polynucleotide (j); and a gene containing, as a coding region, a polynucleotide (k) or a polynucleotide (l), the functional suppression suppressing development of primary axillary buds, the polynucleotide (a) being a polynucleotide encoding a polypeptide having a sequence identity of 90% or higher with an amino acid sequence represented by SEQ ID NO: 1, the polynucleotide (b) being a polynucleotide complementary to a polynucleotide which hybridizes with the polynucleotide (a) under stringent conditions, the polynucleotide (c) being a polynucleotide encoding a polypeptide having a sequence identity of 90% or higher with an amino acid sequence represented by SEQ ID NO: 2, the polynucleotide (d) being a polynucleotide complementary to a polynucleotide which hybridizes with the polynucleotide (c) under stringent conditions, the polynucleotide (e) being a polynucleotide encoding a polypeptide having a sequence identity of 90% or higher with an amino acid sequence represented by SEQ ID NO: 3, the polynucleotide (f) being a polynucleotide complementary to a polynucleotide which hybridizes with the polynucleotide (e) under stringent conditions, the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

In the tobacco plant, the functional suppression preferably causes the number or weight of the primary axillary buds to decrease to not more than ½ of that of a wild-type plant.

In the tobacco plant, the functional suppression is preferably a decrease, as compared with a wild-type plant, in abundance of the polypeptides which are expression products of the at least two genes.

In the tobacco plant, the functional suppression is preferably a decrease, as compared with a wild-type plant, in an amount of translation of the polypeptides which are expression products of the at least two genes.

In the tobacco plant, the functional suppression is preferably a decrease, as compared with a wild-type plant, in an amount of transcription from the at least two genes to mRNA.

In the tobacco plant, the functional suppression is preferably promotion of degradation of mRNAs transcribed from the at least two genes.

In the tobacco plant, the mutation is preferably introduced into each of the at least two genes.

In the tobacco plant, the mutation is preferably introduced by spontaneous mutation, mutagen treatment, gene recombination, genome editing, or gene knockout.

In the tobacco plant, the mutation is preferably insertion, into an outside of a region in which the genes are present, of a polynucleotide expressing a factor which promotes the degradation of the mRNA.

In tobacco plant, the factor is preferably an antisense RNA molecule, an RNAi molecule, or a co-suppression molecule.

In the tobacco plant, the tobacco plant preferably belongs to *Nicotiana tabacum* or *Nicotiana rustica*.

A method of producing a tobacco plant, including the step of:

(A) introducing, into a genome of a tobacco plant, a mutation causing functional suppression of at least two genes of the following genes (1) through (3):
(1) at least one of: a gene containing, as a coding region, a polynucleotide (a) or a polynucleotide (b); and a gene containing, as a coding region, a polynucleotide (c) or a polynucleotide (d);
(2) at least one of: a gene containing, as a coding region, a polynucleotide (e) or a polynucleotide (f); and a gene containing, as a coding region, a polynucleotide (g) or a polynucleotide (h); and
(3) at least one of: a gene containing, as a coding region, a polynucleotide (i) or a polynucleotide (j); and a gene containing, as a coding region, a polynucleotide (k) or a polynucleotide (l),
the functional suppression suppressing development of primary axillary buds,
the polynucleotide (a) being a polynucleotide encoding a polypeptide having a sequence identity of 90% or higher with an amino acid sequence represented by SEQ ID NO: 1,
the polynucleotide (b) being a polynucleotide complementary to a polynucleotide which hybridizes with the polynucleotide (a) under stringent conditions,
the polynucleotide (c) being a polynucleotide encoding a polypeptide having a sequence identity of 90% or higher with an amino acid sequence represented by SEQ ID NO: 2,
the polynucleotide (d) being a polynucleotide complementary to a polynucleotide which hybridizes with the polynucleotide (c) under stringent conditions,
the polynucleotide (e) being a polynucleotide encoding a polypeptide having a sequence identity of 90% or higher with an amino acid sequence represented by SEQ ID NO: 3,
the polynucleotide (f) being a polynucleotide complementary to a polynucleotide which hybridizes with the polynucleotide (e) under stringent conditions,
the polynucleotide (g) being a polynucleotide encoding a polypeptide having a sequence identity of 90% or higher with an amino acid sequence represented by SEQ ID NO: 4,
the polynucleotide (h) being a polynucleotide complementary to a polynucleotide which hybridizes with the polynucleotide (g) under stringent conditions,
the polynucleotide (i) being a polynucleotide encoding a polypeptide having a sequence identity of 90% or higher with an amino acid sequence represented by SEQ ID NO: 5,
the polynucleotide (j) being a polynucleotide complementary to a polynucleotide which hybridizes with the polynucleotide (i) under stringent conditions,
the polynucleotide (k) being a polynucleotide encoding a polypeptide having a sequence identity of 90% or higher with an amino acid sequence represented by SEQ ID NO: 6, and
the polynucleotide (l) being a polynucleotide complementary to a polynucleotide which hybridizes with the polynucleotide (k) under stringent conditions.

The tobacco plant production method preferably further includes the step of: (B) selecting, from individuals produced by the step (A), an individual in which development of the primary axillary buds is suppressed.

In the tobacco plant production method, in the step (B), an individual, in which the number or weight of the primary axillary buds is decreased in comparison with that of a wild-type plant, is preferably selected.

In the tobacco plant, in the step (A) preferably includes introducing the mutation into each of the at least two genes.

In the tobacco plant production method, the step (A) is preferably carried out by spontaneous mutation, mutagen treatment, gene recombination, genome editing, or gene knockout.

In the tobacco plant production method, the step (A) preferably includes inserting, into an outside of a region in which the at least two genes are present, a polynucleotide expressing a factor which promotes the degradation of the mRNAs transcribed from the at least two genes.

In the tobacco plant production method, the factor is preferably an antisense RNA molecule, an RNAi molecule, or a co-suppression molecule.

A method of determining a tobacco plant in which development of primary axillary buds is suppressed, the method including the steps of:

(A) obtaining a sample by collecting a part of a tobacco plant;

(B) detecting, from a genome included in the sample, a mutation causing functional suppression of at least two genes of the following genes (1) through (3) on the genomic DNA:
   (1) at least one of: a gene containing, as a coding region, a polynucleotide (a) or a polynucleotide (b); and a gene containing, as a coding region, a polynucleotide (c) or a polynucleotide (d);
   (2) at least one of: a gene containing, as a coding region, a polynucleotide (e) or a polynucleotide (f); and a gene containing, as a coding region, a polynucleotide (g) or a polynucleotide (h); and
   (3) at least one of: a gene containing, as a coding region, a polynucleotide (i) or a polynucleotide (j); and a gene containing, as a coding region, a polynucleotide (k) or a polynucleotide (l); and (C) determining that a tobacco plant, in which the mutation has been detected, is a tobacco plant in which the development of the primary axillary buds is suppressed,
the polynucleotide (a) being a polynucleotide encoding a polypeptide having a sequence identity of 90% or higher with an amino acid sequence represented by SEQ ID NO: 1,
the polynucleotide (b) being a polynucleotide complementary to a polynucleotide which hybridizes with the polynucleotide (a) under stringent conditions,
the polynucleotide (c) being a polynucleotide encoding a polypeptide having a sequence identity of 90% or higher with an amino acid sequence represented by SEQ ID NO: 2,
the polynucleotide (d) being a polynucleotide complementary to a polynucleotide which hybridizes with the polynucleotide (c) under stringent conditions,
the polynucleotide (e) being a polynucleotide encoding a polypeptide having a sequence identity of 90% or higher with an amino acid sequence represented by SEQ ID NO: 3,
the polynucleotide (f) being a polynucleotide complementary to a polynucleotide which hybridizes with the polynucleotide (e) under stringent conditions,
the polynucleotide (g) being a polynucleotide encoding a polypeptide having a sequence identity of 90% or higher with an amino acid sequence represented by SEQ ID NO: 4, the polynucleotide (h) being a polynucleotide complementary to a polynucleotide which hybridizes with the polynucleotide (g) under stringent conditions, the polynucleotide (i) being a polynucleotide encoding a polypeptide having a sequence identity of 90% or higher with an amino acid sequence represented by SEQ ID NO: 5, the polynucleotide (j) being a polynucleotide complementary to a polynucleotide which hybridizes with the polynucleotide (i) under stringent conditions, the polynucleotide (k) being a polynucleotide encoding a polypeptide having a sequence identity of 90% or higher with an amino acid sequence represented by SEQ ID NO: 6, and the polynucleotide (l) being a polynucleotide complementary to a polynucleotide which hybridizes with the polynucleotide (k) under stringent conditions.

A method of breeding a tobacco plant, including the step of: crossing the tobacco plants which are determined by the determining method as tobacco plants in which development of primary axillary buds is suppressed.

An offspring or a bred progeny, in which: the offspring is of (i) the tobacco plant, (ii) the tobacco plant produced by the production method; (iii) the tobacco plant determined by the determining method; or (iv) the tobacco plant bred by the breeding method; and the bred progeny is obtained by crossing (i) the tobacco plant, (ii) the tobacco plant produced by the production method; (iii) the tobacco plant determined by the determining method; or (iv) the tobacco plant bred by the breeding method.

A leaf tobacco harvested from (i) the tobacco plant, (ii) the tobacco plant produced by the production method; (iii) the tobacco plant determined by the determining method; (iv) the tobacco plant obtained by the breeding method; or (v) the offspring or the bred progeny.

A cured tobacco obtained from the leaf tobacco.

A tobacco product obtained from the cured tobacco.

EXAMPLES

[1. Candidate Gene Involved in Development of Axillary Buds of Tobacco Plant]

(a) Blast Analysis

With an amino acid sequence of LOM1 gene of *Arabidopsis thaliana* serving as a query sequence, tblastn search was conducted on a web page of NCBI (http://blast.ncbi.nlm.nih.gov/Blast.cgi). As a result, from each of genome sequence databases (whole genome shotgun contigs (wgs)) of *Nicotiana sylvestris* and *Nicotiana tomentosiformis*, the following were obtained: (i) two gene sequences (ASAF01021035, ASAG01097213) having an amino acid identity of 54%; and (ii) two gene sequences (ASAF01015857, ASAG01076972) having an amino acid identity of 41%. Meanwhile, similar sequences were obtained also from tblastn search with respect to results of analysis of Expressed Sequence Tag (EST)) of cDNA library (derived from axillary buds of SR-1).

(b) Preparation of cDNA and Isolation of LOM Gene

Total RNA was extracted as follows. A shoot apex, a seedling, and an axillary bud of tobacco (SR-1) were each immersed in RNAlater (Ambion), and then cryopreserved. Then, these samples were thawed, and then 0.5 ml of an RTL buffer (QIAGEN), to which 20 µl of 1 M DTT had been added, was added to the thawed sample. A resultant mixture was ground (2500 rpm, 1 minute) with use of Multi Beads Shocker (Yasui Kikai Corporation). The homogenate after the grinding was subjected to centrifugal separation (15000 rpm, 10 minutes), so that a supernatant was obtained. From the supernatant, total RNA was purified with use of Magtration (Precision System Science Co., Ltd.) or RNeasy Kit (QIAGEN), in the presence of DNase.

From the total RNA, cDNA was prepared with use of any one of the following kits according to the manual included in the kit.

PrimeScript II 1st strand cDNA Synthesis Kit (Takara-Bio Inc.)

PrimeScript RT reagent kit with gDNA Eraser (Takara-Bio Inc.)

With use of total RNA extracted as described above and SMARTer RACE cDNA Amplification Kit (Clonetech), cDNA was synthesized, and Race was performed according to the manual included in the kit. For nested PCR of the Race, 1st PCR products, which had been 300-fold diluted, were used as a template. The reaction conditions in the Race were set as follows.

(1st PCR)

5 cycles while each cycle includes 10 seconds at 98° C. and 10 seconds at 72° C.

5 cycles while each cycle includes 10 seconds at 98° C., 5 seconds at 70° C., and 5 seconds at 72° C.

25 cycles while each cycle includes 10 seconds at 98° C., 5 seconds at 60° C., and 5 seconds at 72° C.

(Nested PCR)

25 cycles while each cycle includes 10 seconds at 98° C., 5 seconds at 55° C., and 5 seconds at 72° C.

As primers for the Race, primers included in the kit and primers specific to the following genes were used.

```
(NtLOM1)
LOM1_5R-1:
                                          (SEQ ID NO: 19)
ACCCATCCAAGACCTCAAGCAGGGCT

LOM_5R-nest1:
                                          (SEQ ID NO: 20)
TGATTGAGCCGCGCCAATATC (NtLOM2 and NtLOM3)
LOM2_5R-1:
                                          (SEQ ID NO: 21)
GGCCTTATAAGCATCCATCTTAAGCACAC LOM_5R-nest1:
                                          (SEQ ID NO: 20)
TGATTGAGCCGCGCCAATATC
```

RT-PCR was performed while the above-described cDNA was used as a template. In a case where PrimeSTAR Max DNA Polymerase (Takara-Bio Inc.) was used as an enzyme, the reaction conditions were set as follows. 30 seconds at 94° C. 30 cycles to 40 cycles while each cycle includes 10 seconds at 98° C., 5 seconds at 55° C., and 10 seconds at 72° C. 10 seconds at 72° C.*

*An extension reaction at 72° C. was set to 10 seconds per kb of the length of an amplification fragment.

In a case where Tks Gflex DNA Polymerase (Takara-Bio Inc.) was used as an enzyme, the reaction conditions were set as follows.

30 seconds at 94° C.

30 cycles to 40 cycles while each cycle includes 10 seconds at

98° C., 15 seconds at 55° C., and 60 seconds at 68° C.

60 seconds at 68° C.*

*An extension reaction at 68° C. was set to 60 seconds per kb of the length of an amplification fragment.

Combinations of a target gene and a primer for RT-PCR are as follows.

```
NtLOM1
S genome gene
LOM1_RT-F1:
                                    (SEQ ID NO: 22)
AGAAAGAAGTCATTTTGTGGACTG LOM1-1_RT-R1:
                                    (SEQ ID NO: 23)
GAATGTTGGATTGTTCACCG T genome gene
LOM1_RT-F1:
                                    (SEQ ID NO: 22)
AGAAAGAAGTCATTTTGTGGACTG LOM1-2_RT-R1:
                                    (SEQ ID NO: 24)
GTTTGATTGTTCTTATAACACCGA NtLOM2
S genome gene
LOM2_RT-F1:
                                    (SEQ ID NO: 25)
CTATGTTCAGATGATTGTAATACCTCA LOM2_RT-R1:
                                    (SEQ ID NO: 26)
ACACATAAGGAGAAAATGACGC NtLOM2-2-1_F1:
                                    (SEQ ID NO: 27)
TTCAGATGATTGTAATACCTCAAAGT NtLOM2-2-1_R1:
                                    (SEQ ID NO: 28)
AACACACTGATATTTAAACAGGGA T genome gene
NtLOM2-1-1_F1:
                                    (SEQ ID NO: 29)
TTTGTAGTGGGTTTAGCTGATTT NtLOM2-1-1_R1:
                                    (SEQ ID NO: 30)
ACACATACGGAGAAAATGACATAG NtLOM3
S genome gene
LOM2_RT-F1:
                                    (SEQ ID NO: 25)
CTATGTTCAGATGATTGTAATACCTCA LOM2_RT-R2:
                                    (SEQ ID NO: 31)
ACAGGCAATAGTGGAGGTGATA NtLOM2-2-2_F1:
                                    (SEQ ID NO: 32)
ACCTCAATGTATTCCTAAATCCTAAC NtLOM2-2-2_R1:
                                    (SEQ ID NO: 33)
TCTGTTTACACGTAGGAATGCTT T genome gene
NtLOM2-1-2_F1:
                                    (SEQ ID NO: 34)
CTATGTTCAGATGATTGTAATACCTC NtLOM2-1-2_R1:
                                    (SEQ ID NO: 35)
ATGCTGAAAGATACTACGCAGATT
```

(b) Preparation of Genomic DNA Fragment and Isolation of LOM Gene

Genomic DNA fragments were extracted from leaves of tobacco (SR-1)) according to a simple extraction method or a CTAB method. The CTAB method is publicly known, and therefore will not be described in detail. The simple extraction method was carried out according to the following procedure. A leaf segment, which was placed in 0.3 ml to 0.5 ml of extraction buffer (0.2 M Tris-HCl pH 8.0, 0.4 M NaCl, 25 mM EDTA, and 0.5% SDS), was ground (2500 rpm, 1 minute) with use of Multi Beads Shocker (Yasui Kikai Corporation). A supernatant is taken from a homogenate after the grinding. Then, genomic DNA fragments are purified from the supernatant through ethanol precipitation.

By genomic PCR in which the genomic DNA fragment described above was used as a template, three genes were amplified. Since the enzymes used and the reaction conditions used for the enzymes are similar to those in the RT-PCR, combinations of a target gene and a primer are as follows.

```
NtLOM1
S genome gene
LOM1_RT-F1:
                                    (SEQ ID NO: 22)
AGAAAGAAGTCATTTTGTGGACTG LOM1-1_RT-R1:
                                    (SEQ ID NO: 23)
GAATGTTGGATTGTTCACCG T genome gene
LOM1_RT-F1:
                                    (SEQ ID NO: 22)
AGAAAGAAGTCATTTTGTGGACTG LOM1-2_RT-R1:
                                    (SEQ ID NO: 24)
GTTTGATTGTTCTTATAACACCGA NtLOM2
S genome gene
NtLOM2-2-1_F1:
                                    (SEQ ID NO: 27)
TTCAGATGATTGTAATACCTCAAAGT NtLOM2-2-1_R1:
                                    (SEQ ID NO: 28)
AACACACTGATATTTAAACAGGGA T genome gene
NtLOM2-1-1_F1:
                                    (SEQ ID NO: 30)
TTTGTAGTGGGTTTAGCTGATTT NtLOM2-1-1_R1:
                                    (SEQ ID NO: 28)
ACACATACGGAGAAAATGACATAG NtLOM3
S genome gene
NtLOM2-2-2_F1:
                                    (SEQ ID NO: 32)
ACCTCAATGTATTCCTAAATCCTAAC NtLOM2-2-2_R1:
                                    (SEQ ID NO: 33)
TCTGTTTACACGTAGGAATGCTT T genome gene
NtLOM2-1-2_F1:
                                    (SEQ ID NO: 34)
CTATGTTCAGATGATTGTAATACCTC NtLOM2-1-2_R1:
                                    (SEQ ID NO: 35)
ATGCTGAAAGATACTACGCAGATT
```

(d) Determination of Sequence of Genes Obtained

Each of the PCR products, which were obtained by amplifying the three genes, were cloned with use of Zero Blunt TOPO PCR Cloning Kit for Sequencing Kit (Life Technologies Corporation). As necessary, the PCR products were purified before the cloning by a common method in which agarose gel electrophoresis and MiniElute column (QIAGEN) were combined. The respective nucleotide sequences of the cloned DNAs were determined by a capillary sequencer 3730×1 DNA Analyzer (ABI) with use of BigDye (registered trademark) Terminator v3.1 Cycle Sequencing Kit (ABI). The sequence primer was designed as appropriate from sequence information and was used.

(e) Results

The three candidate genes determined from the gene isolation and sequence analysis were named NtLOM1 through NtLOM3.

[2. Preparation of Plants Having Functional Suppression of Candidate Genes]

For the purpose of examining the effects of functional suppression of NtLOM1 through NtLOM3 on the development of axillary buds of the tobacco plants, the following were prepared: (i) recombinant tobacco plants having suppressed expression of NtLOM1 through NtLOM3 were prepared (hereinafter referred to simply as "recombinant(s)") and (ii) tobacco plants in which mutations were introduced into structural genes of NtLOM1 through NtLOM3 (hereinafter referred to simply as "mutant(s)").

(2-1. Preparation of Recombinants)

(a) Preparation for Transformation

In order to prepare the recombinants, vectors for transformation were first prepared as described below.

The primers for PCR amplification of RNAi trigger sequences (1) through (3) were designed so that (i) a 5' end side was added with CCAC and (ii) the RNAi trigger sequences had lengths of 270 bp to 500 bp. The following RNAi trigger sequences (1) through (3) were amplified by PCR in which PrimeSTAR Max DNA Polymerase (Takara-Bio Inc.) was used, while cDNA derived from SR-1 produced based on the results of the item 1. was used as a template: an RNAi trigger sequence (1) for suppressing expression of NtLOM2 and NtLOM3; an RNAi trigger sequence (2) for suppressing expression of NtLOM1; and an RNAi trigger sequence (3) for suppressing expression of NtLOM2. The conditions of PCR, the combination of primers, and RNAi trigger sequences thus obtained are as follows.

(Conditions of PCR)

30 seconds at 94° C.

30 cycles to 40 cycles while each cycle includes 10 seconds at

98° C., 5 seconds at 55° C., and 10 seconds at 72° C.

10 seconds at 72° C.

(Primer for RNAi trigger sequence (1))
LOM2_Tr_F1:
(SEQ ID NO: 36)
CACCTCCAATCAAGCTATTCTTG LOM2_Tr_R1:
(SEQ ID NO: 37)
GTATCTCATAATATTGGAGGGCGT (Primer for RNAi trigger sequence (2))
LOM1_Tr_F1:
(SEQ ID NO: 38)
CACCAGCTATTCAAAGCTGCAG LOM1_Tr_R1:
(SEQ ID NO: 39)
AACTTTCTCTAGTGAGTCCAAGCTC (Primer for RNAi trigger sequence (3))
D-NsSCL22_F1:
(SEQ ID NO: 40)
CACCCCTAGCAGGAGCAAAAGGG NsSCL22_R3:
(SEQ ID NO: 41)
ATGGCTGCAGCTCAGTAACC (RNAi trigger sequence (1))
(SEQ ID NO: 42)
CACCTCCAATCAAGCTATTCTTGAAGCTCTTGGGGATGCCAAG

CAAATTCACATAATAGATTTTGACATTGGCTGTGGTGCTCAATG

GTCCTCATTTATGCAAGAACTCCCGAGCAGCAATAGAAAGGCA

ACTTCTCTAAAGATTACTGCCTTTGTATCTCCTTCAACCCACCA

CTCCGTTGAGATTGGCATCATGCACGAAAGTTTAACGCTGTTTG

CTAATGATGTGGGAATCAGATTTGAGCTGGAAGTTATTAACTTG

GATTCCTTTGACCCTAAGACTTATCCCTTATCCTCCTTGAGGTC

ATCTGAGTGTGAGGCTATTGCTATTAATTTCCCCATCTGGTCTA

TTTCAAGTTGTCTATTTGCATTTCCTTCACTTCTTCACTGTATGA

AGCAGCTTTCACCAAAAGTTGTTGTATCATTGGAACGTGGATGT

GAACGTACTGAACTCCCCTTAAAGCATCACCTCCTCCACGCCC

TCCAATATTATGAGATAC (RNAi trigger sequence (2))
(SEQ ID NO: 43)
CACCAGCTATTCAAAGCTGCAGAGCTGGTCCAGACAGGGAATC

CAGTACTCGCGCAAGGGATATTGGCGCGGCTCAATCACCAGCT

CTCTCCAATTGGTAAGCCTTTCTATAGGGCTGCTTTTTATTGCA

AGGAAGCTTTACAATTGCTACTTCATACCAACACCAACAACTTG

AACAACCCCTCTATACCATCTTCTTCACCTTTTAATCTCATCTTC

AAGATTGGTGCCTATAAGTCCTTCTCTGAGATCTCACCAGTTGC

ACAGTTTGCTAATTTCACTTGTAACCAAGCCCTGCTTGAGGTCT

TGGATGGGTTTGAAAGAATTCATATTGTTGATTTTGATATCGGC

TATGGCAGGCAATGGGCTTCTCTTATGCAAGAGCTTGCCTTGA

GAAGTGGTGGCGCACCTACCCTGAAAATAACTGCATTGGCCTC

ACCCTCCACACATGACCAACTAGAGCTTGGACTCACTAGAGAA

AGTT (RNAi trigger sequence (3))
(SEQ ID NO: 44)
CACCCCTAGCAGGAGCAAAAGGGGTACTTGGTGTTTCAGGTTA

TGTACCTTCAATTTCTTCTTCACCAGAAGCAGCAATTTGTAATAA

AGGTTTAAACTTTACAAGAAACGAATCTGTCTCAGTGTTGGATG

CAAGAAGTCCTAGTCCTTCAGCTTCATCTTCCTCGTGTTCTTAT

GGTGGACAATATGCTGGAAATAATGGAGTTCCCGGCGCCGGA

GCTGGAAAAATTGACGGCCGGAAAGAGGAGTTGGTTACTGAGC

TGCAGCCAT

The lower-case letter(s) c(2) or cacc(3) at the 5' end were artificially added for constructing a vector.

The PCR products were cloned to pENTR (trademark)/ D-TOPO vectors (Life Technologies Corporation). Then, the nucleotide sequence of each RNAi trigger sequence was checked. Then, with use of Gateway LR Clonase II Enzyme Mix (Life Technologies Corporation), each RNAi trigger sequence was introduced into a pSP231 vector. The pSP231 vector is a vector in which a GFP (Green-fluorescent protein gene) expression cassette was inserted into a SacI site of pHellsgate 12 (see Wesley et al., 2001, Plant J., 27, 581-590). In addition, the pSP231 vector is a binary vector which can express, with a cauliflower mosaic virus 35S RNA gene promoter, a RNAi sequence formed with a pdk/cat intron located between inverted repeat sequences of the RNAi trigger sequence. In order to check the sequence introduced into the pSP231 vector, a sense strand and an antisense strand of each RNAi trigger sequence were individually amplified by PCR in which TakaRa Ex Taq and PrimeSTAR Max DNA Polymerase (Takara-Bio Inc.) were used. The PCR products were purified with use of MiniElute (QIAGEN), and then subjected to sequencing. By use of a sequencer, it was confirmed that the RNAi trigger sequence (1), (2), or (3) described above was introduced into the pSP231 vector.

With use of the pSP231 vector containing the RNAi trigger sequence, Agrobacterium (Agrobacterium tumefaciens) LBA4404 was transformed by electroporation. After it was confirmed by PCR that each RNAi trigger sequence was amplified in LBA4404, the Agrobacterium was used for the transformation of tobacco.

(b) Transformation of Tobacco and Collection of Transformed Seeds

The tobacco (variety: SR-1) was transformed according to a common method as described below. A section of a tobacco leaf was infected with the Agrobacterium thus transformed, and was cultured in Linsmaier and Skoog medium containing kanamycin, so that calluses were obtained. From the calluses thus obtained, redifferentiated individuals, which are kanamycin-resistant, were obtained. From these redifferentiated individuals, the following individuals were selected: the individual in which (i) intense fluorescence based on GFP in the entire leaf was confirmed and (ii) high-level expression at a spacer portion (PPDK intron) was confirmed. The individuals thus selected (T0 individuals) were transplanted to 9-cm pots, and were cultivated under fixed conditions in a containment greenhouse at 23° C. to 25° C. The T0 individuals were selfed, so that T1 seeds were collected.

(c) Selection of T1 Recombinants

First, the T1 seeds were aseptically sowed in Linsmaier and Skoog medium, and fluorescence based on GFP of seedling was observed. Based on the results of the observation, individuals were selected, which were predicted to be (i) individuals having homozygous mutations (hereinafter simply referred to as "homo") as a result of the transformation and (ii) individuals having no mutation (hereinafter simply referred to as "null") as a result of the transformation.

By qPCR in which total RNA isolated from a leaf of a T1 line individual was used, the expression levels of NtLOM1 through NtLOM3 were determined. The details of the qPCR are as follows.

Sigma-Aldrich Japan was requested to perform designing of the primers and probes of the qPCR. As described in (b) of the item 1., cDNA was synthesized from total RNA isolated from the leaf. The qPCR was performed with use of (i) cDNA which was 2 to 5-fold diluted, (ii) the primers obtained as described above, and (iii) Taq Man Fast Advanced Master Mix (ABI). As a quantification reference, eukaryotic elongation factor-1a gene (accession No. AF120093, efla) was amplified. As a quantification probe, a combination of reporter dye and quencher (FAM-TAMURA (gene to be analyzed) and VIC-TAMURA (reference)) was used. In the sequence targeting each gene below, the first is a forward primer, the second is a reverse primer, and the third is a probe.

(NtLOM2 and NtLOM3 (Common))

```
Common for NtLOM2 and NtLOM3 (FIG. 2)
LOM2-1-F:
                                        (SEQ ID NO: 45)
CGAGAAGCGCCAGACGTCA LOM2-1-R:
                                        (SEQ ID NO: 46)
TGTTGTTGTTAAAAGAAAGAGTCATCA LOM2-1-P:
                                        (SEQ ID NO: 47)
AGCAGCAGGAACTCTTGTCAGCTTTGTCTT NtLOM2 (FIGS. 3, 4, and 10)
S genome gene
NtLOM2_S-F:
                                        (SEQ ID NO: 48)
CCCATCAGTTAGCTTGAAACAAC NtLOM2_S-R:
                                        (SEQ ID NO: 49)
TTATTTGAGTCAATGACAACAGAACC NtLOM2_S-P:
                                        (SEQ ID NO: 50)
AAGAACCTGCAACTGAAACTCCACAACCCA T genome gene
NtLOM2_T-F:
                                        (SEQ ID NO: 51)
CCCATCAGTCAGCTTGAAACAA NtLOM2_T-R:
                                        (SEQ ID NO: 52)
TGTTTGAGTCTATGACAGCATAACC NtLOM2_T-P:
                                        (SEQ ID NO: 53)
AGAACCTGCCACTGAAACTCCACCACCC NtLOM3 (FIGS. 3, 4, and 10)
S genome gene
NtLOM3_S-F:
                                        (SEQ ID NO: 54)
CTTAAGCGCACTATTGCCTGAG NtLOM3_S-R:
                                        (SEQ ID NO: 55)
CCTCAAGCTTAGGTACAATTAATGGT NtLOM3_S-P:
                                        (SEQ ID NO: 56)
CTTGCTGCCGCGTTTGTCCCAATG T genome gene
NtLOM3_T-F:
                                        (SEQ ID NO: 57)
GCTTAAGTGCTCTATTGCCTGAA NtLOM3_T-R:
                                        (SEQ ID NO: 58)
TCAAGCTTAGGTACAATTAATGGCT NtLOM3_T-P:
                                        (SEQ ID NO: 59)
CTTGCTGCCGCATTTGTCCCAATGG
```

-continued (NtLOM1)
Common for S genome and T genome (FIG. 1)
LOM1-F:
(SEQ ID NO: 60)
CTACCATTTCCAAACCATGTAATTCAA

LOM1-R:
(SEQ ID NO: 61)
CTCTCAATTCTTGGTTGGAGCA

LOM1-P:
(SEQ ID NO: 62)
CTCAAACCTTCTTGAGTCGTTAGATGCCGT

Figure 2:
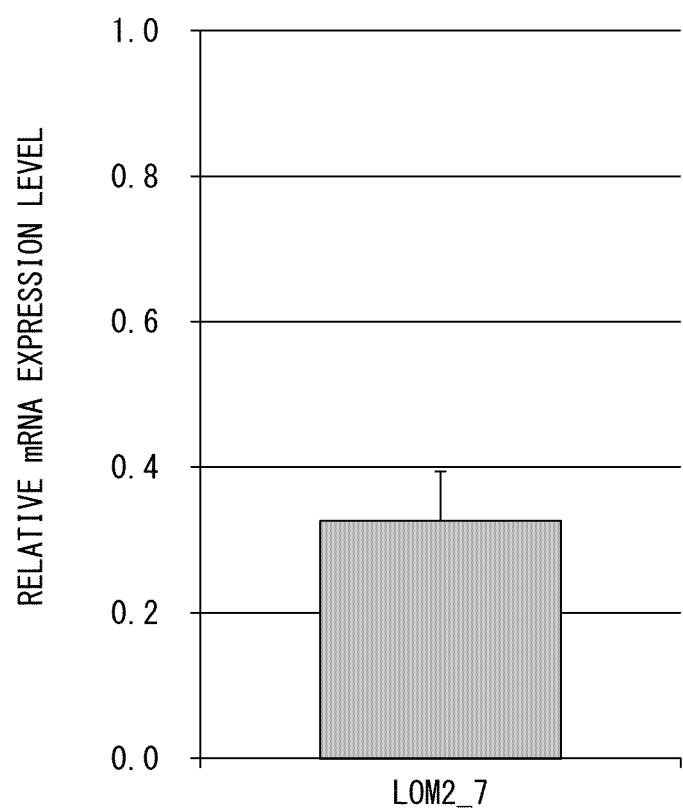
FIG. 2 is a view showing the results of determining mRNA expression level of NtLOM2 and NtLOM3 in a tobacco plant (T1 individual).

Based on the results of qPCR, the expression levels of NtLOM1 through NtLOM3 were each calculated as a ratio of the expression level in homo lines to the expression level in null lines when the expression level in null lines is set as 1. FIG. 1 is a view showing the results of determining the mRNA expression level of NtLOM1. FIG. 2 is a view showing the results of determining the mRNA expression level of NtLOM2 and NtLOM3. Note that FIGS. 1 and 2 show only the results of the lines selected as target recombinants.

As shown in FIG. 1, the lines 11, 20, and 24 related to NtLOM1 each exhibited an expression level lower than ½ of that of the null line. As shown in FIG. 2, the line 7 related to NtLOM2 and NtLOM3 exhibited an expression level approximately ⅓ of that of the null line. Each of these lines was selected as a homo line in which NtLOM1 through NtLOM3 have suppressed expression.

(d) T2 Recombinant

Figure 3:
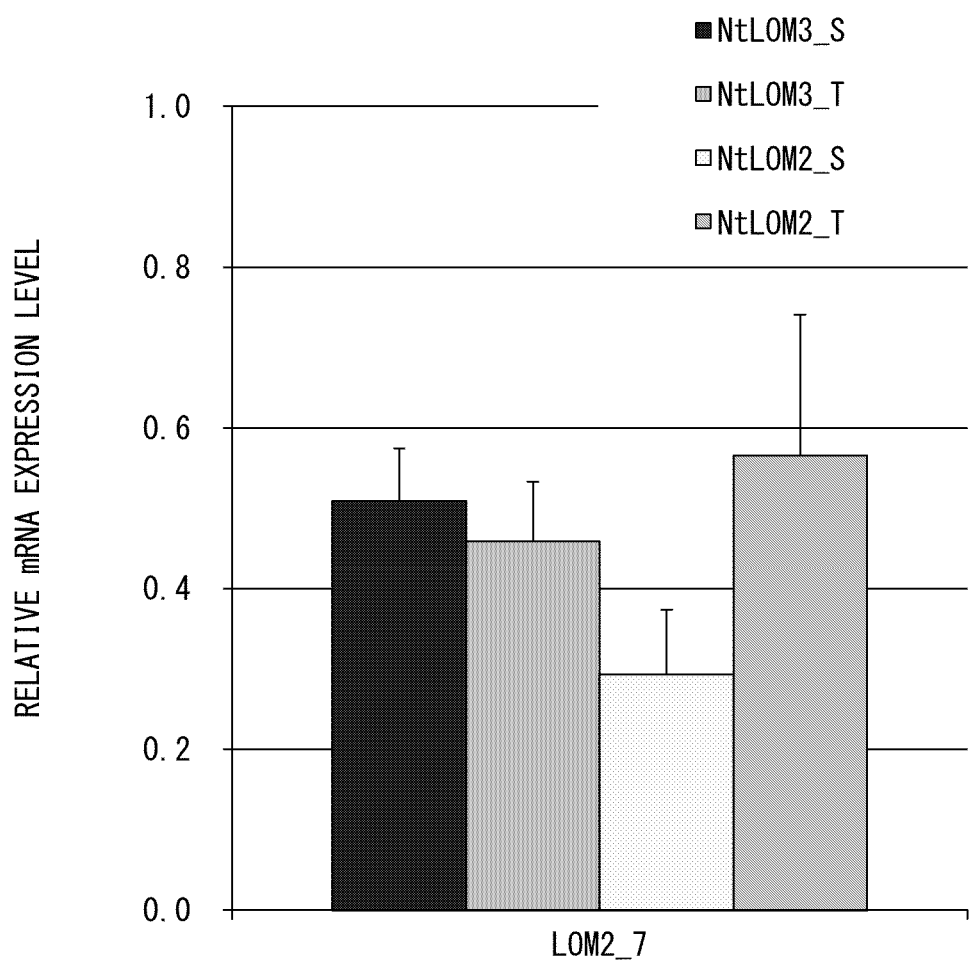
FIG. 3 is a view showing the results of determining mRNA expression levels of NtLOM2 and NtLOM3 in a tobacco plant (T2 individual).
Figure 4:
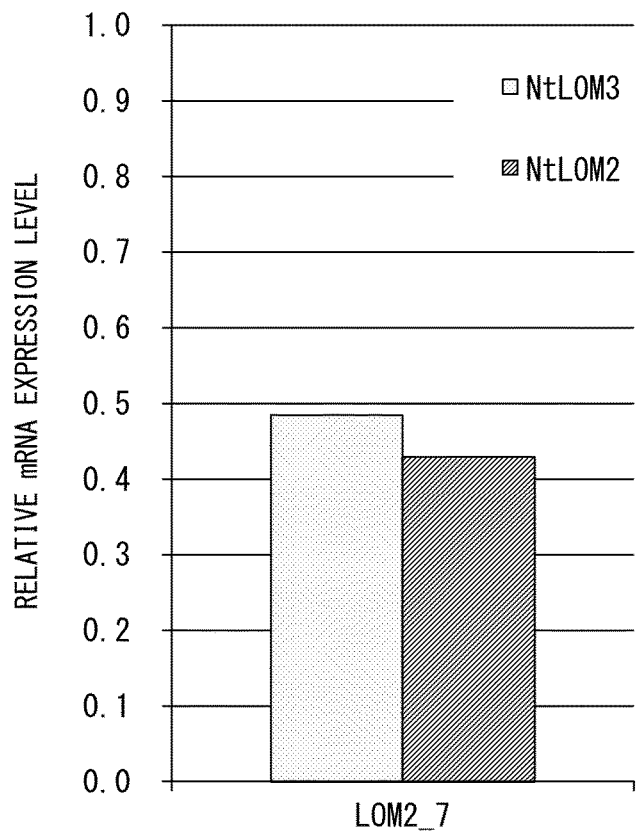
FIG. 4 is a view showing the results of determining mRNA expression levels of NtLOM2 and NtLOM3 in a tobacco plant (T2 individual).

T1 individuals (null and homo) related to NtLOM2 and NtLOM3 were selfed as in the case where T1 seeds were collected. This allowed T2 seeds to be collected. The T2 seeds were grown as described in the item (c), and the expression levels of NtLOM2 and NtLOM3 were determined. FIGS. 3 and 4 show the results. In FIGS. 3 and 4, the expression levels in null lines were set to 1 as in the case of FIGS. 1 and 2. FIG. 3 is a view showing the results of determining the expression level of each gene in S genome and in T genome. FIG. 4 corresponds to the results of putting the results of each gene of FIG. 3 together. As shown in FIG. 3, there was a difference in expression level between the S genome and the T genome. However, as shown in FIG. 4, the total level exhibited not more than ½ of the expression level in null lines. The seeds of the T2 individuals (recombinants in which two genes were suppressed) were subjected to axillary bud evaluation examination in Examples.

(2-1. Preparation of Mutants)

With use of CRISPR/Cas9 system, mutants, in which mutations were introduced into NtLOM1 through NtLOM3, were prepared.

(a) Preparation for Transformation

As a vector for transforming *Agrobacterium*, a binary vector pRI-201-AN (Takara-Bio Inc.) was used. Between NdeI-SalI of pRI-201-AN, pcoCas9 (Reference 1) which had been subjected to codon optimization for plants was introduced. Between KpnI-BamHI, a sgRNA expression cassette was introduced. As a promoter for guide sequence $GN_{20}GG$, AtU6-1 (Reference 2) was used. As a scaffold-polyT sequence, the sequence reported in Reference 2 was used. Specifically, the sgRNA expression cassette was designed so that the guide sequence excluding PAM sequence (NGG) at 3' end is inserted between the promoter and the scaffold-polyT sequence. Life Technologies Corporation was entrusted with synthesis, through GeneArt (registered trademark) Strings (trademark) DNA Fragments, of sgRNA expression cassette in which KpnI site and BamHI site are added to 5' end and 3' end, respectively. Cas9, in which NdeI site and SalI site are added to 5' end and 3' end, respectively, was obtained through entrusting Takara-Bio Inc. with synthesis of the Cas9.

[Chem. 1]
(SEQ ID NOs: 63 through 65)
NtLOM2_G2
aattggtaccAGAAATCTCAAAATTCCGGCAGAACAATT

TTGAATCTCGATCCGTAGAAACGAGACGGTCATTGTTT

TAGTTCCACCACGATTATATTTGAAATTTACGTGAGTGT

GAGTGAGACTTGCATAAGAAAATAAAATCTTTAGTTGG

GAAAAAATTCAATAATATAAATGGGCTTGAGAAGGAAGC

GAGGGATAGGCCTTTTTCTAAAATAGGCCCATTTAAGC

TATTAACAATCTTCAAAAGTACCACAGCGCTTAGGTAAA

GAAAGCAGCTGAGTTTATATATGGTTAGAGACGAAGTA

GTGATTgagctggaaaaattgacggcGTTTTAGAGCTAG

AAATAGCAAGTTAAAATAAGGCTAGTCCGTTATCAACT

TGAAAAAGTGGCACCGAGTCGGTGCTTTTTTTggatcca att

NtLOM3_G2
aattggtaccAGAAATCTCAAAATTCCGGCAGAACAATT

TTGAATCTCGATCCGTAGAAACGAGACGGTCATTGTTT

TAGTTCCACCACGATTATATTTGAAATTTACGTGAGTGT

GAGTGAGACTTGCATAAGAAAATAAAATCTTTAGTTGG

GAAAAAATTCAATAATATAAATGGGCTTGAGAAGGAAGC

GAGGGATAGGCCTTTTTCTAAAATAGGCCCATTTAAGC

TATTAACAATCTTCAAAAGTACCACAGCGCTTAGGTAAA

GAAAGCAGCTGAGTTTATATATGGTTAGAGACGAAGTA

GTGATTggttttgaggtctcagctgcGTTTTAGAGCTAG

AAATAGCAAGTTAAAATAAGGCTAGTCCGTTATCAACT

TGAAAAAGTGGCACCGAGTCGGTGCTTTTTTTggatcca att

NtLOM2-3_G1
aattggtaccAGAAATCTCAAAATTCCGGCAGAACAATT

TTGAATCTCGATCCGTAGAAACGAGACGGTCATTGTTT

TAGTTCCACCACGATTATATTTGAAATTTACGTGAGTGT

GAGTGAGACTTGCATAAGAAAATAAAATCTTTAGTTGG

GAAAAAATTCAATAATATAAATGGGCTTGAGAAGGAAGC

GAGGGATAGGCCTTTTTCTAAAATAGGCCCATTTAAGC

TATTAACAATCTTCAAAAGTACCACAGCGCTTAGGTAAA

GAAAGCAGCTGAGTTTATATATGGTTAGAGACGAAGTA

GTGATTgcctctgaattattactggcGTTTTAGAGCTAG

AAATAGCAAGTTAAAATAAGGCTAGTCCGTTATCAACT

TGAAAAAGTGGCACCGAGTCGGTGCTTTTTTTggatcca att

The underlined portion indicates the guide sequence. The portion upstream to the underlined portion indicates the AtU6-1 promoter sequence. The portion downstream to the underlined portion indicates the scaffold-polyT sequence. The lower case letters at the terminus indicate restriction enzyme sequences of KpnI and BamHI.

[Chem. 2]
(SEQ ID NO: 66)
Cas9 sequence
catATGGATTACAAGGATGATGATGATAAGGATTACAAGGATGATGATGATAAGATGGCTCCAAAGAAGAAGAGAAA
GGTTGGAATCCACGGAGTTCCAGCTGCTGATAAGAAGTACTCTATCGGACTTGACATCGGAACCAACTCTGTTGGAT
GGGCTGTTATCACCGATGAGTACAAGGTTCCATCTAAGAAGTTCAAGGTTCTTGGAAACACCGATAGACACTCTATC
AAGAAGAACCTTATCGGTGCTCTTCTTTTCGATTCTGGAGAGACCGCTGAGGCTACCAGATTGAAGAGAACCGCTAG
AAGAAGATACACCAGAAGAAAGAACAGAATCTGCTACCTTCAGGAAATCTTCTCTAACGAGATGGCTAAGGTTGATG
ATTCTTTCTTCCACAGACTTGAGGAGTCTTTCCTTGTTGAGGAGGATAAGAAGCACGAGAGACACCCAATCTTCGGA
AACATCGTTGATGAGGTTGCTTACCACGAGAAGTACCCAACCATCTACCACCTTAGAAAGAAGTTGGTTGATTCTAC
CGATAAGGCTGATCTTAGACTTATCTACCTTGCTCTTGCTCACATGATCAAGTTCAGAGGACACTTCCTTATCGAGG
GAGACCTTAACCCAGATAACTCTGATGTTGATAAGTTGTTCATCCAGCTTGTTCAGACCTACAACCAGCTTTTCGAG
GAGAACCCAATCAACGCTTCTGGAGTTGATGCTAAGGCTATCCTTTCTGCTAGACTTTCTAAGTCTCGTAGACTTGA
GAACCTTATCGCTCAGCTTCCAGGAGAGAAGAAGAACGGACTTTTCGGAAACCTTATCGCTCTTTCTCTTGGACTTA
CCCCAAACTTCAAGTCTAACTTCGATCTTGCTGAGGATGCTAAGTTGCAGCTTTCTAAGGATACCTACGATGATGAT
CTTGATAACCTTCTTGCTCAGATCGGAGATCAGTACGCTGATCTTTTCCTTGCTGCTAAGAACCTTTCTGATGCTAT
CCTTCTTTCTGACATCCTTAGAGTTAACACCGAGATCACCAAGGCTCCACTTTCTGCTTCTATGATCAAGAGATACG
ATGAGCACCACCAGGATCTTACCCTTTTGAAGGCTCTTGTTAGACAGCAGCTTCCAGAGAAGTACAAGGAAATCTTC
TTCGATCAGTCTAAGAACGGATACGCTGGATACATCGATGGAGGAGCTTCTCAGGAGGAGTTCTACAAGTTCATCAA
GCCAATCCTTGAAGATGGATGGAACCGAGGAGCTTCTTGTTAAGTTGAACAGAGAGGATCTTCTTAGAAAGCAGA
GAACTTTCGATAACGGATCTATCCCACACCAGATCCACCTTGGAGAGCTTCACGCTATCCTTCGTAGACAGGAGGAT
TTCTACCCATTCTTGAAGGATAACAGAGAGAAGATCGAGAAGATCCTTACCTTCAGAATCCCATACTACGTTGGACC
ACTTGCTAGAGGAAACTCTCGTTTCGCTTGGATGACCAGAAAGTCTGAGGAGACCATCACCCCTTGGAACTTCGAGG
AGGTAAGTTTCTGCTTCTACCTTTGATATATATATAATAATTATCATTAATTAGTAGTAATATAATATTTCAAATAT
TTTTTTCAAAATAAAAGAATGTAGTATATAGCAATTGCTTTTCTGTAGTTTATAAGTGTGTATATTTTAATTTATAA
CTTTTCTAATATATGACCAAAATTTGTTGATGTGCAGGTTGTTGATAAGGGAGCTTCTGCTCAGTCTTTCATCGAGA
GAATGACCAACTTCGATAAGAACCTTCCAAACGAGAAGGTTCTTCCAAAGCACTCTCTTCTTTACGAGTACTTCACC
GTTTACAACGAGCTTACCAAGGTTAAGTACGTTACCGAGGGAATGAGAAAGCCAGCTTTCCTTTCTGGAGAGCAGAA
GAAGGCTATCGTTGATCTTCTTTTCAAGACCAACAGAAAGGTTACCGTTAAGCAGTTGAAGGAGGATTACTTCAAGA
AGATCGAGTGCTTCGATTCTGTTGAAATCTCTGGAGTTGAGGATAGATTCAACGCTTCTCTTGGAACCTACCACGAT
CTTTTGAAGATCATCAAGGATAAGGATTTCCTTGATAACGAGGAGAACGAGGACATCCTTGAGGACATCGTTCTTAC
CCTTACCCTTTTCGAGGATAGAGAGATGATCGAGGAGAGACTCAAGACCTACGCTCACCTTTTCGATGATAAGGTTA
TGAAGCAGTTGAAGAGAAGAAGATACACCGGATGGGGTAGACTTTCTCGTAAGTTGATCAACGGAATCAGAGATAAG
CAGTCTGGAAAGACCATCCTTGATTTCTTGAAGTCTGATGGATTCGCTAACAGAAACTTCATGCAGCTTATCCACGA
TGATTCTCTTACCTTCAAGGAGGACATCCAGAAGGCTCAGGTTTCTGGACAGGGAGATTCTCTTCACGAGCACATCG
CTAACCTTGCTGGATCTCCAGCTATCAAGAAGGGAATCCTTCAGACCGTTAAGGTTGTTGATGAGCTTGTTAAGGTT
The sequence continues to the next page.

[Chem. 3]
Continuation of Cas9 sequence
ATGGGTAGACACAAGCCAGAGAACATCGTTATCGAGATGGCTAGAGAGAACCAGACCACCCAGAAGGGACAGAAGAA
CTCTCGTGAGAGAATGAAGAGAATCGAGGAGGGAATCAAGGAGCTTGGATCTCAAATCTTGAAGGAGCACCCAGTTG -continued

```
AGAACACCCAGCTTCAGAACGAGAAGTTGTACCTTTACTACCTTCAGAACGGAAGAGATATGTACGTTGATCAGGAG

CTTGACATCAACAGACTTTCTGATTACGATGTTGATCACATCGTTCCACAGTCTTTCTTGAAGGATGATTCTATCGA

TAACAAGGTTCTTACCCGTTCTGATAAGAACAGAGGAAAGTCTGATAACGTTCCATCTGAGGAGGTTGTTAAGAAGA

TGAAGAACTACTGGAGACAGCTTCTTAACGCTAAGTTGATCACCCAGAGAAAGTTCGATAACCTTACCAAGGCTGAG

AGAGGAGGACTTTCTGAGCTTGATAAGGCTGGATTCATCAAGAGACAGCTTGTTGAGACCAGACAGATCACCAAGCA

CGTTGCTCAGATCCTTGATTCTCGTATGAACACCAAGTACGATGAGAACGATAAGTTGATCAGAGAGGTTAAGGTTA

TCACCTTGAAGTCTAAGTTGGTTTCTGATTTCAGAAAGGATTTCCAGTTCTACAAGGTTAGAGAGATCAACAACTAC

CACCACGCTCACGATGCTTACCTTAACGCTGTTGTTGGAACCGCTCTTATCAAGAAGTACCCAAAGTTGGAGTCTGA

GTTCGTTTACGGAGATTACAAGGTTTACGATGTTAGAAAGATGATCGCTAAGTCTGAGCAGGAGATCGGAAAGGCTA

CCGCTAAGTACTTCTTCTACTCTAACATCATGAACTTCTTCAAGACCGAGATCACCCTTGCTAACGGAGAGATCAGA

AAGAGACCACTTATCGAGACCAACGGAGAGACCGGAGAGATCGTTTGGGATAAGGGAAGAGATTTCGCTACCGTTAG

AAAGGTTCTTTCTATGCCACAGGTTAACATCGTTAAGAAAACCGAGGTTCAGACCGGAGGATTCTCTAAGGAGTCTA

TCCTTCCAAAGAGAAACTCTGATAAGTTGATCGCTAGAAAGAAGGATTGGGACCCAAAGAAGTACGGAGGATTCGAT

TCTCCAACCGTTGCTTACTCTGTTCTTGTTGTTGCTAAGGTTGAGAAGGGAAAGTCTAAGAAGTTGAAGTCTGTTAA

GGAGCTTCTTGGAATCACCATCATGGAGCGTTCTTCTTTCGAGAAGAACCCAATCGATTTCCTTGAGGCTAAGGGAT

ACAAGGAGGTTAAGAAGGATCTTATCATCAAGTTGCCAAAGTACTCTCTTTTCGAGCTTGAGAACGGAAGAAAGAGA

ATGCTTGCTTCTGCTGGAGAGCTTVAGAAGGGAAACGAGCTTGCTCTTCCATCTAAGTACGTTAACTTCCTTTACCT

TGCTTCTCACTACGPLAAGTTGAAGGGATCTCCAGAGGATAACGAGCAGAAGCACCTTTTCGTTGAGCAGCACAAGC

ACTACCTTGATGAGATCATCGAGCAAATCTCTGAGTTCTCTAAGAGAGTTATCCTTGCTGATGCTAACCTTGATAAG

GTTCTTTCTGCTTACAACAAGCACAGAGATAAGCCAATCAGAGAGCAGGCTGAGAACATCATCCACCTTTTCACCCT

TACCAACCTTGGTGCTCCAGCTGCTTTCAAGTACTTCGATACCACCATCGATAGAAAAAGATACACCTCTACCAAGG

AGGTTCTTGATGCTACCCTTATCCACCAGTCTATCACCGGACTTTACGAGACCAGAATCGATCTTTCTCAGCTTGGA

GGAGATAAGAGACCAGCTGCTACCAAGAAGGCTGGACAGGCTAAGAAGAAGAAGTGAgtcgac
```

In the above Cas9 sequence over 2 pages, the underlined portions indicate the NdeI sequence and the SalI sequence.

With use of pRI201-AN in which the Cas9 and the sgRNA expression cassette were introduced, *Agrobacterium* LBA4404 was transformed by electroporation. The *Agrobacterium* was grown on an AB plate containing kanamycin at 25 μg/ml. Then, *Agrobacterium* of a single colony was isolated.

(b) Transformation of Tobacco and Cultivation of Transformant

Segments of a cotyledon collected from tobacco (variety: SR-1) 10 days after sowing were co-cultured for 3 days with the transformed *Agrobacterium* obtained as described above. Then, the *Agrobacterium* was then removed from the segments of the cotyledon by washing the segments with use of distilled water containing an antibacterial agent (cefotaxime). Then, the *Agrobacterium* was completely removed by culturing, for 4 days, the washed segments of the cotyledon in Linsmaier and Skoog medium containing an antibacterial agent. Then, the segments of the cotyledon were transferred to and cultured in Linsmaier and Skoog medium containing antibiotics (kanamycin), so that redifferentiated individuals (shoots) having kanamycin resistance were obtained. The shoots were transferred to Linsmaier and Skoog rooting medium and then rooted. Rooted individuals were selected, and then transplanted into and grown in a 9-cm pot containing soil for transplantation (Compost: 40 L, wild soil: 30 L, Akadama soil (small): 10 L, Akadama soil (medium): 10 L, vermiculite: 10 L, fertilizer (S625): 1000 g).

(c) Confirmation of Presence/Absence of Mutation and Mutant Sequence

PCR was performed by use of Tks Gflex (trademark) DNA polymerase (Takara-Bio Inc.) with genomic DNA as a template, which genomic DNA was extracted from a leaf of a transformant of tobacco that had been grown. The reaction conditions and the combinations of primers of the PCR are as follows.

(Reaction Conditions)
30 seconds to 60 seconds at 94° C.
30 cycles to 40 cycles while each cycle includes 10 seconds at
98° C., 15 seconds at 55° C., and 30 seconds to 60 seconds* at 68° C.
60 seconds at 68° C.
(Primers)
Examination of mutant sequence in mutant in which NtLOM2_G2 was used NtLOM2
S genome gene
NtLOM2_S_Fw: (SEQ ID NO: 67)
CCTAGCAGGAGCAAAAGGG -continued

```
NtLOM2_S_Rv:
                                    (SEQ ID NO: 68)
TCTATTATTTGAGTCAATGACAACAG

T genome gene
NtLOM2_T_Fw:
                                    (SEQ ID NO: 69)
CAACCTAGCAGTAGCAAAAGGA NtLOM2_T_Rv:
                                    (SEQ ID NO: 70)
TCTGTTGTTTGAGTCTATGACAGCAT
```

Examination of mutant sequence in mutant in which NtLOM3_G2 was used

```
NtLOM3
S genome gene
NtLOM3_S_Fw:
                                    (SEQ ID NO: 71)
ACCTCAATGTATTCCTAAATCCTAACACCTAAAG NtLOM3_S_Rv:
                                    (SEQ ID NO: 72)
GGGCTGTTCTTGAGTTACATCATAAG T genome gene
NtLOM3_T_Fw:
                                    (SEQ ID NO: 73)
CCTCAAAGTTTTCCTAAATTCTAACGCCTAAC NtLOM3_T_Rv:
                                    (SEQ ID NO: 74)
GGGCTGTTCTTGACTTATATCATATG
```

Examination of mutant sequence in mutant in which NtLOM2-3_G1 was used

```
NtLOM2
S genome gene
NtLOM2-3_2_S_Fw2:
                                    (SEQ ID NO: 75)
GTCCACAAATAATGACAAACCAACA NtLOM2-3_2_S_Rv2:
                                    (SEQ ID NO: 76)
GAAAGCTGCTTCATACGTGAAGAA T genome gene
NtLOM2-3_2_T_Fw2:
                                    (SEQ ID NO: 77)
GTCCACAAATAGTGGCAAACCAAAC NtLOM2-3_2_T_Rv2:
                                    (SEQ ID NO: 78)
CTCCTCAGCACCTCCAAGAC NtLOM3
S genome gene
NtLOM2-3_3_S_Fw2:
                                    (SEQ ID NO: 79)
TATGTTAGGCTCATTATCTTATGATGTAAC NtLOM2-3_3_S_Rv3:
                                    (SEQ ID NO: 80)
GGCAAAAGGAAAGGCAATAGC T genome gene
NtLOM2-3_3_T_Fw2:
                                    (SEQ ID NO: 81)
CATGTTAGGCTCATTATCATATGATATAAG NtLOM2-3_3_T_Rv3:
                                    (SEQ ID NO: 82)
GGCAAAAGGAAAGGTAACTGC
```

After the PCR reactions, denaturation and annealing were performed under the following conditions. Denaturation: 5 minutes at 95° C., annealing: 1 second at 85° C./1 second at 85° C., 1 second at 60° C., constant at 30° C. The Ramp Rate at 85° C. to 60° C. was 5% (drop rate of 0.1° C./second), and the Ramp Rate at 60° C. to 30° C. was 10% (drop rate of 0.1° C./second). The PCR products of 5 µl after the denaturation and annealing were treated in a reaction system of 10 µl with use of T7 endonuclease I (New England Biolabs) of 1 U, and then were separated by electrophoresis. Then, it was checked whether or not the PCR products were cleaved by the enzyme. Separately, the PCR products were directly sequenced or cloned with use of Zero Blunt TOPO PCR Cloning Kit, and the clone was sequenced.

(d) Selection of Recombinant

Individuals of T0 generation having mutations (deletion or insertion of 1 or more bases) in NtLOM2 of S genome and T genome and in NtLOM3 of S genome and T genome were each selfed and collected, so that T1 lines were obtained. The presence/absence of the mutations of the gene in the individuals of the T1 lines was confirmed as in the item (c) above. Based on the results of the confirmation, individuals of the T1 lines having mutations in the genes of both S genome and T genome were selfed. This produced individuals of T2 line (one-gene mutant) which had mutations in NtLOM2 or NtLOM3 of both S genome and T genome. The one-gene mutants were subjected to examination discussed in Comparative Examples (described later).

In a case where NtLOM2-3_G1 was used as an sgRNA expression cassette, the individuals of T0 generation, which had mutations in both NtLOM2 and NtLOM3 of S genome and T genome, were selfed and collected, so that the T1 line was obtained. The presence/absence of the mutations in the individuals of the T1 line was confirmed as in (c) above. Based on the results of the confirmation, individuals of the T1 lines, which had mutations in both NtLOM2 and NtLOM3 of S genome and T genome, were selfed. This produced individuals of T2 line (two-gene mutant) which had mutations in both NtLOM2 and NtLOM3 of S genome and T genome.

The mutations in the one-gene mutant and the two-gene mutant will be described in detail below.

(One-Gene Mutant (NtLOM3): 3 Lines)

(1) 6G2-29A-31

S genome: While WT consists of 626 amino acids, a polypeptide is produced such that (i) 20 amino acids (72nd through 91st amino acids) are deleted, (ii) 92nd alanine is substituted with asparagine, and (iii) 93rd through 626th are identical to those of WT.

T genome: While WT consists of 624 amino acids, a polypeptides is produced such that unrelated 3 amino acids (QVL) are added in addition to up to 90 amino acids identical to those of WT.

(2) 6G2-29A-55

S genome: While WT consists of 626 amino acids, a polypeptide is produced such that (i) 20 amino acids (72nd through 91st amino acids) are deleted, (ii) 92nd alanine is substituted with asparagine, and (iii) 93rd through 626th are identical to those of WT.

T genome: While WT consists of 624 amino acids, a polypeptides is produced such that unrelated 8 amino acids (CRFFSSYR (SEQ ID NO: 83)) are added in addition to up to 90 amino acids identical to those of WT.

(3) 6G2-65-1

S genome: While WT consists of 626 amino acids, a polypeptides is produced such that unrelated 8 amino acids (CRFFSSYR (SEQ ID NO: 83)) are added in addition to up to 91 amino acids identical to those of WT.

T genome: While WT consists of 624 amino acids, a polypeptide is produced such that 90th alanine is deleted so as to constitute 623 amino acids.

(One-Gene Mutant (NtLOM2): 1 Line)
22G2-58-26
S genome: While WT consists of 714 amino acids, a polypeptide is produced such that unrelated 58 amino acids (MAGKRSWLLSCSHFHLSWSQKNLILDLGIWIIC-CRNLPAPTRPF SGGSPAIWRTHQLA (SEQ ID NO: 84)) are added in addition to up to 83 amino acids identical to those of WT.
T genome: While WT consists of 714 amino acids, a polypeptides is produced such that unrelated 18 amino acids (NCVNRLEIMSIVLITYNL (SEQ ID NO: 85)) are added in addition to up to 85 amino acids identical to those of WT.

(Two-Gene Mutant (NtLOM2 and NtLOM3): 3 Lines)
(1) G1-179-2
Mutation in NtLOM2
S genome: While WT consists of 714 amino acids, a polypeptide is produced such that 361st leucine is deleted so as to constitute 713 amino acids.
T genome: While WT consists of 714 amino acids, a polypeptide is produced such that unrelated 9 amino acids (RPDISQTRK (SEQ ID NO: 86)) are added in addition to up to 362 amino acids identical to those of WT.
Mutation in NtLOM3
S genome: While WT consists of 626 amino acids, a polypeptide is produced such that unrelated 57 amino acids (GRTILKRANDIGAAQSTALSPWQTLQEVCFLLQRG-SAIAFPFALY IHIFSTKNSHAI (SEQ ID NO: 87)) are added in addition to up to 275 amino acids identical to those of WT.
T genome: While WT consists of 624 amino acids, a polypeptide is produced such that unrelated 9 amino acids (RPDNSQTRK (SEQ ID NO: 88)) are added in addition to up to 272 amino acids identical to those of WT.

(2) G1-179-17
Mutation in NtLOM2
S genome: While WT consists of 714 amino acids, the following polypeptides are produced: (i) a polypeptide consisting of 713 amino acids in which 361st leucine is deleted; and (ii) a polypeptide in which unrelated 57 amino acids (GRTFLKRANDIGAAQSTALSH-WQTLQEGCFLLQRGSAVTFPFAL YIHIFSTKNSHPI (SEQ ID NO: 89)) are added in addition to up to 362nd amino acid identical to those of WT.
T genome: While WT consists of 714 amino acids, a polypeptide is produced such that unrelated 9 amino acids (RPDISQTRK (SEQ ID NO: 86)) are added in addition to up to 362 amino acids identical to those of WT.
Mutation in NtLOM3
S genome: While WT consists of 626 amino acids, a polypeptide is produced such that unrelated 57 amino acids (GRTILKRANDIGAAQSTALSPWQTLQEVCFLLQRG-SAIAFPFALY IHIFSTKNSHAI (SEQ ID NO: 87)) are added in addition to up to 275 amino acids identical to those of WT.
T genome: While WT consists of 624 amino acids, a polypeptides is produced such that unrelated 9 amino acids (RPDNSQTRK (SEQ ID NO: 88)) are added in addition to up to 272 amino acids identical to those of WT.

(3) G1-179-26
Mutation in NtLOM2
S genome: While WT consists of 714 amino acids, a polypeptide is produced such that unrelated 57 amino acids (GRTFLKRANDIGAAQSTALSH-WQTLQEGCFLLQRGSAVTFPFAL YIHIFSTKNSHPI (SEQ ID NO: 89)) are added in addition to up to 362nd amino acid identical to those of WT.
T genome: While WT consists of 714 amino acids, a polypeptides is produced such that unrelated 9 amino acids (RPDISQTRK (SEQ ID NO: 86)) are added in addition to up to 362 amino acids identical to those of WT.
Mutation in NtLOM3
S genome: While WT consists of 626 amino acids, a polypeptide is produced such that unrelated 57 amino acids (GRTILKRANDIGAAQSTALSPWQTLQEVCFLLQRG-SAIAFPFALY IHIFSTKNSHAI (SEQ ID NO: 87)) are added in addition to up to 275 amino acids identical to those of WT.
T genome: While WT consists of 624 amino acids, a polypeptide is produced such that unrelated 9 amino acids (RPDNSQTRK (SEQ ID NO: 88)) are added in addition to up to 272 amino acids identical to those of WT.

[3. Evaluation of Effect of Candidate Genes on Development of Axillary Buds]

The development of axillary buds of the mutants and the recombinants were evaluated as described below.

The seeds of the mutants and recombinants and wild-types thereof were sowed and cultivated in a containment greenhouse or an artificial light growth cabinet, Koitotron (Koito Manufacturing Co., Ltd.). The conditions of the containment greenhouse were set so that the temperature was maintained at room temperature of 23° C. to 25° C., and the day length was that of a natural day. The conditions of Koitotron were set so that the day length was 12 hours, and the temperature was 25° C. (light period) and 18° C. (dark period). The individuals were cultivated in 15-cm pots which were filled with rich soil having a volume of 500 mL/pot. The composition of the rich soil was as follows. Compost: 40 L, wild soil: 30 L, Akadama soil (small): 10 L, Akadama soil (medium): 10 L, vermiculite: 10 L, fertilizer (S625): 1000 g.

Topping was performed when 12 to 13 true leaves were produced during a period starting at budding and ending before flowering. The target selected to be evaluated was an axillary bud which was produced in a fourth true leaf from the bottom of an aerial part or a higher leaf. Each week since the topping, the number of axillary buds with a stem having a length of approximately 5 mm or longer was recorded. The axillary buds thus recorded were picked by hand from the base thereof, and the fresh weight (FW) of the axillary buds thus picked was measured. Until the development of new axillary buds was no longer found, the number and fresh weight of axillary buds were measured over substantially 5 times.

Figure 5:
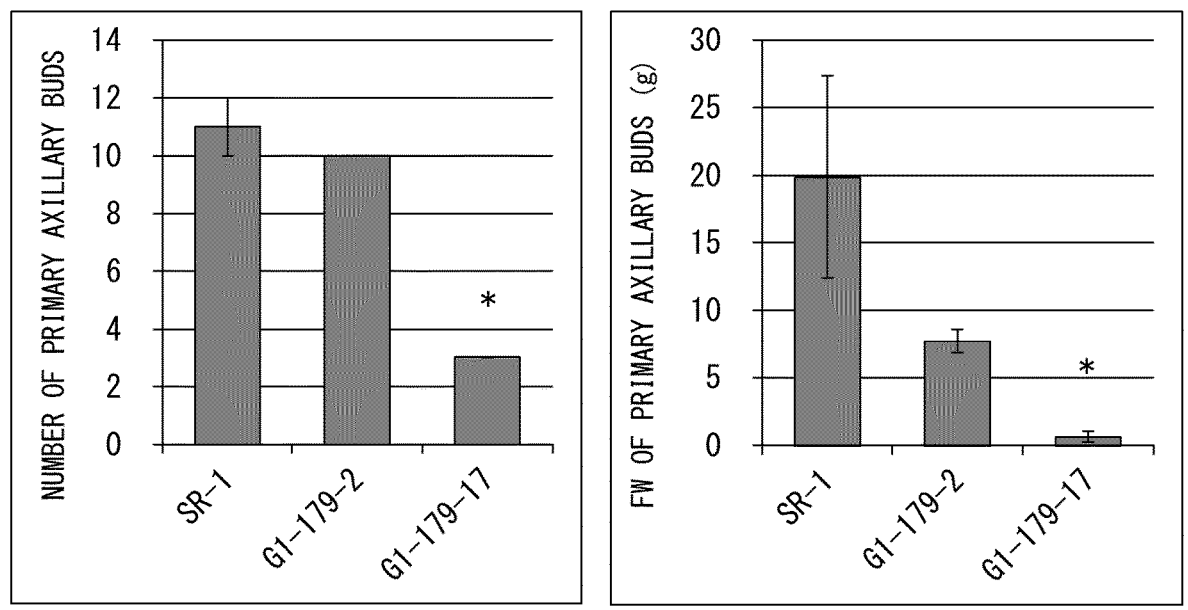
FIG. 5 is a view showing the results of evaluation of axillary bud formation in a tobacco plant in accordance with an example of the present invention.
Figure 6:
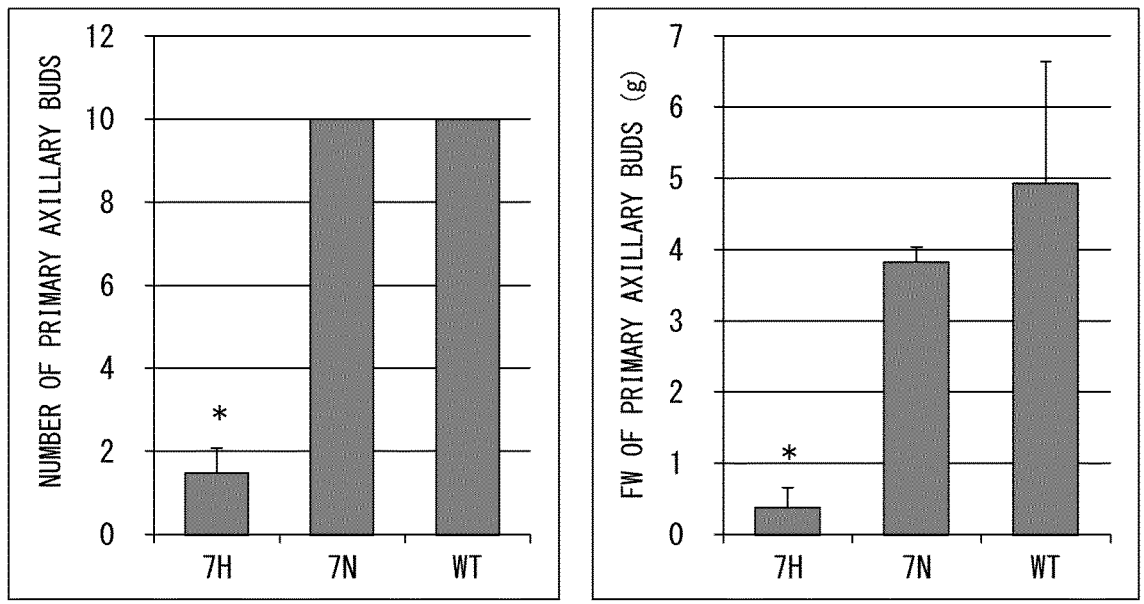
FIG. 6 is a view showing the results of evaluation of axillary bud formation in a tobacco plant in accordance with another example of the present invention.

FIGS. 5 and 6 show the results. FIG. 5 is a view showing the results of evaluation of axillary bud development in the two-gene mutants. FIG. 6 is a view showing the results of evaluation of axillary bud development in the recombinants in which two genes were suppressed.

As shown in FIG. 5, G1-179-2 of the two-gene mutants exhibited a remarkable decrease in fresh weight (FW) of primary axillary buds in comparison with WT. In addition, G1-179-17 of the two-gene mutants exhibited a statistically significant decrease in the number and fresh weight of primary axillary buds in comparison with the wild-type (WT). Although not particularly shown in FIG. 5, there was no remarkable difference observed in terms of growth between the two-gene mutants and WT. In addition, although not shown in FIG. 5, G1-179-26, which was obtained as with the two-gene mutant, exhibited no formation or development of primary axillary buds from leaf axil even if the shoot apex was cut before budding (i.e., flower buds were not formed).

Because FW increases along with the growth of primary axillary buds, a significant decrease in FW means that the growth of the primary axillary buds is significantly suppressed. Although primary axillary buds are formed, slow growth of the primary axillary buds causes the following: (i) it is unnecessary to remove the primary axillary buds; (ii) it is unnecessary to apply agrochemicals to the primary axillary buds, and (iii) the number of times of applying agrochemicals decreases. Therefore, the significant decrease in FW substantially reduces labor resulting from a process of suppressing axillary buds. Note that the two-gene mutants of the 2 individuals produced no secondary axillary buds.

As shown in FIG. 6, the recombinants in which two genes were suppressed (7H) exhibited statistically significant decreases in the number and FW of primary axillary buds in comparison with (i) individuals (7N) in which expression of neither NtLOM2 nor NtLOM3 was suppressed and (ii) WT. Although not particularly shown in FIG. 6, there was no remarkable difference observed in terms of growth between 7H, 7N, and WT the two-gene mutants and WT. However, the decrease in the number of flower buds in 7H was observed.

COMPARATIVE EXAMPLES

Figure 7:
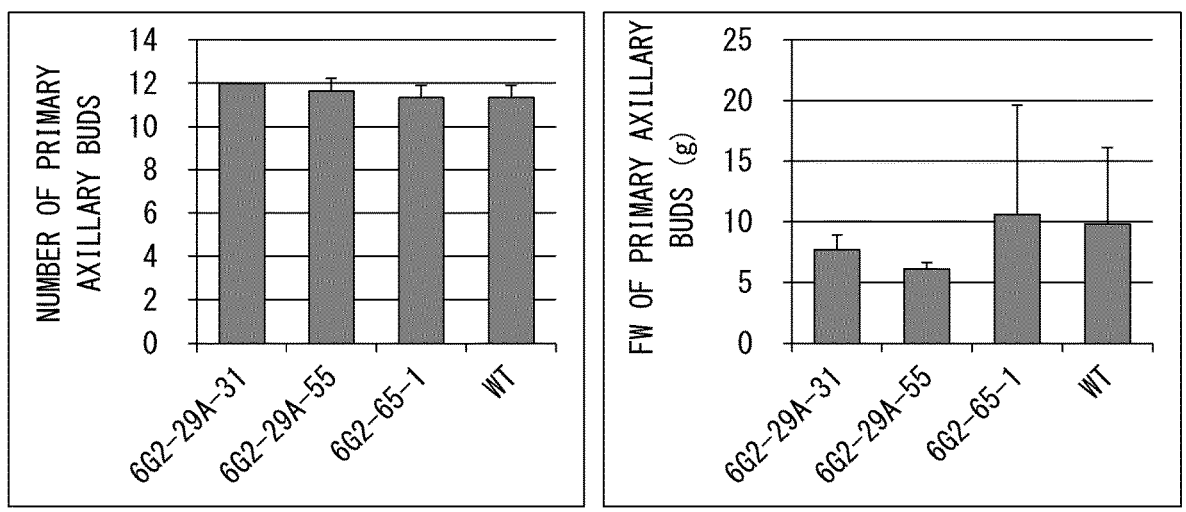
FIG. 7 is a view showing the results of evaluation of axillary bud formation in a tobacco plant in accordance with a comparative example.
Figure 8:
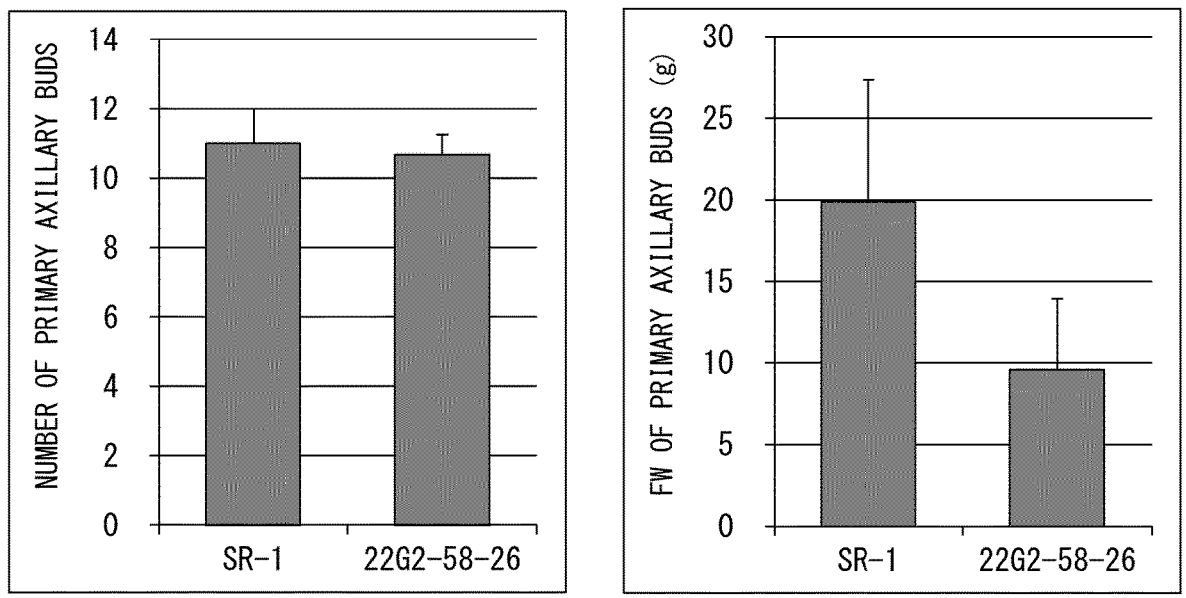
FIG. 8 is a view showing the results of evaluation of axillary bud formation in a tobacco plant in accordance with another comparative example.
Figure 9:
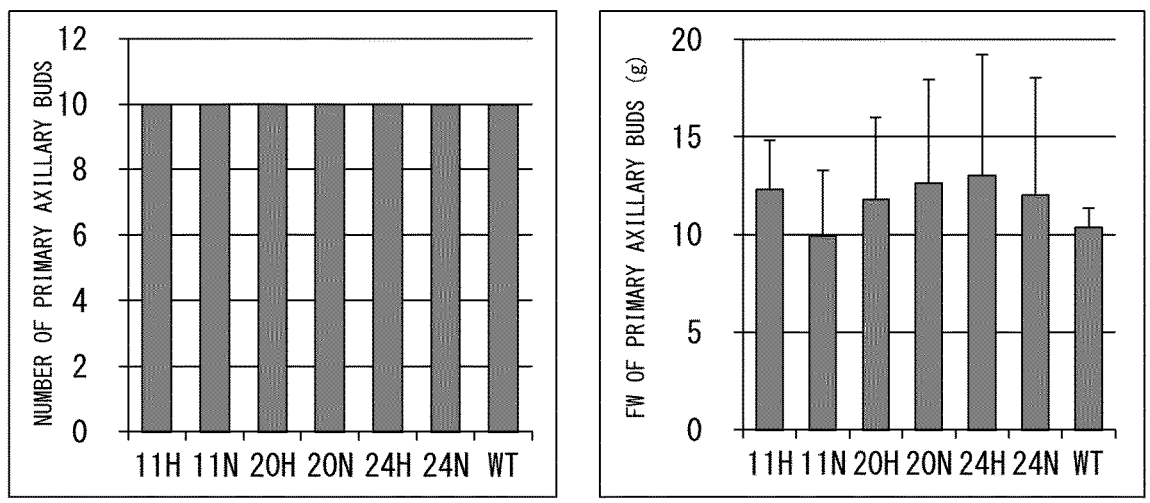
FIG. 9 is a view showing the results of evaluation of axillary bud formation in a tobacco plant in accordance with another comparative example.

As in the item 3., the development of axillary buds of the following was evaluated: two kinds of recombinants in which one gene had suppressed expression (3 individuals), and two kinds of mutants in which one gene had mutation (4 individuals). FIGS. 7 through 9 show the results. As shown in FIGS. 7 and 9, functional suppression of one gene (suppressed expression and mutation) did not suppress the development of primary axillary buds. As shown in FIG. 8, it appeared that one-gene mutant, in which the mutation was introduced into the NtLOM2 gene, exhibited a decrease in weight of primary axillary buds by approximately 50% on average (no significant difference from SR-1). For the purpose of confirming these results, recombinants in which one gene (NtLOM2) had suppressed expression, instead of mutants, were prepared as described above.

Figure 10:
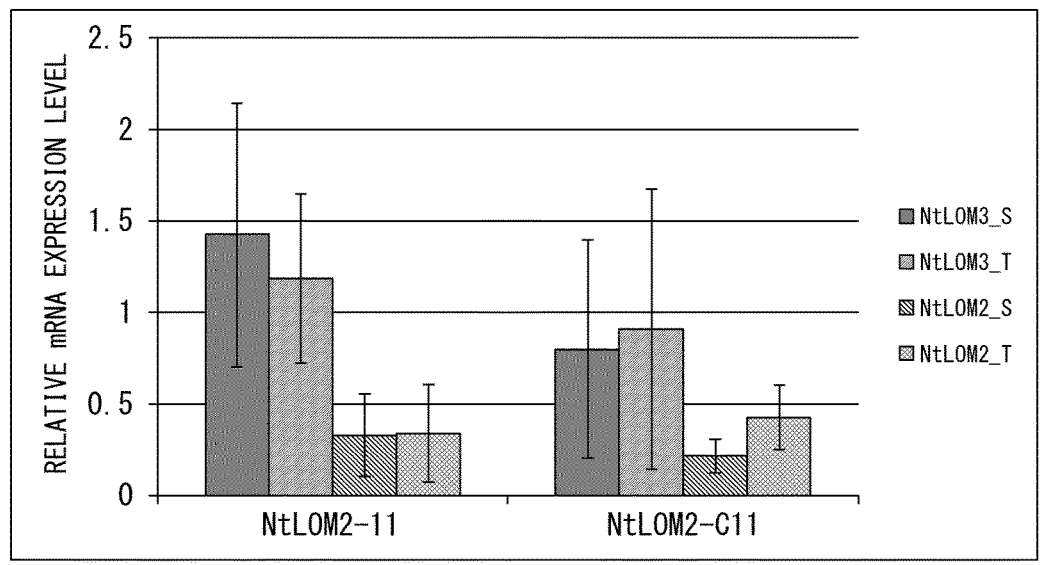
FIG. 10 is a view showing the results of evaluation of expression levels of NtLOM2 and NtLOM3 and axillary bud formation in a tobacco plant in accordance with another comparative example.
Figure 10:
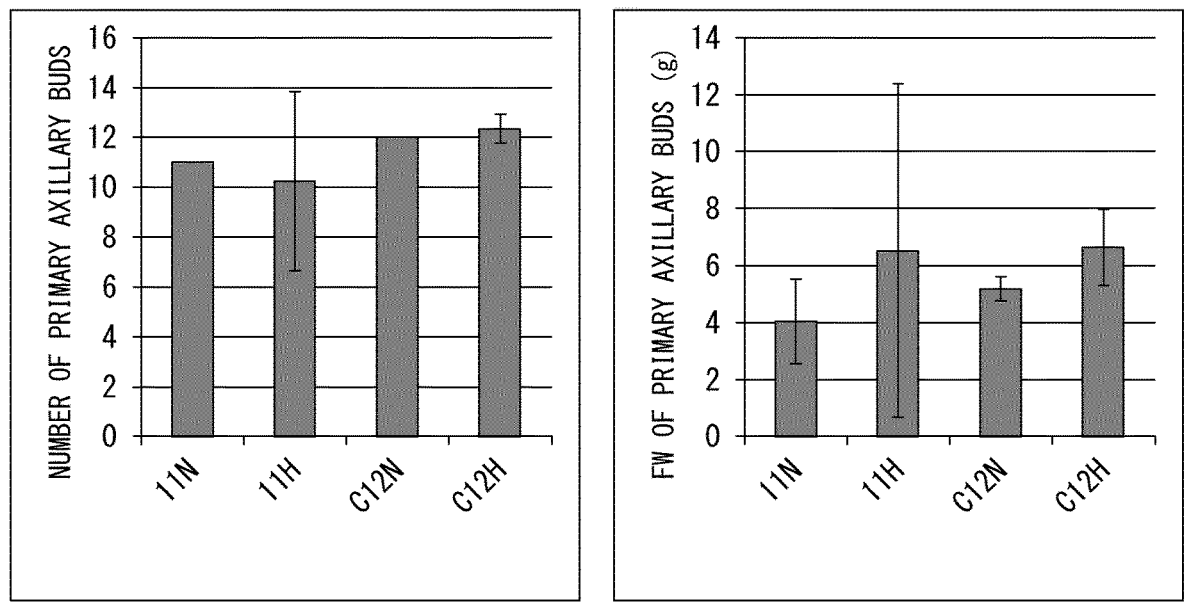

FIG. 10 shows the results of confirming mRNA expression levels and axillary bud development of NtLOM2 in the recombinants (2 individuals) in which one gene (NtLOM2) had suppressed expression. As shown in the upper row of FIG. 10, (i) the expression of the mRNA of NtLOM2 of the recombinants was specifically suppressed and (ii) the mRNA expression levels of NtLOM3 of the recombinants were not suppressed. As shown in the lower row of FIG. 10, in contrast to the results shown in FIG. 8, a homo line of each line exhibited an increase in weight of axillary buds in comparison with a null line. Therefore, it was found that functional suppression of one gene is insufficient to stably suppress the development of axillary buds, and that functional suppression of two genes is extremely preferable for suppressing the development of axillary buds.

Hence, it became evident that the development of primary axillary buds cannot be suppressed merely by manipulating only an orthologous gene of tobacco, even though it is suggested that the orthologous gene is involved in the formation of axillary buds in other plants.

REFERENCES

1. Li J F, Norville J E, Aach J, McCormack M, Zhang D, Bush J, Church G M, Sheen J. (2013) Multiplex and homologous recombination-mediated genome editing in *Arabidopsis* and *Nicotiana benthamiana* using guide RNA and Cas9. Nat Biotechnol. 31(8), 688-91.
2. Waibel F, Filipowicz W. (1990) U6 snRNA genes of *Arabidopsis* are transcribed by RNA polymerase III but contain the same two upstream promoter elements as RNA polymerase II-transcribed U-snRNA genes. Nucleic Acids Res. 25; 18(12), 3451-8.

INDUSTRIAL APPLICABILITY

With an embodiment of the present invention, it is possible to suppress the development of unnecessary axillary buds during cultivation of tobacco plant. This allows for a reduction in labor and cost during cultivation, and leads to an increase in quality of leaves to be harvested.

The invention claimed is:

1. A mutated tobacco plant comprising at least two mutations in the genome of said tobacco plant, wherein said at least two mutations cause functional suppression of each of at least two of the following nucleotide products (1) through (3):
   (1) at least one of: a gene comprising, as a coding region, a polynucleotide (a); and a gene comprising, as a coding region, a polynucleotide (c);
   (2) at least one of: a gene comprising, as a coding region, a polynucleotide (e); and a gene comprising, as a coding region, a polynucleotide (g); and
   (3) at least one of: a gene comprising, as a coding region, a polynucleotide (i); and a gene comprising, as a coding region, a polynucleotide (k),
   the functional suppression suppressing development of primary axillary buds,
   the polynucleotide (a) being a polynucleotide encoding a polypeptide having a sequence identity of 98% or higher with an amino acid sequence represented by SEQ ID NO: 1,
   the polynucleotide (c) being a polynucleotide encoding a polypeptide having a sequence identity of 98% or higher with an amino acid sequence represented by SEQ ID NO: 2,
   the polynucleotide (e) being a polynucleotide encoding a polypeptide having a sequence identity of 98% or higher with an amino acid sequence represented by SEQ ID NO: 3,
   the polynucleotide (g) being a polynucleotide encoding a polypeptide having a sequence identity of 98% or higher with an amino acid sequence represented by SEQ ID NO: 4,
   the polynucleotide (i) being a polynucleotide encoding a polypeptide having a sequence identity of 98% or higher with an amino acid sequence represented by SEQ ID NO: 5,
   the polynucleotide (k) being a polynucleotide encoding a polypeptide having a sequence identity of 98% or higher with an amino acid sequence represented by SEQ ID NO: 6, wherein
   the tobacco plant is *Nicotiana tabacum*;
   the mutation is introduced into each of at least two of the nucleotide products (1)— (3);
   the mutation that causes the functional suppression is selected from the group consisting of a frame-shift mutation or a nonsense mutation; and
   the functional suppression causes the number or weight of primary axillary buds to decrease to not more than ½ of that of a wild-type plant which is a wild type of a variety identical to that of said mutated tobacco plant that comprises at least two of said nucleotide products (1)— (3) and not having said at least two mutations.

2. The tobacco plant according to claim 1, wherein the functional suppression is a decrease, as compared with a wild-type plant, in abundance of polypeptides which are expression products of the at least two genes.

3. The tobacco plant according to claim 2, wherein the functional suppression is a decrease, as compared with a wild-type plant, in an amount of translation of the polypeptides which are expression products of the at least two genes.

4. The tobacco plant according to claim 2, wherein the functional suppression is a decrease, as compared with a wild-type plant, in an amount of transcription from the at least two genes to mRNA.

5. The tobacco plant according to claim 1, wherein the mutation is introduced into each of the at least two genes.

6. The tobacco plant according to claim 5, wherein the mutation is introduced by spontaneous mutation, mutagen treatment, gene recombination, genome editing, or gene knockout.

7. A method of producing a mutated tobacco plant, comprising the step of:
   (A) introducing, into the genome of a tobacco plant, at least two mutations causing functional suppression of each of at least two of the following nucleotide products (1) through (3):
   (1) at least one of: a gene comprising, as a coding region, a polynucleotide (a); and a gene comprising, as a coding region, a polynucleotide (c);
   (2) at least one of: a gene comprising, as a coding region, a polynucleotide (e); and a gene comprising, as a coding region, a polynucleotide (g); and
   (3) at least one of: a gene comprising, as a coding region, a polynucleotide (i); and a gene comprising, as a coding region, a polynucleotide (k),
   the functional suppression suppressing development of primary axillary buds,
   the polynucleotide (a) being a polynucleotide encoding a polypeptide having a sequence identity of 98% or higher with an amino acid sequence represented by SEQ ID NO: 1,
   the polynucleotide (c) being a polynucleotide encoding a polypeptide having a sequence identity of 98% or higher with an amino acid sequence represented by SEQ ID NO: 2,
   the polynucleotide (e) being a polynucleotide encoding a polypeptide having a sequence identity of 98% or higher with an amino acid sequence represented by SEQ ID NO: 3,
   the polynucleotide (g) being a polynucleotide encoding a polypeptide having a sequence identity of 98% or higher with an amino acid sequence represented by SEQ ID NO: 4,
   the polynucleotide (i) being a polynucleotide encoding a polypeptide having a sequence identity of 98% or higher with an amino acid sequence represented by SEQ ID NO: 5,
   the polynucleotide (k) being a polynucleotide encoding a polypeptide having a sequence identity of 98% or higher with an amino acid sequence represented by SEQ ID NO: 6, wherein
   the tobacco plant is *Nicotiana tabacum*;
   the mutation is introduced into each of at least two of the nucleotide products (1)— (3);
   the mutation that causes the functional suppression is selected from the group consisting of a frame-shift mutation or a nonsense mutation; and
   the functional suppression causes the number or weight of primary axillary buds to decrease to not more than ½ of that of a wild-type plant which is a wild type of a variety identical to that of said mutated tobacco plant that comprises at least two of said nucleotide products (1)— (3) and not having said at least two mutations.

8. The method according to claim 7, further comprising the step of:
   (B) selecting, from individuals produced by the step (A), an individual in which development of the primary axillary buds is suppressed.

9. The method according to claim 8, wherein in the step (B), an individual, in which the number or weight of the primary axillary buds is decreased in comparison with that of a wild-type plant, is selected.

10. The method according to claim 7, wherein the step (A) includes introducing the mutation into each of the at least two genes.

11. A method of determining a mutated tobacco plant in which development of primary axillary buds is suppressed, the method comprising the steps of:
  (A) obtaining a sample by collecting a part of a tobacco plant;
  (B) detecting, from the genome included in the sample, at least two mutations causing functional suppression of each of at least two of the following nucleotide products (1) through (3) on the genome:
    (1) at least one of: a gene comprising, as a coding region, a polynucleotide (a); and a gene comprising, as a coding region, a polynucleotide (c);
    (2) at least one of: a gene comprising, as a coding region, a polynucleotide (e); and a gene comprising, as a coding region, a polynucleotide (g); and
    (3) at least one of: a gene comprising, as a coding region, a polynucleotide (i); and a gene comprising, as a coding region, a polynucleotide (k); and
  (C) determining that a tobacco plant, in which the mutation has been detected, is a tobacco plant in which the development of the primary axillary buds is suppressed,
  the polynucleotide (a) being a polynucleotide encoding a polypeptide having a sequence identity of 98% or higher with an amino acid sequence represented by SEQ ID NO: 1,
  the polynucleotide (c) being a polynucleotide encoding a polypeptide having a sequence identity of 98% or higher with an amino acid sequence represented by SEQ ID NO: 2,
  the polynucleotide (e) being a polynucleotide encoding a polypeptide having a sequence identity of 98% or higher with an amino acid sequence represented by SEQ ID NO: 3,
  the polynucleotide (g) being a polynucleotide encoding a polypeptide having a sequence identity of 98% or higher with an amino acid sequence represented by SEQ ID NO: 4,
  the polynucleotide (i) being a polynucleotide encoding a polypeptide having a sequence identity of 98% or higher with an amino acid sequence represented by SEQ ID NO: 5,
  the polynucleotide (k) being a polynucleotide encoding a polypeptide having a sequence identity of 98% or higher with an amino acid sequence represented by SEQ ID NO: 6, wherein
  the tobacco plant is *Nicotiana tabacum;*
  the mutation is introduced into each of at least two of the nucleotide products (1)— (3);
  the mutation that causes the functional suppression is selected from the group consisting of a frame-shift mutation or a nonsense mutation; and
  the functional suppression causes the number or weight of primary axillary buds to decrease to not more than ½ of that of a wild-type plant which is a wild type of a variety identical to that of said mutated tobacco plant that comprises at least two of said nucleotide products (1)— (3) and not having said at least two mutations.

12. An offspring or a bred progeny having said at least two mutations, wherein:
  the offspring is of the tobacco plant according to claim 1, and
  the bred progeny is obtained by crossing the tobacco plant according to claim 1.

13. A leaf tobacco harvested from the tobacco plant according to claim 1.

14. A leaf tobacco harvested from the offspring or the bred progeny according to claim 12.

15. A cured tobacco obtained from the leaf tobacco according to claim 13.

16. A cured tobacco obtained from the leaf tobacco according to claim 14.

17. A tobacco product obtained from the cured tobacco according to claim 15.

18. A tobacco product obtained from the cured tobacco according to claim 16.

* * * * *